US007683043B2

(12) United States Patent
Zerangue et al.

(10) Patent No.: US 7,683,043 B2
(45) Date of Patent: *Mar. 23, 2010

(54) CREATINE PHOSPHATE ANALOG PRODRUGS, COMPOSITIONS AND USES THEREOF

(75) Inventors: Noa Zerangue, Portola Valley, CA (US); Qingzhi Gao, Santa Clara, CA (US); William J. Dower, Menlo Park, CA (US)

(73) Assignee: XenoPort, Inc., Santa Clara, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 11/810,980

(22) Filed: Jun. 6, 2007

(65) Prior Publication Data

US 2008/0051371 A1 Feb. 28, 2008

Related U.S. Application Data

(60) Provisional application No. 60/811,085, filed on Jun. 6, 2006.

(51) Int. Cl.
*A61K 31/66* (2006.01)
*C07F 9/02* (2006.01)
(52) U.S. Cl. .................... 514/75; 514/463; 558/199; 549/448
(58) Field of Classification Search ............. 558/199; 549/448, 446; 514/75, 463, 76
See application file for complete search history.

(56) References Cited

U.S. PATENT DOCUMENTS

| 5,321,030 | A | 6/1994 | Kaddurah-Daouk et al. |
| 5,324,731 | A | 6/1994 | Kaddurah-Daouk et al. |
| 5,998,457 | A | 12/1999 | Kaddurah-Daouk et al. |
| 6,075,031 | A | 6/2000 | Kaddurah-Daouk et al. |
| 6,706,764 | B2 | 3/2004 | Kaddurah-Daouk et al. |
| 6,897,334 | B2 | 5/2005 | Vennerstrom |
| 2002/0161049 | A1 | 10/2002 | Kaddurah-Daouk et al. |
| 2003/0018082 | A1 | 1/2003 | Kaddurah-Daouk et al. |
| 2004/0054006 | A1 | 3/2004 | Kaddurah-Daouk et al. |
| 2004/0102419 | A1 | 5/2004 | Kaddurah-Daouk et al. |
| 2004/0102525 | A1 | 5/2004 | Kozachuk |
| 2004/0106680 | A1 | 6/2004 | Kaddurah-Daouk et al. |
| 2004/0116390 | A1 | 6/2004 | Kaddurah-Daouk et al. |
| 2004/0126366 | A1 | 7/2004 | Kaddurah-Daouk et al. |
| 2005/0049428 | A1 | 3/2005 | Vennerstrom |
| 2005/0256134 | A1 | 11/2005 | Kaddurah-Daouk et al. |
| 2007/0281909 | A1 | 12/2007 | Zerangue et al. |
| 2007/0281910 | A1 | 12/2007 | Zerangue et al. |
| 2007/0281983 | A1 | 12/2007 | Gao et al. |
| 2007/0281995 | A1 | 12/2007 | Gao et al. |
| 2007/0281996 | A1 | 12/2007 | Gao et al. |

FOREIGN PATENT DOCUMENTS

FR 75327 E 6/1961

| WO | WO 90/09192 | 8/1990 |
| WO | WO 92/08456 | 5/1992 |
| WO | WO 2004/071406 A2 | 8/2004 |

OTHER PUBLICATIONS

Annesley et al., "Cyclocreatine phosphate as a substitute for creatine phosphate in vertebrate tissues. Energetic considerations," *Academic Press, Inc.*, 74(1): 185-190 (1977).
Balestrino et al., "Role of creatine and phosphocreatine in neuronal protection from anoxic and ischemic damage," *Amino Acids*, 23: 221-229 (2002).
Blandini et al., "Glutamate and Parkinson's Disease," *Molecular Neurobiology*, 12: 73-94 (1996).
Butterfield et al., "Brain protection oxidation in age-related neurodegenerative disorders that are associated with aggregated proteins," *Elsevier Science Ltd*, 122: 945-962 (2001).
Cimino et al., "Neuroprotective effect of simvastatin in stroke: a comparison between adult and neonatal rat models of cerebral ischemia," *NeuroToxicology*, 26: 929-933 (2005).
Clark, "Creatine and Phosphocreatine: A Review of Their USe in Exercise and Sport," *Journal of Athletic Training*, 32: 45-51 (1997).
Coplan, et al., "Decreased choline and creatine concentrations in centrum semiovale in patients with generalized anxiety disorder: Relationship to IQ and early trauma," *Psychiatry Research: Neuroimaging*, 147: 27-39 (2006).
Cramer et al., "Die Syntheses der Argininphosphorsaure und die Reaktion von Isoureidophosphonaten mit Aminen," *Chemishe Berichte Jahrg.*, 95:1670-1682 (1962), English Abstract.
Deicken et al., "[31]Phosphorus Magnetic Resonance Spectroscopy of the Frontal and parietal Lobes in Chronic Schizophrenia," *Society of Biological Psychiatry*, 36: 503-510 (1994).
Dechent et al., "Increase of total creatine in human brain after oral supplementation of creatine-monohydrate," *The American Journal of Physiology—Regulatory, Integrative and Comparative Physiology*, 277:698-704 (1999).
Dzeja and Terzic, "Review Phosphotransfer networks and cellular energetics," *The journal of Experimental Biology*, 206: 2039-2047 (2003).
Ebadi et al., "Oxidative Stress and Antioxidant Therapy in Parkinson's Disease," *Progress Neurobiology*, 48:1-19 (1996).
Fukuzako, "Neurochemical Investigation of the Schizophrenic Brain by In Vivo Phosphorus Magnetic Resonance Spectroscopy," *World Journal Biolgy Psychiatry*, 2:70-82 (2001).
Gangadhar et al., "Developmental reflexes and [31]P Magnetic Resonance Spectroscopy of basal ganglia in antipsychotic-naïve schizophrenia," *Progress in Neuro-Psychopharmacology & Biological Psychiatry*, 30: 910-913 (2006).
Griffiths and Walker, "Accumulation of Analog of Phosphocreatine in Muscle of Chicks Fed 1-Carboxymethyl-2-iminoimidazolidine (Cyclocreatine)," *The Journal of Biological Chemistry*, 251(7): 2049-2054 (1976).

(Continued)

*Primary Examiner*—Rei-tsang Shiao
(74) *Attorney, Agent, or Firm*—Finnegan, Henderson, Farabow, Garrett & Dunner, LLP

(57) ABSTRACT

Membrane permeable prodrugs of creatine phosphate analogs, pharmaceutical compositions comprising membrane permeable prodrugs of creatine phosphate analogs, and methods of treating diseases such as ischemia, heart failure, and neurodegenerative disorders comprising administering prodrugs of creatine phosphate analogs, or pharmaceutical compositions thereof are disclosed.

26 Claims, 1 Drawing Sheet

OTHER PUBLICATIONS

Harris et al., "Elevation of creatine in resting and exercised muscle of normal subjects by creatine supplementation," *Clinical Science*, 83:367-74 (1992).

He et al.,"Relapsing-Remitting Multiple Sclerosis: Metabolic Abnormality in Nonenhancing Lesions and Normal-appearing White Matter at MR Imaging: Initial Experience," *Radiology*, 234:211-217 (2005).

Hu, et al., "Spectral pattern of total creatine and trimethyl ammonium in multiple sclerosis,". *Magnetic Resonance Imaging*, 22: 427-429 (2004).

Ingwall and Weiss, "Is the Failing Heart Energy Starved?: On Using Chemical Energy to Support Cardiac Function," *Circulation Research*, 95:135-145 (2004).

Jenner and Olanow., "Understanding Cell Death in Parkinson's Disease," *Annals of Neurology*, 44(Suppl 1): S72-S84 (1998).

Juhn et al., "Oral Creatine Supplementation and Athletic Performance: A Critical Review," *Clinical Journal of Sport Medicine*, 8: 286-297 (1998).

Kato et al., "Reduction of brain phospphocreatine in bipolar II disorder detected by phosphorus-31 magnetic resonance spectroscopy," *Journal of Affective Disorders*, 31:125-133 (1994).

Klivenyi et al., "Neuroprotective effects of creatine in a transgenic animal model of amyotrophic lateral sclerosis," *Nature Medicine*, 5:347-350 (1999).

Kongas and Van Beek, "Creatine kinase in energy metabolic signaling in muscle," $2^{nd}$ *Int. Conf. Systems Biol* 2001, Los Angeles CA, Omnipress, Madison, WI, 198-207 (Abstract Only).

Konstas et al., "Neuroprotection for Ischemic Stroke Using Hypothermia," *Neurocritical Care*, 4:168-78 (2006).

Lambert et al., "Influence of Creatine monohydrate Ingestion on Muscle metabolites and Intense Exercise Capacity in Individuals With Multiple Sclerosis," *The American Academy of Physical Medicine and Rehabilitation*, 84: 1206-1210 (2003).

Lowe and Sproatl, "Evidence for an Associative Mechanism in the Phosphoryl Transfer Step Catalyzed by Rabbit Muscle Creatine Kinase," *The Journal of Biological Chemistry*, 225 (9):3944-51 (1980).

Lyoo et al., "Multinuclear magnetic resonance spectroscopy of high-energy phosphate metabolites in human brain following oral supplementation of creatine-monohydrate," *Psychiatry Res: Neuroimaging*, 123: 87-100 (2003).

Martin, "Molecular Basis of the Neurodegenerative Disorders," *The New England Journal of Medicine*, 340 (25): 1970-80 (1999).

Martin, "Animal models sensitive to anti-anxiety agents," *Acta Psychiatr Scan*, 98 (Suppl 393): 74-80 (1998).

Matthews et al., "Creatine and Cyclocreatine Attenuate MPTP Neurotoxicity," *Experimental Neurology*, 157:142-149 (1999).

McLaughlin and Cohn, "Specificity of Creatine Kinase for Guanidino Substrates," *The Journal of Biological Chemistry*, 247: 4382-4388 (1972).

Meininger et al., Clinical Trials in ALS: "What Did We Learn From Recent Trials in Humans?"ALS National Referral and Coordinating Centre, Neurodegenerative DIs 2:208-214 (2005).

Minderhoud et al., "In Vivo Phosphorus Magnetic Resonance Spectroscopy in Multiple Sclerosis," *Archives Neurology*, 49:161-5 (1992).

Mold et al., "Creatine Ethyl Ether," *J. Am. Chem. Soc.* 77: 178-80(1955).

Mustoe, "Understanding chronic wounds: a unifying hypothesis on their pathogenesis and implications for therapy," *The American Journal of Surgery*, 187: S65-S70 (2004).

Nicolaou, et al., "Design, Synthesis and Biological Evaluation of Nonpeptide Integrin Antagonists," *Bioorganic & Medicinal Chemistry*, 6:1185-1208 (1998).

Nguyen, "Synthesis and Enzyme Studies Using Creatine Analogues," Thesis, *Pharmaceutical Chemistry, University of California*, San Francisco (1983).

Pettegrew et al., "Alterations of Cerebral metabolism in probable Alzheimer's Disease: A preliminary Study," *Neurobiology of Aging*, 15(1):117-132 (1994).

Pratico et al., "Increased F2-isoprostanes in Alzheimer's disease: evidence for enhanced lipid peroxidation *n v vo,"FASEB Journal*, 12: 1777-1783 (1998).

Roberts and Walker, "Higher Homolog and N-Ethyl Analog of Creatine as Synthetic Phosphagen Precursors in Brain, Heart, and Muscle, Repressprs of Liver Amidinotransferase, and Substrates for Creatine Catabolic," The Journal of *Bioogical Chemistry*, 260 (5):13502-13508 (1995).

Roberts and Walker, "Synthesis and Accumulation of an Extremely Stable High-Energy Phosphate Compound by Muscle, Heart, and Brain of Animals Fed the Creatine Analog, 1-Carboxyethyl-2-iminoimidazolidine (Homocyclocreatine)," *Archives of Biochemistry and Biophysics*, 220(2): 563-571(1983).

Robinson and Roskamp, "Solid Phase Synthesis of Guanidines," *Tetrahedron*, 53(19): 6697-6705 (1997).

Rowland and Schneider, "Amyotrophic Lateral Sclerosis," *The New England Journal of Medicine*, 344 (22): 1688-1700 (2001).

Rowley et al., "On the Specificity of Creatine Kinase. New Glycocyamines and Glycocyamine Analogs Related to Creatine," *Journal Of The American Chemical Society*, 93:21, 5542-5551(1971).

Ryu et al., "The therapeutic role of creatine in Huntington's disease," *Pharmacology & Therapeutics*, pp. 1-15 (2005).

Saks et al., "Cardiac system bioenergetics: metabolic basis of the Frank-Starling law,"*Japanese Physiological Society*, 571.2: 253-273 (2006).

Schulze, "Creatine deficiency syndromes," *Molecular and Celular Biochemistry*, 244: 143-150 (2003).

Segal et al., "Serum creatine kinase level in unmedicated nonpsychotic, psychotic, bipolar and schizoaffective depressed patients," *European Neuropsychopharmacology*, 17: 194-198 (2007).

Smith et al., "Amyloid-β Deposition in Alzheimer Transgenic Mice Is Associated with Oxidative Stree," *Journal of Neurochemistry*, 70 (5): 2212-2215 (1998).

Snow and Murphy, "Creatine and the creatine tramsporter: A review," *Molecular and Cellular Biochemistry*, 224:169-181(2001).

Stockler-Ipsiroglu et al. "Disorders of Creatine Metabolism," in *Physician's Guide to the Treatment and Follow up of Metabolic Diseases*, Chapter 24, 255-256, (2004).

Stork and Renshaw, "Mitochondrial dysfunction in bipolar disorder: evidence from magnetic resonance spectroscopy research," *Molecular Psychiatry*, 900-919 (2005).

Sun and Chen, "Oxidative Stree and Neurodegenerative Disorders," Journal of *Biomedical Science*, 5: 401-414 (1998).

Tarnopolsky, "Creatine Supplementation Results in Elevated Phosphocreatine/Adenosine Triphosphate 9 ATP) Ratios in the Calf Muscle of Athletes but Not in Patients with Myopathies," *Annals of Neurology*, 52 (1): 126-129 (2002).

Tartaglia et al., "The Relationship Between Diffuse Axonal Damage and Fatigue in Multiple Sclerosis," *Achieves Neurology*, 61: 201-207 (2004).

Terjung et al., "The physiological and health effects of oral creatine supplementation," *American College of Sports Medicine*, 32 (3): 706-717 (2000).

Vandenberghe et al., "Long-term creatine intake is beneficial to muscle performance during resistance training," *Journal of Applied Physiology*, 83: 2055-2063, (1997).

Van Au Duong, et al., "Relationship between gray matter metabolic abnormalities and white matter inflammation in patients at the very early stage of MS," A MRSI *Journal Neurology*,. (2007).

Ventura-Clapier, et al., "Energy metabolism in heart failure," *Journal Physiology*, 555(1): 1-13.(2003).

Virley, "Developing therapeutics for the treatment of multiple sclerosis," *The Journal of the American Society for Experimental neuro Therapeutics*, 2(4): 638-649 (2005).

Volz et al., "$^{31}$Phosphorus Magnetic Resonsnce Spectroscopy of the Dorsolateral Prefrontal Region in Schizophrenics-A Study Including 50 Patients and 36 Controls," *Biological Psychiatry*, 44: 399-404 (1998).

Volz et al., "Reduced Phosphodiesters and High-Energy Phosphates in the Frontal Lobe of Schizophrenic patients: A $^{31}$P Chemical Shift Spectroscopic-Imaging Study," *Biological Psychiatry*, 47: 954-961(2000).

Walsh et al., "The role of Phosphorylcreatine and Creatine in the Regulation of Mitochondrial Respiration in Human Skeletal Muscle," *The Journal of Physiology*, 537: 971-978 (2001).

Wang, "Synthesis and properties of N-Acetimidoyl Derivatives of Glycine and Sarcosine," *The Journal of Organic Chemistry*, 39 (24): 3591-3594 (1974).

Wasterlain et al., "Posthypoxic treatment with felbamate is neuroprotective in a rat model of hypoxia-ischemia," *Neurology*, 43: 2303-10 (1993).

Wingerchuk, et al., "Multiple Sclerosis: Current Pathophysiological Concepts," *Laboratory Investigation*, 81(3): 263-281(2001).

Wyss and Kaddurah-Daouk, "Creatine and Creatinine Metabolism," *Physiological Reviews*, 80: 1107-1213 (2000).

Wyss and Schulze, "Health Implications of Creatine: Can Oral Creatine Supplementation Protect Against Neurological and Atherosclerotic Disease?" *Neuroscience*, 112(2): 243-260 (2002).

Yatin et al., "The Antioxidant Vitamin E Modulates Amyloid β-Pepide-Induced Creatine Kinase Acivity Inhibition and Increased Protein Oxidation: Implications for the Free Radical Hypothesis of Alzheimer's Disease," *Neurochem Research*, 24(3): 427-435 (1999).

Zhu et al., "prophylactic Creatine Administration Mediates Neuroprotection in Cerebral Ischemia in Mice," *Journal of Neuroscience*, 24(26), 5909-5912 (2004).

Alexander et al. "(Acyloxy)alkyl Carbamates as Novel Bioreversible Prodrugs for Amines: Increased Permeation through Biological membranes," J. Med. Chem., vol. 31, pp. 318-322 (1988).

Cundy et al., "XP13512 [(±)-1-([(α-Isobutanoyloxyethoxy)carbonyl]aminomethyl)-1-cyclohexane Acetic Acid], A novel Gabapentin Prodrug: I. Design, Synthesis, Enzymatic Conversion to Gabapentin, and Transport by Intestinal Solute Transporters," The Journal of Pharmacology and Experimental Therapeutics, vol. 311 (1), pp. 315-323 (2004).

Dedeoglu et al., "Creatine therapy provides neuroprotection after onset of clinical symptoms in Huntington's disease transgenic mice," Journal of Neurochemistry, 85:1359-67 (2003).

International Search Report and Written Opinion of the International Searching Authority mailed Feb. 15, 2008 for International Application No. PCT/US2007/013454 filed Jun. 6, 2007.

International Search Report and Written Opinion of the International Searching Authority mailed Oct. 11, 2007 for International Application No. PCT/US2007/013457 filed Jun. 6, 2007.

International Search Report and Written Opinion of the International Searching Authority, mailed Oct. 19, 2007, for PCT Application No. PCT/US2007/013455, filed Jun. 6, 2007.

Linton et al., "A Versatile One-Pot Synthesis of 1,3-Substituted Guanidines from Carbamoyl Isothiocyanates," Journey of Organic Chemistry ,65: 1566-1568 (2000).

Speer et al, "Creatine transporters: A reappraisal," Molecular and Cellular Biochemistry, 256/257: pp. 407-424 (2004).

Sykut-Cegielska et al., Acta Biochimica Polonica, vol. 51. No. 4. (2004).

Creatine Phosphate

| | calc pKa |
|---|---|
| CO₂H | 3.4 |
| PO₃H (1) | 5.0 |
| PO₃H (2) | 1.5 |
| NH | 12.5 |
| cLogD | -7.8 |

Example Prodrug

| | calc pKa |
|---|---|
| CO₂H | 4.7 |
| NH | -0.3 |
| cLogD | 0.5 |

CREATINE PHOSPHATE ANALOG PRODRUGS, COMPOSITIONS AND USES THEREOF

This application claims the benefit under 35 U.S.C. §119(e) of U.S. Provisional Application Ser. No. 60/811,085 filed Jun. 6, 2006, which is incorporated by reference herein in its entirety.

FIELD

Disclosed herein are membrane permeable prodrugs of creatine phosphate analogs, pharmaceutical compositions comprising membrane permeable prodrugs of creatine phosphate analogs, and methods of treating diseases such as ischemia, heart failure, and neurodegenerative disorders comprising administering prodrugs of creatine phosphate analogs or pharmaceutical compositions thereof.

BACKGROUND

Precise coupling of spatially separated intracellular ATP-producing and ATP-consuming processes is fundamental to the bioenergetics of living organisms. Integrated spatially arranged phosphotransfer systems catalyzed by creatine kinase, adenylate kinase, carbonic anhydrase, and glycolytic enzymes provide efficient high-energy phosphoryl transfer to support cellular functions and maintain intracellular energy homeostasis under stress (see, e.g., Dzeja and Terzic, *J Experimental Biol* 2003, 206, 2039-2047). Creatine kinase catalyzes the reversible transfer of the N-phosphoryl group from phosphocreatine to ADP to regenerate ATP and plays a key role in the energy homeostasis of cells with intermittently high, fluctuating energy requirements such as skeletal and cardiac muscle, neurons, photoreceptors, spermatozoa, and electrocytes. The creatine kinase system has a dual role in intracellular energy metabolism—functioning as an energy buffer to restore depleted ATP levels at sites of high ATP hydrolysis, and to transferring energy in the form of phosphocreatine from the mitochondria to other parts of the cell by a process involving intermediate energy carriers, several enzymatic reactions, and diffusion through various intracellular structures.

Many pathological disease states arise from a dysfunction in energy metabolism. Cellular depletion of ATP stores, as occurs for example during tissue ischemia, results in impaired tissue function and cell death. Of foremost medical relevance, ischemia-related cardiovascular disease such as stroke and heart attack remains a leading cause of death and morbidity in North America and Europe. Thus, strategies that can prevent or reverse ischemia-related tissue damage are expected to have a major impact on public health. Energy depletion also contributes to tissue damage during surgery and is a common cause of organ transplant failure. Furthermore, reperfusion with oxygen-containing solutions can further exacerbate tissue health through production of oxygen radicals. Therefore, a method to rapidly restore ATP levels without causing reperfusion injury is likely to have many therapeutic applications. Neurodegenerative diseases such as Parkinson's disease, Alzheimer's disease, and Huntington's disease are associated with impaired energy metabolism, and strategies for improving ATP metabolism could potentially minimize loss of neurons and thereby improve the prognosis of patients with these diseases. Finally, impaired energy metabolism is an important factor in muscle fatigue and limits physical endurance. Therefore, a method of preventing or reversing ATP depletion in ischemic or metabolically active tissues is likely to have broad clinical utility in a wide range of indications.

A large body of research indicates that the loss of cellular ATP due to oxygen and glucose deprivation during ischemia is a cause of tissue death. To prevent this, mammalian cells harbor protective biochemical mechanisms for minimizing ATP depletion during ischemia and episodes of high metabolic demand as occurs in metabolically active brain or muscle tissues. The creatine kinase system is a key biochemical mechanism that prevents ATP depletion in mammalian cells. Phosphagens such as creatine phosphate (4):

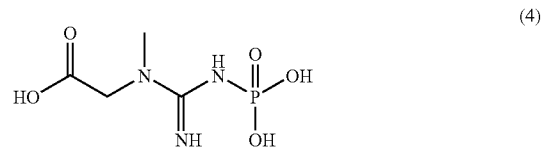

(4)

are high-energy phosphate sources that can regenerate ATP when intracellular levels of ATP fall. The level of creatine phosphate in a cell is an important predictor of resistance to ischemic insult, and remaining stores of creatine phosphate are correlated with the extent of tissue damage. Studies have documented the importance of creatine phosphate levels in cardiac and brain ischemia, neuronal degeneration, organ transplant viability, and muscle fatigue (see, e.g., Wyss and Kaddurah-Daouk, *Physiological Reviews* 2000, 80(3), 1107-1213, which is incorporated by reference herein in its entirety). Accordingly, the administration of creatine or creatine phosphate for treating these and other diseases is being explored (see, e.g., Kaddurah-Daouk et al., U.S. Application Publication Nos. 2005/0256134, and 2003/0018082, and U.S. Pat. No. 6,075,031 (use of creatine kinase analogs for treating glucose metabolic disorders); Kaddurah-Daouk, U.S. Application Publication No. 2004/0116390, and U.S. Pat. No. 5,998,457 (obesity and related disorders), Kaddurah-Daouk, U.S. Application Publication No. 2004/0054006 (transmissible spongiform encephalopathies); Kaddurah-Daouk et al., U.S. Application Publication Nos. 2004/0102419, 2004/0106680, and 2002/0161049, and U.S. Pat. No. 6,706,764 (diseases of the central nervous system); and Lambert et al., *Adv Phys Med Rehab*, 2003, 84(8), 1206-1210 (multiple sclerosis).

Creatine, (5),

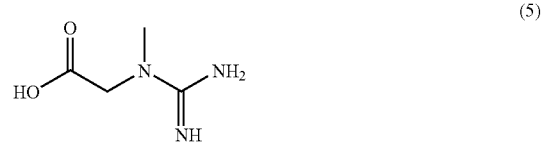

(5)

supplementation increases intracellular creatine phosphate levels (Harris et al., *Clinical Sci* 1992, 83, 367-74). Creatine phosphate (2 gm/day) given to athletes during strenuous endurance training has allowed the athletes to train longer with less muscle stiffness. Because creatine phosphate is readily metabolized when administered orally it must be administered intramuscularly or intravenously to be effective. Creatine easily crosses the blood-brain barrier and brain creatine levels can be increased via oral administration (Dechent et al., *Am J Physiol* 1999, 277, R698-704). Prolonged creatine supplementation can elevate the cellular pools of creatine phosphate and increase resistance to tissue ischemia and muscle fatigue. However, creatine supplementation typically takes weeks to increase creatine phosphate levels, and the overall increase is generally fairly small (<50%). For example, human studies show that in healthy volunteers cerebral creatine phosphate can be increased only by about 10% by oral creatine administration (Dechent et al., *Am J Physiol* 1999, 277, R698-R704). Interestingly, increases in tissue creatine phosphate levels following oral creatine supplementation are long-lasting (>14 days), suggesting that strategies that increase creatine phosphate could have long lasting beneficial effects and would be effective with infrequent dosing. However, acute application of creatine is not effective in restoring tissue ATP levels, and therefore may have limited value in emergency care situations. Application of creatine phosphate to cells does not raise intracellular creatine phosphate, since due to its high polarity (hydrophilicity), creatine phosphate is not taken up into cells and does not readily cross barrier tissues such as the blood-brain-barrier. Creatine phosphate is also rapidly metabolized in biological fluids. Conjugating creatine phosphate with a protein moiety has been proposed as a strategy for enhancing translocation through barrier tissue (see, e.g., Kaddurah-Daouk et al., U.S. Application Publication No. 2004-0126366). Thus, although administration of creatine phosphate may have some therapeutic usefulness, a modified creatine phosphate molecule that is more stable and is more permeable to barrier tissues and cellular membranes would have enhanced therapeutic value.

Creatine phosphate analog prodrugs provided by the present disclosure are designed to be stable in biological fluids, to enter cells by either passive diffusion or active transport, and to release the corresponding creatine phosphate analog into the cellular cytoplasm. Such prodrugs can also cross important barrier tissues such as the intestinal mucosa, the blood-brain barrier, and the blood-placental barrier. Because of the ability to pass through biological membranes, creatine phosphate analog prodrugs can restore and maintain energy homeostasis in ATP depleted cells via the creatine kinase system, and rapidly restore ATP levels to protect tissues from further ischemic stress. Prodrugs of creatine phosphate analogs having a higher free energy, e.g., cyclocreatine, or lower affinity for creatine kinase, and which can regenerate ATP under more severe conditions of energy depletion are also disclosed. Creatine phosphate analog prodrugs provided by the present disclosure can also be used to deliver sustained systemic concentrations of the corresponding creatine phosphate analog.

SUMMARY

In a first aspect, compounds of Formula (I) are provided:

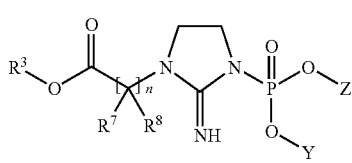

a pharmaceutically acceptable salt thereof, or a pharmaceutically acceptable solvate of any of the foregoing, wherein:

n is selected from 1 and 2;

Y and Z are independently selected from Formula (1), Formula (2), and Formula (3):

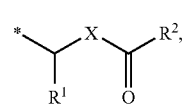

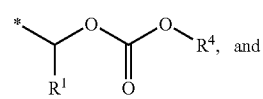

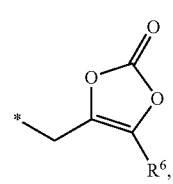

wherein:

each X is independently selected from O and S;

each $R^1$ and $R^2$ is independently selected from hydrogen, $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl;

each $R^4$ is independently selected from $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl; and each $R^6$ is independently selected from hydrogen, $C_{1-8}$ alkyl, substituted $C_{1-8}$ alkyl, $C_{5-12}$ cycloalkyl, substituted $C_{5-12}$ cycloalkyl, $C_{5-12}$ aryl, and $C_{5-12}$ substituted aryl;

$R^3$ is selected from hydrogen, $C_{1-8}$ alkyl, substituted $C_{1-8}$ alkyl, $C_{1-8}$ heteroalkyl, substituted $C_{1-8}$ heteroalkyl, $C_{5-12}$ cycloalkyl, substituted $C_{5-12}$ cycloalkyl, $C_{6-20}$ cycloalkylalkyl, substituted $C_{6-20}$ cycloalkylalkyl, $C_{6-20}$ heterocycloalkylalkyl, substituted $C_{6-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl; and each $R^7$ and $R^8$ is independently selected from hydrogen, $C_{1-8}$ alkyl, and substituted $C_{1-8}$ alkyl.

In a second aspect, compounds of Formula (II) are provided:

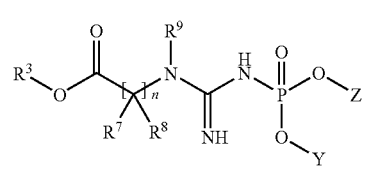

a pharmaceutically acceptable salt thereof, or a pharmaceutically acceptable solvate of any of the foregoing, wherein:

n is selected from 1 and 2;

Y and Z are independently selected from Formula (1), Formula (2), and Formula (3):

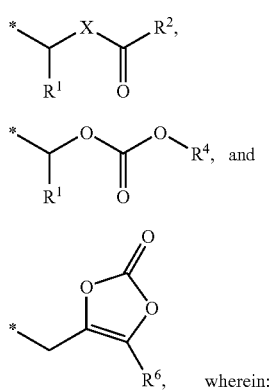

wherein:

each X is independently selected from O and S;

each $R^1$ and $R^2$ is independently selected from hydrogen, $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl;

each $R^4$ is independently selected from $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl; and each $R^6$ is independently selected from hydrogen, $C_{1-8}$ alkyl, substituted $C_{1-8}$ alkyl, $C_{5-12}$ cycloalkyl, substituted $C_{5-12}$ cycloalkyl, $C_{5-12}$ aryl, and $C_{5-12}$ substituted aryl;

$R^3$ is selected from hydrogen, $C_{1-8}$ alkyl, substituted $C_{1-8}$ alkyl, $C_{1-8}$ heteroalkyl, substituted $C_{1-8}$ heteroalkyl, $C_{5-12}$ cycloalkyl, substituted $C_{5-12}$ cycloalkyl, $C_{6-20}$ cycloalkylalkyl, substituted $C_{6-20}$ cycloalkylalkyl, $C_{6-20}$ heterocycloalkylalkyl, substituted $C_{6-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl;

each $R^7$ and $R^8$ is independently selected from hydrogen, $C_{1-8}$ alkyl, and substituted $C_{1-8}$ alkyl; and $R^9$ is selected from hydrogen, $C_{1-8}$ alkyl, substituted $C_{1-8}$ alkyl, $C_{1-8}$ heteroalkyl, and substituted $C_{1-8}$ heteroalkyl.

In a third aspect, pharmaceutical compositions are provided comprising a therapeutically effective amount of a compound of Formula (I) and/or Formula (II), a pharmaceutically acceptable salt thereof, or a pharmaceutically acceptable solvate of any of the foregoing, and a pharmaceutically acceptable vehicle.

In a fourth aspect, methods are provided for treating a disease in a patient associated with a dysfunction in energy metabolism such as ischemia, oxidative stress, a neurodegenerative disease, including amyotrophic lateral sclerosis (ALS), Huntington's disease, Parkinson's disease, or Alzheimer's disease, ischemic reperfusion injury, a cardiovascular disease, multiple sclerosis (MS), a psychotic disorder, a genetic disease affecting the creatine kinase system, or muscle fatigue in a patient comprising administering to a patient in need of such treatment a therapeutically effective amount of a compound of Formula (I) and/or Formula (II) or a pharmaceutical composition comprising a compound of Formula (I) and/or Formula (II).

In a fifth aspect, methods are provided for enhancing muscle strength in a patient comprising administering to a patient in need of such enhancement a therapeutically effective amount of a compound of Formula (I) and/or Formula (II) or a pharmaceutical composition comprising a compound of Formula (I) and/or Formula (II)

In a sixth aspect, methods are provided for increasing the viability of a tissue or an organ comprising contacting the tissue or the organ with an effective amount of a compound of Formula (I) and/or Formula (II) or a pharmaceutical composition comprising a compound of Formula (I) and/or Formula (II).

In a seventh aspect, methods are provided for improving the viability of isolated cells comprising contacting the cells with an effective amount of a compound of Formula (I) and/or Formula (II) or a pharmaceutical composition comprising a compound of Formula (I) and/or Formula (II).

In an eighth aspect, methods of treating a disease associated with oxidative stress are provided comprising administering to a patient in need of such treatment an effective amount of a compound of Formula (I) and/or Formula (II) or a pharmaceutical composition comprising a compound of Formula (I) and/or Formula (II).

In a ninth aspect, methods of treating a tissue or organ manifesting a dysfunction in energy metabolism are provided comprising contacting a compound of Formula (I) and/or Formula (II) or a pharmaceutical composition comprising a compound of Formula (I) and/or Formula (II) with the tissue or organ.

In a tenth aspect, methods of effecting energy homeostasis in a tissue or an organ are provided comprising contacting a compound of Formula (I) and/or Formula (II) or a pharmaceutical composition comprising a compound of Formula (I) and/or Formula (II) with the tissue or the organ.

In an eleventh aspect, methods of treating an oxidatively stressed tissue or organ are provided comprising contacting a compound of Formula (I) and/or Formula (II) or a pharmaceutical composition comprising a compound of Formula (I) and/or Formula (II) with the tissue or organ.

Accordingly, membrane permeable creatine phosphate analog prodrugs, pharmaceutical compositions comprising membrane permeable creatine phosphate analog prodrugs, and methods of using membrane permeable creatine phosphate analog prodrugs, and pharmaceutical compositions thereof, are disclosed herein.

BRIEF DESCRIPTION OF THE DRAWINGS

The skilled artisan will understand that the drawing, described herein, is for illustration purposes only. The drawing is not intended to limit the scope of the present disclosure.

DETAILED DESCRIPTION

Definitions

Figure 1:
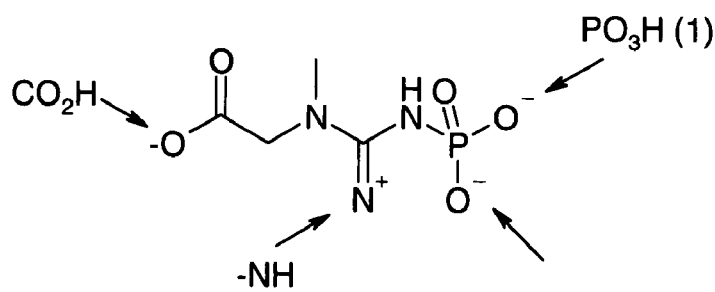
FIG. 1 shows calculated pKas for creatine phosphate and for an example of a creatine phosphate prodrug.
Figure 1:
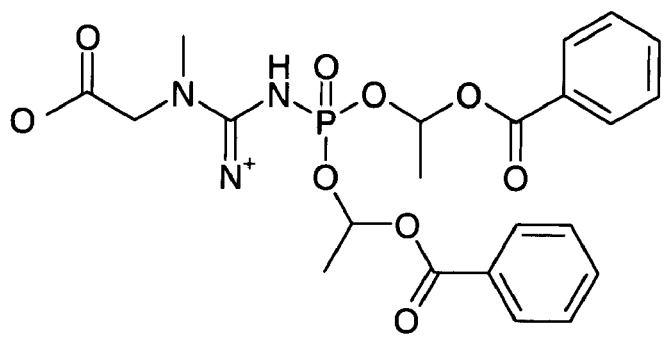

A dash ("—") that is not between two letters or symbols is used to indicate a point of attachment for a moiety or substituent. For example, —CONH$_2$ is attached through the carbon atom.

"Alkyl" by itself or as part of another substituent refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group can have from 1 to 20 carbon atoms, in certain embodiments, from 1 to 10 carbon atoms, in certain embodiments, from 1 to 6 carbon atoms, and in certain embodiments, from 1 to 3 carbon atoms.

"Alkoxy" by itself or as part of another substituent refers to a radical —OR$^{31}$ where R$^{31}$ is chosen from alkyl, heteroalkyl, cycloalkyl, heterocycloalkyl, cycloalkylalkyl, heterocycloalkylalkyl, aryl, heteroaryl, arylalkyl, and heteroarylalkyl, as defined herein. Examples of alkoxy groups include, but are not limited to, methoxy, ethoxy, propoxy, butoxy, cyclohexyloxy, and the like.

"Creatine phosphate analog" means a compound of Formula (III) or Formula (IV):

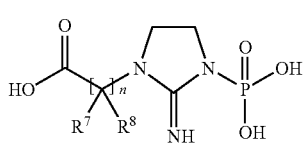

(III)

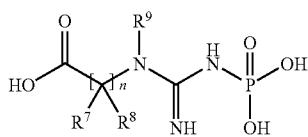

(IV)

wherein:
  n is selected from 1 and 2;
  each R$^7$ and R$^8$ is independently selected from hydrogen, C$_{1-8}$ alkyl, and substituted C$_{1-8}$ alkyl; and
  R$^9$ is selected from hydrogen, C$_{1-8}$ alkyl, substituted C$_{1-8}$ alkyl, C$_{1-8}$ heteroalkyl, and substituted C$_{1-8}$ heteroalkyl.

In certain embodiments of a compound of Formula (III) or Formula (IV), n is 1, and in certain embodiments, n is 2. In certain embodiments of a compound of Formula (III) or Formula (IV), each R$^7$ and R$^8$ is hydrogen. In certain embodiments of a compound of Formula (IV), R$^9$ is selected from hydrogen and C$_{1-4}$ alkyl, and in certain embodiments, R$^9$ is hydrogen. In certain embodiments of a compound of Formula (III) or Formula (IV), each substituent group is independently selected from halogen, —NO$_2$, —OH, —COOH, —NH$_2$, —CN, —CF$_3$, —OCF$_3$, C$_{1-8}$ alkyl, substituted C$_{1-8}$ alkyl, C$_{1-8}$ alkoxy, and substituted C$_{1-8}$ alkoxy. In certain embodiments of a compound of Formula (III) or Formula (IV), each substituent is independently selected from halogen, —OH, —CN, —CF$_3$, =O, —NO$_2$, C$_{1-3}$ alkoxy, C$_{1-3}$ alkyl, —COOR$^{10}$ wherein R$^{10}$ is chosen from hydrogen, C$_{1-3}$ alkyl, and —NR$^{11}$$_2$ wherein each R$^{11}$ is independently chosen from hydrogen and C$_{1-3}$ alkyl.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms, from 6 to 12 carbon atoms, and in certain embodiments, from 6 to 8 carbon atoms. Aryl, however, does not encompass or overlap in any way with heteroaryl, separately defined herein.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is C$_{6-30}$ arylalkyl, e.g., the alkanyl, alkenyl or alkynyl moiety of the arylalkyl group is C$_{1-10}$ and the aryl moiety is C$_{6-20}$, in certain embodiments, an arylalkyl group is C$_{6-20}$ arylalkyl, e.g., the alkanyl, alkenyl or alkynyl moiety of the arylalkyl group is C$_{1-8}$ and the aryl moiety is C$_{6-12}$.

"AUC" is the area under a curve representing the concentration of a compound or metabolite thereof in a biological fluid in a patient as a function of time following administration of the compound to the patient. In certain embodiments, the compound can be a prodrug and the metabolite can be a drug. Examples of biological fluids include plasma and blood. The AUC may be determined by measuring the concentration of a compound or metabolite thereof in a biological fluid such as the plasma or blood using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art. As relevant to the present disclosure, an AUC for a drug having a sulfonic acid group or metabolite thereof may be determined by measuring over time the concentration of the drug having a sulfonic acid group in the plasma, blood, or other biological fluid or tissue of a patient following administration of a corresponding prodrug of Formula (I) or Formula (II) to the patient.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"$C_{max}$" is the maximum concentration of a drug in the plasma or blood of a patient following administration of a dose of the drug or prodrug to the patient.

"$T_{max}$" is the time to the maximum (peak) concentration ($C_{max}$) of a drug in the plasma or blood of a patient following administration of a dose of the drug or prodrug to the patient.

"Compounds" of Formulae (I)-(IV) disclosed herein, also referred to as "compounds provided by the present disclosure" include any specific compounds within these formulae. Compounds may be identified either by their chemical structure and/or chemical name. When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds of Formula (I) and Formula (II) are also referred to as "prodrugs of the present disclosure."

Compounds of Formulae (I)-(IV) include, but are not limited to, optical isomers of compounds of Formulae (I)-(IV), racemates thereof, and other mixtures thereof. In such embodiments, the single enantiomers or diastereomers, i.e., optically active forms, can be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column. In addition, compounds of Formulae (I)-(IV) include Z- and E-forms (or cis- and trans-forms) of compounds with double bonds. In embodiments in which compounds of Formulae (I)-(IV) exist in various tautomeric forms, the compounds include all tautomeric forms of the compound.

Compounds of Formulae (I)-(IV) may also exist in several tautomeric forms including the enol form, the keto form, and mixtures thereof. Accordingly, the chemical structures depicted herein encompass all possible tautomeric forms of the illustrated compounds. Compounds of Formulae (I)-(IV) also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated, or N-oxides. Certain compounds may exist in multiple crystalline or amorphous forms. Compounds of Formulae (I)-(IV) include pharmaceutically acceptable salts thereof, or pharmaceutically acceptable solvates of the free acid form of any of the foregoing, as well as crystalline forms of any of the foregoing.

Further, when partial structures of the compounds are illustrated, an asterisk (*) indicates the point of attachment of the partial structure to the rest of the molecule.

"Corresponding creatine phosphate analog prodrug" refers to a compound of Formula (I) having the same n, $R^7$, and $R^8$ as a creatine phosphate analog of Formula (III), or a compound of Formula (II) having the same n, $R^7$, $R^8$, and $R^9$ as a creatine phosphate analog of Formula (IV).

"Corresponding creatine phosphate analog" refers to a compound of Formula (III) having the same n, $R^7$, and $R^8$ as a creatine phosphate analog prodrug of Formula (I), or a compound of Formula (IV) having the same n, $R^7$, $R^8$, and $R^9$ as a creatine phosphate analog prodrug of Formula (II).

"Creatine kinase system" includes, but is not limited to the creatine transporter, creatine, creatine kinase, creatine phosphate, and the intracellular energy transport of creatine, creatine kinase, and/or creatine phosphate. The creatine kinase system includes mitochondrial and cytoplasmic creatine kinase systems. Affecting the creatine kinase system refers to the transport, synthesis, metabolism, translocation, and the like, of the compounds and proteins comprising the creatine kinase system.

"Cycloalkyl" by itself or as part of another substituent refers to a saturated or partially unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{5-12}$ cycloalkyl, and in certain embodiments, $C_{3-7}$ cycloalkyl "Cycloalkylalkyl" by itself or as part of another substituent refers to an acyclic alkyl radical in which one of the hydrogen atoms bonded to a carbon atom, typically a terminal or sp$^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Disease" refers to a disease, disorder, condition, symptom, or indication.

"Halogen" refers to a fluoro, chloro, bromo, or iodo group.

"Heteroalkyl" by itself or as part of another substituent refer to an alkyl group in which one or more of the carbon atoms (and any associated hydrogen atoms) are independently replaced with the same or different heteroatomic groups. Examples of heteroatomic groups include, but are not limited to, —O—, —S—, —O—O—, —S—S—, —O—S—, —$NR^{37}R^{38}$—, =N—N=, —N=N—, —N=N—$NR^{39}R^{40}$, —$PR^{41}$, —$P(O)_2$—, —$POR^{42}$—, —O—$P(O)_2$—, —SO—, —$SO_2$—, —$SnR^{43}R^{44}$—, and the like, where $R^{37}$, $R^{38}$, $R^{39}$, $R^{40}$, $R^{41}$, $R^{42}$, $R^{43}$, and $R^{44}$ are independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Where a specific level of saturation is intended, the nomenclature "heteroalkanyl," "heteroalkenyl," or "heteroalkynyl" is used. In certain embodiments, $R^{37}$, $R^{38}$, $R^{39}$, $R^{40}$, $R^4$, $R^{42}$, $R^{43}$, and $R^{44}$ are independently chosen from hydrogen and $C_{1-3}$ alkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, in certain embodiments from 5- to 10-membered heteroaryl, and in certain embodiments from 6- to 8-heteroaryl. In certain embodiments heteroaryl groups are those derived from thiophene, pyrrole, benzothiophene, benzofuran, indole, pyridine, quinoline, imidazole, oxazole, or pyrazine.

"Heteroarylalkyl" by itself or as part of another substituent refers to an acyclic alkyl radical in which one of the hydrogen atoms bonded to a carbon atom, is replaced with a heteroaryl group. Typically a terminal or $sp^3$ carbon atom is the atom replaced with the heteroaryl group. Where specific alkyl moieties are intended, the nomenclature "heteroarylalkanyl," "heteroarylalkenyl," and "heterorylalkynyl" is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Immediately preceding embodiments" means the embodiments disclosed in the same paragraph.

"Leaving group" refers to an atom or a group capable of being displaced by a nucleophile and includes halogen, such as chloro, bromo, fluoro, and iodo, alkoxycarbonyl (e.g., acetoxy), aryloxycarbonyl, mesyloxy, tosyloxy, trifluoromethanesulfonyloxy, aryloxy (e.g., 2,4-dinitrophenoxy), methoxy, N,O-dimethylhydroxylamino, and the like.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom. Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Patient" refers to a mammal, for example, a human.

"Pharmaceutical composition" refers to at least one compound of Formula (I) or Formula (II) and at least one pharmaceutically acceptable vehicle, with which the at least one compound of Formula (I) or Formula (II) is administered to a patient, contacted with a tissue or organ, or contacted with a cell. "Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Prodrug" refers to a derivative of a drug molecule that requires a transformation within the body to release the active drug. Prodrugs are frequently, although not necessarily, pharmacologically inactive until converted to the parent drug. Prodrugs can be obtained by bonding a promoiety (defined herein) typically via a functional group, to a drug. For example, referring to compounds of Formula (I) or Formula (II), promoieties Z and/or Y are bonded to a creatine phosphate analog via a phosphinic acid functional group of the creatine phosphate analog. Promoiety $R^3$ can also be bonded to the creatine phosphate analogs. Compounds of Formula (I) and Formula (II) are prodrugs of creatine phosphate analogs that can be metabolized within a patient's body to release the corresponding creatine phosphate analog.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach, or the agent may be supplied exogenously. For example, for a prodrug of Formula (I), the drug is a creatine phosphate analog and the promoieties are R3, Y and/or Z where $R^3$, Y and Z are as defined herein.

"Protecting group" refers to a grouping of atoms, which when attached to a reactive group in a molecule masks, reduces, or prevents that reactivity. Examples of protecting groups can be found in Wuts and Greene, "Protective Groups in Organic Synthesis," John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003. Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of hydroxy protecting groups include, but are not limited to, those in which the hydroxy group is either acylated or alkylated such as benzyl, and trityl ethers as well as alkyl ethers, tetrahydropyranyl ethers, trialkylsilyl ethers, and allyl ethers.

"Solvate" refers to a molecular complex of a compound with one or more solvent molecules in a stoichiometric or non-stoichiometric amount. Such solvent molecules are those commonly used in the pharmaceutical art, which are known to be innocuous to recipient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a complex in which the one or more solvent molecules are water including monohydrates and hemi-hydrates.

"Substantially one diastereomer" refers to a compound containing two or more stereogenic centers such that the diastereomeric excess (d.e.) of the compound is greater than or about at least 90%. In certain embodiments, the d.e. is, for example, greater than or at least about 91%, about 92%, about 93%, about 94%, about 95%, about 96%, about 97%, about 98%, or about 99%.

"Substituted" refers to a group in which one or more hydrogen atoms are independently replaced with the same or different substituent(s). Examples of substituents include, but are not limited to, -M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —S(O)$_2$OH, —$S(O)_2R^{60}$, —$OS(O_2)O^-$, —$OS(O)_2R^{60}$, —P(O)($O^-$)$_2$, —P(O)($OR^{60}$)($O^-$), —OP(O)($OR^{60}$)($OR^{61}$), —C(O)$R^{60}$, —C(S)$R^{60}$, —C(O)$OR^{60}$, —C(O)$NR^{60}R^{61}$, —C(O)$O^-$, —C(S)$OR^{60}$, —$NR^{62}C(O)NR^{60}R^{61}$, —$NR^{62}C(S)NR^{60}R^{61}$, —$NR^{62}C(NR^{63})NR^{60}R^{61}$, and —$C(NR^{62})NR^{60}R^{61}$ where M is independently a halogen; $R^{60}$, $R^{61}$, $R^{62}$, and $R^{63}$ are independently chosen from hydrogen, alkyl, alkoxy, cycloalkyl, heterocycloalkyl, aryl, and heteroaryl, or $R^{60}$ and $R^{61}$ together with the nitrogen atom to which they are bonded form a ring chosen from a heterocycloalkyl ring. In certain embodiments, $R^{60}$, $R^{61}$, $R^{62}$, and $R^{63}$ are independently chosen from hydrogen, $C_{1-6}$ alkyl, $C_{1-6}$ alkoxy, $C_{3-12}$ cycloalkyl, $C_{3-12}$ heterocycloalkyl, $C_{6-12}$ aryl, and $C_{6-12}$ heteroaryl. In certain embodiments, a substituent group is independently chosen from halogen, —OH, —CN, —$CF_3$, =O, —$NO_2$, $C_{1-3}$ alkoxy, $C_{1-3}$ alkyl, —$COOR^{64}$ wherein $R^{64}$ is chosen from hydrogen and $C_{1-3}$ alkyl, and —$NR^{65}{}_2$ wherein each $R^{65}$ is independently chosen from hydrogen and $C_{1-3}$ alkyl. 19.

In certain embodiments, substituted aryl and substituted heteroaryl include one or more of the following substitute groups: F, Cl, Br, $C_{1-3}$ alkyl, substituted alkyl, $C_{1-3}$alkoxy, —$S(O)_2NR^{50}R^{51}$, —$NR^{50}R^{51}$, —$CF_3$, —$OCF_3$, —CN, —$NR^{50}S(O)_2R^{51}$, —$NR^{50}C(O)R^{51}$, $C_{5-10}$ aryl, substituted $C_{5-10}$ aryl, $C_{5-10}$ heteroaryl, substituted $C_{5-10}$ heteroaryl, —$C(O)OR^{50}$, —$NO_2$, —$C(O)R^{50}$, —$C(O)NR^{50}R^{51}$, —$OCHF_2$, $C_{1-3}$ acyl, —$SR^{50}$, —$S(O)_2OH$, —$S(O)_2R^{50}$, —$S(O)R^{50}$, —$C(S)R^{50}$, —$C(O)O^-$, —$C(S)OR^{50}$, —$NR^{50}C(O)NR^{51}R^{52}$, —$NR^{50}C(S)NR^{51}R^{52}$, and —$C(NR^{50})NR^{51}R^{52}$, $C_{3-8}$ cycloalkyl, and substituted $C_{3-8}$ cycloalkyl, wherein $R^{50}$, $R^{51}$, and $R^{52}$ are each independently selected from hydrogen and $C_1$-$C_4$ alkyl.

In certain embodiments, a substituent group can be selected from halogen, —$NO_2$, —OH, —COOH, —$NH_2$, —CN, —$CF_3$, —$OCF_3$, $C_{1-8}$ alkyl, substituted $C_{1-8}$ alkyl, $C_{1-8}$ alkoxy, and substituted $C_{1-8}$ alkoxy, wherein the each substituent of the substituted $C_{1-8}$ alkyl and $C_{1-8}$ alkoxy is independently selected from halogen, —$NO_2$, —OH, —COOH, —$NH_2$, —CN, —$CF_3$, —$OCF_3$.

In certain embodiments, each substituent is independently selected from halogen, —OH, —CN, —$CF_3$, =O, —$NO_2$, $C_{1-3}$ alkoxy, $C_{1-3}$ alkyl, —$COOR^{10}$ wherein $R^{10}$ is chosen from hydrogen, $C_{1-3}$ alkyl, and —$NR^{11}{}_2$ wherein each $R^{11}$ is independently chosen from hydrogen and $C_{1-3}$ alkyl.

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. The "therapeutically effective amount" can vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance can be readily ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

Reference is now made in detail to certain embodiments of compounds, compositions, and methods. The disclosed embodiments are not intended to be limiting of the claims. To the contrary, the claims are intended to cover all alternatives, modifications, and equivalents.

Creatine Phosphate Analog Prodrugs

In certain embodiments, a creatine phosphate analog prodrug is a compound of Formula (I):

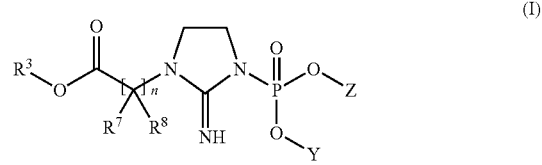

(I)

a pharmaceutically acceptable salt thereof, or a pharmaceutically acceptable solvate of any of the foregoing, wherein:

n is selected from 1 and 2;

Y and Z are independently selected from Formula (1), Formula (2), and Formula (3):

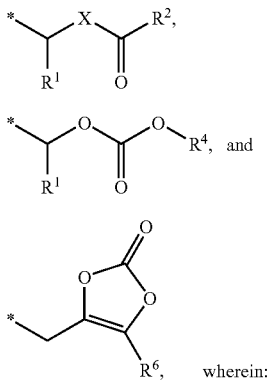

wherein:

each X is independently selected from O and S;
each $R^1$ and $R^2$ is independently selected from hydrogen, $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl;
each $R^4$ is independently selected from $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl; and
each $R^6$ is independently selected from hydrogen, $C_{1-8}$ alkyl, substituted $C_{1-8}$ alkyl, $C_{5-12}$ cycloalkyl, substituted $C_{5-12}$ cycloalkyl, $C_{5-12}$ aryl, and $C_{5-12}$ substituted aryl;
$R^3$ is selected from hydrogen, $C_{1-8}$ alkyl, substituted $C_{1-8}$ alkyl, $C_{1-8}$ heteroalkyl, substituted $C_{1-8}$ heteroalkyl, $C_{5-12}$ cycloalkyl, substituted $C_{5-12}$ cycloalkyl, $C_{6-20}$ cycloalkylalkyl, substituted $C_{6-20}$ cycloalkylalkyl, $C_{6-20}$ heterocycloalkylalkyl, substituted $C_{6-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl; and
each $R^7$ and $R^8$ is independently selected from hydrogen, $C_{1-8}$ alkyl, and substituted $C_{1-8}$ alkyl.

In certain embodiments of a compound of Formula (I), each substituent group is independently selected from halogen, —$NO_2$, —OH, —COOH, —$NH_2$, —CN, —$CF_3$, —$OCF_3$, $C_{1-8}$ alkyl, substituted $C_{1-8}$ alkyl, $C_{1-8}$ alkoxy, and substituted $C_{1-8}$ alkoxy. In certain embodiments of a compound of Formula (I), each substituent is independently selected from halogen, —OH, —CN, —$CF_3$, =O, —$NO_2$, $C_{1-3}$ alkoxy, $C_{1-3}$ alkyl, —$COOR^{10}$ wherein $R^{10}$ is chosen from hydrogen, $C_{1-3}$ alkyl, and —$NR^{11}{}_2$ wherein each $R^{11}$ is independently chosen from hydrogen and $C_{1-3}$ alkyl.

In certain embodiments of a compound of Formula (I), n is 1.

In certain embodiments of a compound of Formula (I), n is 2.

In certain embodiments of a compound of Formula (I), each X is O.

In certain embodiments of a compound of Formula (I), each X is S.

In certain embodiments of a compound of Formula (I), each $R^1$ and $R^2$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl.

In certain embodiments of a compound of Formula (I), each $R^1$ is independently selected from hydrogen, methyl, ethyl, n-propyl, isopropyl, butyl, isobutyl, sec-butyl, tert-butyl, phenyl, and cyclohexyl.

In certain embodiments of a compound of Formula (I), each $R^2$ is independently selected from hydrogen, methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl.

In certain embodiments of a compound of Formula (I), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl.

In certain embodiments of a compound of Formula (I), each $R^4$ is independently selected from $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl.

In certain embodiments of a compound of Formula (I), each $R^4$ is independently selected from methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl.

In certain embodiments of a compound of Formula (I), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl.

In certain embodiments of a compound of Formula (I), each $R^7$ and $R^8$ is hydrogen.

In certain embodiments of a compound of Formula (I), $R^3$ is selected from hydrogen, benzyl, and $C_{1-4}$ alkyl.

In certain embodiments of a compound of Formula (I), $R^3$ is hydrogen.

In certain embodiments of a compound of Formula (I), each $R^6$ is independently selected from methyl, ethyl, n-propyl, isopropyl, tert-butyl, phenyl, and cyclohexyl.

In certain embodiments of a compound of Formula (I), each $R^6$ is methyl.

In certain embodiments of a compound of Formula (I), n is 1, and each $R^7$ and $R^8$ is independently selected from hydrogen, $C_{1-8}$ alkyl, and substituted $C_{1-8}$ alkyl.

In certain embodiments of a compound of Formula (I), n is 1, each $R^7$ and $R^8$ is independently selected from hydrogen, $C_{1-8}$ alkyl, and substituted $C_{1-8}$ alkyl, and $R^3$ is selected from hydrogen, benzyl, and $C_{1-4}$ alkyl, and in certain embodiments, $R^3$ is hydrogen.

In certain embodiments of a compound of Formula (I), n is 1, and each $R^7$ and $R^8$ is hydrogen.

In certain embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I), n is 2, and each $R^7$ and $R^8$ is independently selected from hydrogen, $C_{1-8}$ alkyl, and substituted $C_{1-8}$ alkyl.

In certain embodiments of a compound of Formula (I), n is 2, each $R^7$ and $R^8$ is independently selected from hydrogen, $C_{1-8}$ alkyl, and substituted $C_{1-8}$ alkyl, and $R^3$ is selected from hydrogen, benzyl, and $C_{1-4}$ alkyl, and in certain embodiments, $R^3$ is hydrogen.

In certain embodiments of a compound of Formula (I), n is 2, and each $R^7$ and $R^8$ is hydrogen.

In certain embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (1), each $R^1$ and $R^2$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, and each $R^2$ is independently selected from hydrogen, methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is independently selected from hydrogen, methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, and each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (1), each $R^1$ is hydrogen, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is methyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is ethyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is n-propyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is isopropyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is butyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is isobutyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is sec-butyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is tert-butyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is phenyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is cyclohexyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is hydrogen, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is methyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is ethyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is n-propyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is isopropyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is n-butyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is isobutyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is sec-butyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is tert-butyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is n-pentyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is isopentyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is sec-pentyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is neopentyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is 1,1-diethoxyethyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is phenyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is cyclohexyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is 3-pyridyl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (2), each $R^1$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, each $R^4$ is independently selected from $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl. In certain embodiments of a compound of Formula (I) wherein at least one Y is selected from Formula (2), each $R^1$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, each $R^4$ is independently selected from $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, and each $R^4$ is independently selected from methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is independently selected from methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, and each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (2), each $R^1$ is hydrogen, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is methyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is ethyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is n-propyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is isopropyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is n-butyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is isobutyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is sec-butyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is tert-butyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is phenyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is cyclohexyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 1, each $R^7$ and $R^8$ is hydrogen, $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is methyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is ethyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is n-propyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is isopropyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is n-butyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is isobutyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is sec-butyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is tert-butyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is n-pentyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, and 3-pyridyl, each $R^4$ is isopentyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is sec-pentyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is neopentyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is 1,1-diethoxyethyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is phenyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, and 3-pyridyl, each $R^4$ is cyclohexyl, and $R^3$ is selected from hydrogen, benzyl, and $C_{1-4}$ alkyl, and in certain embodiments, $R^3$ is hydrogen. In certain embodiments of a compound of Formula (I) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is 3-pyridyl, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I) wherein at least one of Y or Z is selected from Formula (3), each $R^6$ is independently selected from methyl, ethyl, n-propyl, isopropyl, tert-butyl, phenyl, and cyclohexyl, and $R^3$ is selected from hydrogen, benzyl, and $C_{1-4}$ alkyl. In certain embodiments of a compound of Formula (I) wherein at least one of Y or Z is selected from Formula (3), each $R^6$ is independently selected from methyl, ethyl, n-propyl, isopropyl, tert-butyl, phenyl, and cyclohexyl, and $R^3$ is hydrogen. In certain embodiments of a compound of Formula (I) wherein at least one of Y or Z is selected from Formula (3), each $R^6$ is methyl, and $R^3$ is selected from hydrogen, benzyl, and $C_{1-4}$ alkyl. In certain embodiments of a compound of Formula (I) wherein at least one of Y or Z is selected from Formula (3), each $R^6$ is methyl, and $R^3$ is hydrogen. In certain of the immediately preceding embodiments of a compound of Formula (I), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (I), Y is selected from Formula (1) and Z is selected from Formula (3). In certain embodiments of a compound of Formula (I), Y is selected from Formula (2) and Z is selected from Formula (3). In certain embodiments of a compound of Formula (I), Y is selected from Formula (3) and Z is selected from Formula (1). In certain embodiments of a compound of Formula (I), Y is selected from Formula (3) and Z is selected from Formula (2).

In certain embodiments of a compound of Formula (I), each of Y and Z is selected from Formula (1).

In certain embodiments of a compound of Formula (I) wherein each of Y and Z is selected from Formula (1), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is selected from hydrogen, benzyl, and $C_{1-4}$ alkyl, n is 1, and $R^7$ and $R^8$ are independently selected from hydrogen, $C_{1-6}$ alkyl, and substituted $C_{1-6}$ alkyl. In certain embodiments of a compound of Formula (I) wherein each of Y and Z is selected from Formula (1), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is selected from hydrogen, benzyl, and $C_{1-4}$ alkyl, n is 2, and each $R^7$ and $R^8$ is independently selected from hydrogen, $C_{1-6}$ alkyl, and substituted $C_{1-6}$ alkyl. In certain embodiments of a compound of Formula (I) wherein each of Y and Z is selected from Formula (1), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is hydrogen, n is 1, and each of $R^7$ and $R^8$ is hydrogen. In certain embodiments of a compound of Formula (I) wherein each of Y and Z is selected from Formula (1), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is hydrogen, n is 2, and each $R^7$ and $R^8$ is hydrogen. In certain of the immediately preceding embodiments, each X is O, in certain of the immediately preceding embodiments, each X is S, and in certain of the immediately preceding embodiments, one X is O and the other X is S.

In certain embodiments of a compound of Formula (I), each of Y and Z is selected from Formula (2).

In certain embodiments of a compound of Formula (I) wherein each of Y and Z is selected from Formula (2), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is selected from hydrogen, benzyl, and $C_{1-4}$ alkyl, n is 1, and $R^7$ and $R^8$ are independently selected from hydrogen, $C_{1-8}$ alkyl, and substituted $C_{1-8}$ alkyl.

In certain embodiments of a compound of Formula (I) wherein each of Y and Z is selected from Formula (2), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is selected from hydrogen, benzyl, and $C_{1-4}$ alkyl, n is 2, and each $R^7$ and $R^8$ is independently selected from hydrogen, $C_{1-6}$ alkyl, and substituted $C_{1-6}$ alkyl.

In certain embodiments of a compound of Formula (I) wherein each of Y and Z is selected from Formula (2), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is hydrogen, n is 1, and each of $R^7$ and $R^8$ is hydrogen, and $C_{1-4}$ alkyl.

In certain embodiments of a compound of Formula (I) wherein each of Y and Z is selected from Formula (2), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is hydrogen, n is 2, and each $R^7$ and $R^8$ is hydrogen, and $C_{1-4}$ alkyl.

In certain embodiments of a compound of Formula (I), each of Y and Z is selected from Formula (3).

In certain embodiments of a compound of Formula (I) wherein each of Y and Z is selected from Formula (3), each $R^6$ is independently selected from methyl, ethyl, n-propyl, isopropyl, tert-butyl, phenyl, and cyclohexyl, $R^3$ is selected from hydrogen, benzyl, and $C_{1-4}$ alkyl, n is 1, and $R^7$ and $R^8$ are independently selected from hydrogen, $C_{1-8}$ alkyl, and substituted $C_{1-8}$ alkyl.

In certain embodiments of a compound of Formula (I) wherein each of Y and Z is selected from Formula (3), each $R^6$ is independently selected from methyl, ethyl, n-propyl, isopropyl, tert-butyl, phenyl, and cyclohexyl, $R^3$ is selected from hydrogen, benzyl, and $C_{1-4}$ alkyl, n is 2, and each $R^7$ and $R^8$ is independently selected from hydrogen, $C_{1-8}$ alkyl, and substituted $C_{1-8}$ alkyl.

In certain embodiments of a compound of Formula (I) wherein each of Y and Z is selected from Formula (3), each $R^6$ is methyl, $R^3$ is hydrogen, n is 1, and each of $R^7$ and $R^8$ is hydrogen.

In certain embodiments of a compound of Formula (I) wherein each of Y and Z is selected from Formula (3), each $R^6$ is methyl, $R^3$ is hydrogen, n is 2, and each $R^7$ and $R^8$ is hydrogen.

In certain embodiments, a creatine phosphate analog prodrug is a compound of Formula (II):

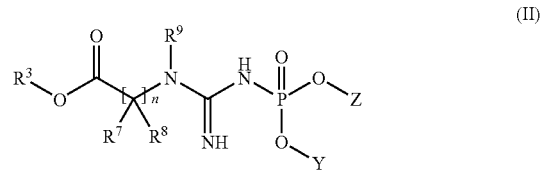

a pharmaceutically acceptable salt thereof, or a pharmaceutically acceptable solvate of any of the foregoing, wherein:

n is selected from 1 and 2;

Y and Z are independently selected from Formula (1), Formula (2), and Formula (3):

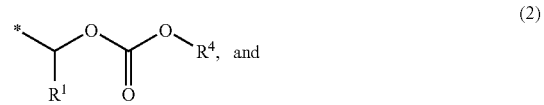

each X is independently selected from O and S;

each $R^1$ and $R^2$ is independently selected from hydrogen, $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl;

each $R^4$ is independently selected from $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl; and each $R^6$ is independently selected from hydrogen, $C_{1-8}$ alkyl, substituted $C_{1-8}$ alkyl, $C_{5-12}$ cycloalkyl, substituted $C_{5-12}$ cycloalkyl, $C_{5-12}$ aryl, and $C_{5-12}$ substituted aryl;

$R^3$ is selected from hydrogen, $C_{1-8}$ alkyl, substituted $C_{1-8}$ alkyl, $C_{1-8}$ heteroalkyl, substituted $C_{1-8}$ heteroalkyl, $C_{5-12}$ cycloalkyl, substituted $C_{5-12}$ cycloalkyl, $C_{6-20}$ cycloalkylalkyl, substituted $C_{6-20}$ cycloalkylalkyl, $C_{6-20}$ heterocycloalkylalkyl, substituted $C_{6-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl;

each $R^7$ and $R^8$ is independently selected from hydrogen, $C_{1-8}$ alkyl, and substituted $C_{1-8}$ alkyl; and $R^9$ is selected from hydrogen, $C_{1-8}$ alkyl, substituted $C_{1-8}$ alkyl, $C_{1-8}$ heteroalkyl, and substituted $C_{1-8}$ heteroalkyl.

In certain embodiments of a compound of Formula (II), each substituent group is independently selected from halogen, —$NO_2$, —OH, —COOH, —$NH_2$, —CN, —$CF_3$, —$OCF_3$, $C_{1-8}$ alkyl, substituted $C_{1-8}$ alkyl, $C_{1-8}$ alkoxy, and substituted $C_{1-8}$ alkoxy. In certain embodiments of a compound of Formula (II), each substituent is independently selected from halogen, —OH, —CN, —$CF_3$, =O, —$NO_2$, $C_{1-3}$ alkoxy, $C_{1-3}$ alkyl, —$COOR^{10}$ wherein $R^{10}$ is chosen from hydrogen, $C_{1-3}$ alkyl, and —$NR^{11}_2$ wherein each $R^{11}$ is independently chosen from hydrogen and $C_{1-3}$ alkyl.

In certain embodiments of a compound of Formula (II), n is 1.

In certain embodiments of a compound of Formula (II), n is 2.

In certain embodiments of a compound of Formula (II), each X is O.

In certain embodiments of a compound of Formula (II), each X is S.

In certain embodiments of a compound of Formula (II), each $R^1$ and $R^2$, is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl.

In certain embodiments of a compound of Formula (II), each $R^1$ is independently selected from hydrogen, methyl, ethyl, n-propyl, isopropyl, butyl, isobutyl, sec-butyl, tert-butyl, phenyl, and cyclohexyl.

In certain embodiments of a compound of Formula (II), each $R^2$ is independently selected from hydrogen, methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl.

In certain embodiments of a compound of Formula (II), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl.

In certain embodiments of a compound of Formula (II), each $R^4$ is independently selected from $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl.

In certain embodiments of a compound of Formula (II), each $R^4$ is independently selected from methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl.

In certain embodiments of a compound of Formula (II), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl.

In certain embodiments of a compound of Formula (II), $R^3$ is selected from hydrogen, benzyl, and $C_{1-4}$ alkyl.

In certain embodiments of a compound of Formula (II), $R^3$ is hydrogen.

In certain embodiments of a compound of Formula (II), each $R^6$ is independently selected from methyl, ethyl, n-propyl, isopropyl, tert-butyl, phenyl, and cyclohexyl.

In certain embodiments of a compound of Formula (II), each $R^6$ is methyl.

In certain embodiments of a compound of Formula (II), each $R^7$ and $R^8$ is hydrogen.

In certain embodiments of a compound of Formula (II), $R^9$ is selected from hydrogen and $C_{1-4}$ alkyl.

In certain embodiments of a compound of Formula (II), $R^9$ is hydrogen.

In certain embodiments of a compound of Formula (II), n is 1, and each $R^7$ and $R^8$ is independently selected from hydrogen, $C_{1-8}$ alkyl, and substituted $C_{1-8}$ alkyl. In certain embodiments of a compound of Formula (II), n is 1, each $R^7$ and $R^8$ is independently selected from hydrogen, $C_{1-4}$ alkyl, and substituted $C_{1-8}$ alkyl, and $R^3$ is selected from hydrogen, benzyl, and $C_{1-4}$ alkyl, and in certain embodiments, $R^3$ is hydrogen. In certain embodiments of a compound of Formula (II), n is 1 and each $R^7$ and $R^8$ is hydrogen. In certain embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II), n is 2, and each $R^7$ and $R^8$ is independently selected from hydrogen, $C_{1-8}$ alkyl, and substituted $C_{1-8}$ alkyl. In certain embodiments of a compound of Formula (II), n is 2, each $R^7$ and $R^8$ is independently selected from hydrogen, $C_{1-8}$ alkyl, and substituted $C_{1-8}$ alkyl, and $R^3$ is selected from hydrogen, benzyl, and $C_{1-4}$ alkyl, and in certain embodiments, $R^3$ is hydrogen. In certain embodiments of a compound of Formula (II), n is 2 and each $R^7$ and $R^8$ is hydrogen. In certain embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (1), each $R^1$ and $R^2$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (1), each $R^1$ and $R^2$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, and each $R^2$ is independently selected from hydrogen, methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is independently selected from hydrogen, methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, and each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (I), n is 2, each $R^7$ and $R^8$ is hydrogen, and $R^3$ is selected from hydrogen, benzyl, and $C_{1-4}$ alkyl, and in certain embodiments, $R^3$ is hydrogen.

In certain embodiments of a compound of Formula (II) wherein at least one of Y or Z is selected from Formula (1), each $R^1$ is hydrogen, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is methyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is ethyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is n-propyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is isopropyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is butyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is isobutyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is sec-butyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is tert-butyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is phenyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is cyclohexyl, each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is hydrogen, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is methyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is ethyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is n-propyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is isopropyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is n-butyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is isobutyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is sec-butyl, and $R^3$ is selected from hydrogen, benzyl, and $C_{1-4}$ alkyl, and in certain embodiments, $R^3$ is hydrogen.

In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is tert-butyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is n-pentyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is isopentyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is sec-pentyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is neopentyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is 1,1-diethoxyethyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is phenyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is cyclohexyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (1), each $R^1$ is independently selected from hydrogen, methyl, ethyl, n-propyl, isopropyl, butyl, isobutyl, sec-butyl, tert-butyl, phenyl, and cyclohexyl, each $R^2$ is 3-pyridyl, and $R^3$ is selected from hydrogen, benzyl, and $C_{1-4}$ alkyl, and in certain embodiments, $R^3$ is hydrogen. In certain of the immediately preceding embodiments, each X is O, and in certain of the immediately preceding embodiments, each X is S. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (2), each $R^1$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, each $R^4$ is independently selected from $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl. In certain embodiments of a compound of Formula (II) wherein at least one of Y or Z is selected from Formula (2), each $R^1$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, each $R^4$ is independently selected from $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, and each $R^4$ is independently selected from methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is independently selected from methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, and each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (2), each $R^1$ is hydrogen, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is methyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is ethyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is n-propyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is isopropyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is n-butyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is isobutyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is sec-butyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is tert-butyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen.

In certain embodiments of a compound of Formula (II) wherein at least one of Y or Z is selected from Formula (2), each $R^1$ is phenyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is cyclohexyl, each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is methyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is ethyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is n-propyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is isopropyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is n-butyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is isobutyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is sec-butyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is tert-butyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is n-pentyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is isopentyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is sec-pentyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is neopentyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is 1,1-diethoxyethyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is phenyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is cyclohexyl, and $R^3$ is selected from hydrogen, benzyl, and $C_{1-4}$ alkyl, and in certain embodiments, $R^3$ is hydrogen. In certain embodiments of a compound of Formula (II) wherein at least one of Y or Z is selected from Formula (2), each $R^1$ is independently selected from hydrogen, methyl, ethyl, n-propyl, isopropyl, butyl, isobutyl, sec-butyl, tert-butyl, phenyl, and cyclohexyl, each $R^4$ is 3-pyridyl, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (3), each $R^6$ is independently selected from methyl, ethyl, n-propyl, isopropyl, tert-butyl, phenyl, and cyclohexyl, and $R^3$ is selected from hydrogen, benzyl, and $C_{1-4}$ alkyl. In certain embodiments of a compound of Formula (II) wherein at least one of Y or Z is selected from Formula (3), each $R^6$ is independently selected from methyl, ethyl, n-propyl, isopropyl, tert-butyl, phenyl, and cyclohexyl, and $R^3$ is hydrogen. In certain embodiments of a compound of Formula (II) wherein at least one of Y or Z is selected from Formula (3), each $R^6$ is methyl, and $R^3$ is selected from hydrogen, benzyl, and $C_{1-4}$ alkyl. In certain embodiments of a compound of Formula (II) wherein at least one of Y or Z is selected from Formula (3), each $R^6$ is methyl, and $R^3$ is hydrogen. In certain of the immediately preceding embodiments of a compound of Formula (II), n is 1, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), n is 2, each $R^7$ and $R^8$ is hydrogen, and $R^3$ is selected from hydrogen, benzyl, and $C_{1-4}$ alkyl, and in certain embodiments, $R^3$ is hydrogen. In certain of the immediately preceding embodiments of a compound of Formula (II), $R^9$ is selected from hydrogen and $C_{1-4}$ alkyl, and in certain embodiments, $R^9$ is hydrogen.

In certain embodiments of a compound of Formula (II) wherein at least one of Y or Z is selected from Formula (3), n is 1, each $R^6$ is methyl, each of $R^3$, $R^7$, $R^8$, and $R^9$ is hydrogen.

In certain embodiments of a compound of Formula (II) wherein at least one of Y or Z is selected from Formula (3), n is 2, each $R^6$ is methyl, each of $R^3$, $R^7$, $R^8$, and $R^9$ is hydrogen.

In certain embodiments of a compound of Formula (II), Y is selected from Formula (1) and Z is selected from Formula (2). In certain embodiments of a compound of Formula (II), Y is selected from Formula (1) and Z is selected from Formula (3). In certain embodiments of a compound of Formula (II), Y is selected from Formula (2) and Z is selected from Formula (3).

In certain embodiments of a compound of Formula (II), each of Y and Z is selected from Formula (1). In certain embodiments of a compound of Formula (II) wherein each of Y and Z is selected from Formula (1), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is selected from hydrogen, benzyl, and $C_{1-4}$ alkyl, n is 1, $R^7$ and $R^8$ are independently selected from hydrogen, $C_{1-8}$ alkyl, and substituted $C_{1-8}$ alkyl, and $R^9$ is selected from hydrogen and $C_{1-4}$ alkyl. In certain embodiments of a compound of Formula (II) wherein each of Y and Z is selected from Formula (1), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is selected from hydrogen, benzyl, and $C_{1-4}$ alkyl, n is 2, each $R^7$ and $R^8$ is independently selected from hydrogen, $C_{1-8}$ alkyl, and substituted $C_{1-8}$ alkyl, and $R^9$ is selected from hydrogen and $C_{1-4}$ alkyl. In certain embodiments of a compound of Formula (II) wherein each of Y and Z is selected from Formula (1), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is hydrogen, n is 1, each of $R^7$ and $R^8$ is hydrogen, and $R^9$ is hydrogen. In certain embodiments of a compound of Formula (II) wherein each of Y and Z is selected from Formula (1), each $R^2$ is independently selected from hydrogen, methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is hydrogen, n is 2, each $R^7$ and $R^8$ is hydrogen, and $R^9$ is hydrogen. In certain of the immediately preceding embodiments, each X is O, in certain of the immediately preceding embodiments, each X is S, and in certain of the immediately preceding embodiments, one X is O and the other X is S.

In certain embodiments of a compound of Formula (II), each of Y and Z is selected from Formula (2).

In certain embodiments of a compound of Formula (II) wherein each of Y and Z is selected from Formula (2), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is selected from hydrogen, benzyl, and $C_{1-4}$ alkyl, n is 1, $R^7$ and $R^8$ are independently selected from hydrogen, $C_{1-8}$ alkyl, and substituted $C_{1-8}$ alkyl, and $R^9$ is selected from hydrogen and $C_{1-4}$ alkyl.

In certain embodiments of a compound of Formula (II) wherein each of Y and Z is selected from Formula (2), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is selected from hydrogen, benzyl, and $C_{1-4}$ alkyl, n is 2, each $R^7$ and $R^8$ is independently selected from hydrogen, $C_{1-8}$ alkyl, and substituted $C_{1-8}$ alkyl, and $R^9$ is selected from hydrogen and $C_{1-4}$ alkyl.

In certain embodiments of a compound of Formula (II) wherein each of Y and Z is selected from Formula (2), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is hydrogen, n is 1, each of $R^7$ and $R^8$ is hydrogen, and $C_{1-4}$ alkyl, and $R^9$ is hydrogen.

In certain embodiments of a compound of Formula (II) wherein each of Y and Z is selected from Formula (2), each $R^4$ is independently selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, each $R^1$ is independently selected from hydrogen, methyl, ethyl, n-propyl, isopropyl, butyl, isobutyl, sec-butyl, tert-butyl, phenyl, and cyclohexyl, $R^3$ is hydrogen, n is 2, each $R^7$ and $R^8$ is hydrogen, and $C_{1-4}$ alkyl, and $R^9$ is hydrogen.

In certain embodiments of a compound of Formula (II), each of Y and Z is selected from Formula (3).

In certain embodiments of a compound of Formula (II) wherein each of Y and Z is selected from Formula (3), each $R^6$ is independently selected from methyl, ethyl, n-propyl, isopropyl, tert-butyl, phenyl, and cyclohexyl, $R^3$ is selected from hydrogen, benzyl, and $C_{1-4}$ alkyl, n is 1, $R^7$ and $R^8$ are independently selected from hydrogen, $C_{1-6}$ alkyl, and substituted $C_{1-6}$ alkyl, and $R^9$ is selected from hydrogen and $C_{1-4}$ alkyl.

In certain embodiments of a compound of Formula (II) wherein each of Y and Z is selected from Formula (3), each $R^6$ is independently selected from methyl, ethyl, n-propyl, isopropyl, tert-butyl, phenyl, and cyclohexyl, $R^3$ is selected from hydrogen, benzyl, and $C_{1-4}$ alkyl, n is 2, each $R^7$ and $R^8$ is independently selected from hydrogen, $C_{1-8}$ alkyl, and substituted $C_{1-6}$ alkyl, and $R^9$ is selected from hydrogen and $C_{1-4}$ alkyl.

In certain embodiments of a compound of Formula (II) wherein each of Y and Z is selected from Formula (3), each $R^6$ is methyl, $R^3$ is hydrogen, n is 1, each of $R^7$ and $R^8$ is hydrogen, and $R^9$ is hydrogen.

In certain embodiments of a compound of Formula (II) wherein each of Y and Z is selected from Formula (3), each $R^6$ is methyl, $R^3$ is hydrogen, n is 2, each $R^7$ and $R^8$ is hydrogen, and $R^9$ is hydrogen.

The ability of compounds of Formula (I) and Formula (II) to effect intracellular energy homeostasis can be assessed in vitro by determining the ability of the prodrug of a creatine phosphate analog to restore energy homeostasis in cells following treatment with sodium azide (see, e.g., Weinstock and Shoham, *Neural Transm.* 2004, 111(3), 347-66). The ability of compounds of Formula (I) and Formula (II) to protect against challenge to cellular energy metabolism can be assessed in vitro by determining the viability of cells treated with a prodrug of a creatine phosphate analog followed by exposure to 3-nitropropionic acid (see, e.g., Brouillet et al., *J. Neurochem* 2005, 95(6), 1521-40).

Synthesis of Creatine Phosphate Analog Prodrugs

In certain embodiments, membrane permeable creatine phosphate analog prodrugs can include compounds in which the four charged groups of creatine phosphate or analog thereof are masked. Masking the charged groups with a cleavable moiety can provide a creatine phosphate analog prodrug with greater stability in biological fluids and with enhanced permeability through biological membranes than the corresponding parent compound, e.g., a creatine phosphate analog. Creatine phosphate contains three charged acidic groups with pKa values of 3.4, 5.0, and 1.5 as well as the basic guanidine nitrogen with a pKa of 12.5. The most acidic phosphate oxygen atom and the basic nitrogen are expected to be more than 99.999% charged at physiological pH, and therefore have very poor membrane permeability. As shown in FIG. 1, addition of cleavable ester moieties to the phosphate oxygen atoms not only masks the acidic oxygen atoms but is also predicted to dramatically shift the basic nitrogen pKa from 12.5 to −0.3. For example, the phosphate bis-protected compound 2 has only a single weak acidic group, and the cLogD is shifted from −7.8 to −2.1. Thus, as shown by compound 3, it is possible to further raise the cLogD to positive values by modifying the cleavable ester groups. Optimal creatine phosphate analog prodrugs can contain cleavable moieties having groups that result in a combination of chemical stability, enzymatic cleavability, low toxicity of breakdown products, and high membrane permeability.

Compounds of Formula (I) and Formula (II) may be obtained via the synthetic methods illustrated in Schemes 1-3. Those of ordinary skill in the art will appreciate that a preferred synthetic route to the disclosed compounds consists of attaching promoieties to a creatine phosphate analog. Methods of synthesizing analogs of creatine, creatine phosphate, creatine phosphate analogs, and cyclocreatine are known (see, e.g., Wang, *J Org Chem* 1974, 39, 3591-3594; Rowley et al., *J Am Chem Soc* 1971, 93, 5542-5551; Mclaughlin et al., *J Biol Chem* 1972, 247, 4382-4388; Nguyen, "Synthesis and enzyme studies using creatine analogues," Thesis, Dept. Pharmaceutical Chemistry, Univ. Calif. San Francisco (1983); Lowe et al., *J. Biol Chem* 1980, 225, 3944-51; Roberts et al., *J Biol Chem* 1995, 260, 13502-13508; Roberts et al., *Arch Biochem Biophy* 1983, 220, 563-571; Griffiths et al., *J Biol Chem* 1976, 251, 2049-2054; and Kaddurah-Daouk et al., PCT International Publication Nos. 2004/0054006, WO 92/08456 and WO 90/09192, and U.S. Pat. Nos. 5,324,731 and 5,321,030 6, each of which is incorporated by reference herein in its entirety). Creatine phosphate compounds can also be synthesized chemically or enzymatically (see e.g., Annesley et al., *Biochem Biophys Res Commun* 1977, 74, 185-190; Cramer et al., *A Chem Ber,* 1962, 95, 1670-1682; and Anatol, French Patent No. 75327, each of which is incorporated by reference herein in its entirety). Methods of synthesizing creatine esters are described in Miller et al., PCT International Application No. WO 2004/07146; Vennerstrom U.S. Pat. No. 6,897,334 and U.S. Published Application No. 2005/049428; Mold et al., *J. Am. Chem. Soc.* 1955, 77, 178-80, each of which is incorporated by reference herein in its entirety. Methods of synthesizing creatine phosphate analogs of Formula (II) are described in *Tetrahedron* 1997, 53(19), 6697-6705 and *Bioorganic & Medical Chemistry* 1998, 6, 1185-1208, each of which is incorporated by reference herein in its entirety.

General synthetic methods useful in the synthesis of the compounds described herein are available in the art (e.g., Wuts and Greene, "Protective Groups in Organic Synthesis," John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003).

Starting materials useful for preparing compounds and intermediates thereof, and/or practicing methods described herein are commercially available or can be prepared by well-known synthetic methods. Other methods for synthesis of the prodrugs described herein are either described in the art or will be readily apparent to one skilled in the art in view of the references provided above and may be used to synthesize the compounds described herein. Accordingly, the methods presented in the Schemes herein are illustrative rather than comprehensive.

In certain embodiments, compounds of Formula (I) can be synthesized according to general reaction Scheme 1:

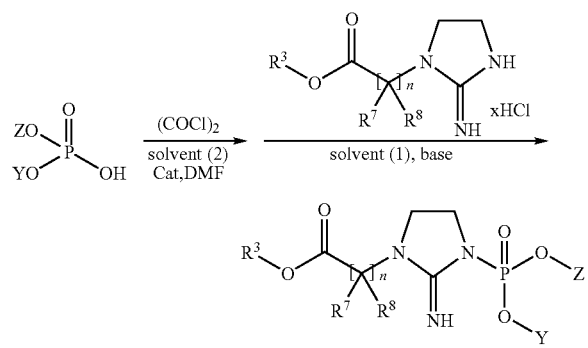

and compounds of Formula (II) can be synthesized according to general reaction Scheme 2:

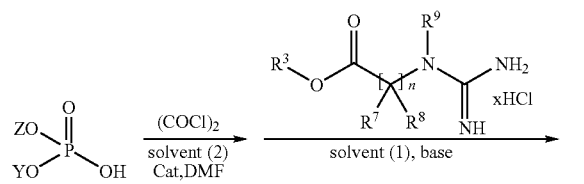

-continued

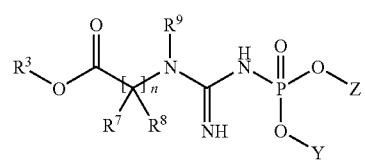

wherein n, Z, Y, $R^3$, $R^7$, $R^8$, and $R^9$ are as defined herein.

In certain embodiments of methods of Scheme 1 and Scheme 2, solvent (1) can be selected from, for example, acetone, acetonitrile, dichloromethane (DCM), dichloroethane, chloroform, toluene, tetrahydrofuran (THF), dioxane, dimethylformamide, dimethylacetamide, N-methylpyrrolidinone, pyridine, ethyl acetate, methyl tert-butyl ether, and combinations thereof. In certain embodiments, solvent (1) can be selected from dichloromethane and tetrahydrofuran.

In certain embodiments of methods of Scheme 1 and Scheme 2, solvent (2) can be selected from, for example, acetone, acetonitrile, dichloromethane (DCM), dichloroethane, chloroform, toluene, tetrahydrofuran (THF), dioxane, dimethylformamide, dimethylacetamide, N-methylpyrrolidinone, pyridine, ethyl acetate, methyl tert-butyl ether, and combinations thereof. In certain embodiments, solvent (2) can be selected from dichloromethane and tetrahydrofuran.

In certain embodiments of methods of Scheme 1 and Scheme 2, the base can be selected from, for example, triethylamine (TEA), diisopropylethylamine (DIEA), pyridine, 4-dimethylaminopyridine (DMAP), diethanolamine (DEA), and combinations thereof. In certain embodiments, the base can be selected from triethylamine, diisopropylethylamine, and 4-dimethylaminopyridine.

In certain embodiments, in addition to a base, a catalytic amount of a second base such as DMAP can be added to solvent (1).

In certain embodiments, compounds of Formula (I) in which $R^3$ is hydrogen can be synthesized from the corresponding creatine phosphate benzyl ester using the corresponding creatine analog benzyl ester according to Scheme 1 and Scheme 2 and hydrogenating the creatine phosphate analog benzyl ester as in Scheme 3 and Scheme 4:

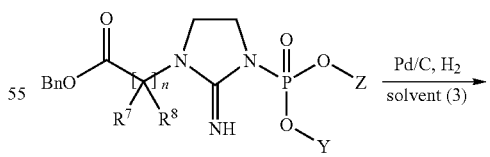

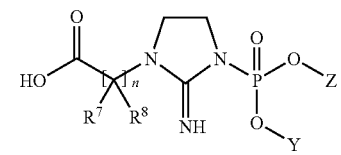

Scheme 4

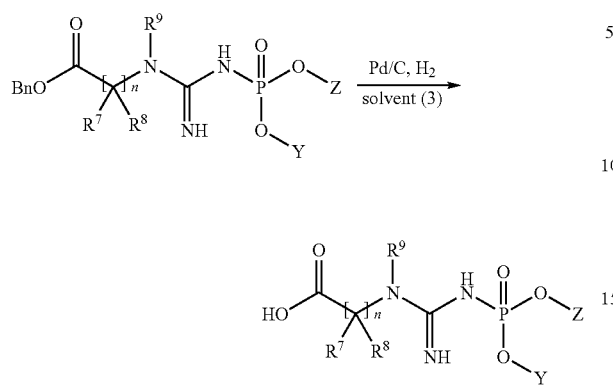

wherein n, Z, Y, $R^7$, $R^8$, and $R^9$ are as defined herein.

In certain embodiments of reaction Scheme 2 and Scheme 4, solvent (3) can be selected from, for example, methanol, ethanol, isopropanol, tert-butanol, ethylacetate, and combinations thereof. In certain embodiments, solvent (3) can be selected from methanol and ethanol.

The methods of Schemes 1-4 can be carried out at a temperature from about −20° C. to about 40° C. In certain embodiments, the temperature is from about 0° C. to about 40° C., in certain embodiments, from about 10° C. to about 30° C., and in certain embodiments, the temperature is about 25° C. (room temperature).

Mono- and di-substituted phosphoric acids can be prepared according to reaction Scheme 5:

Scheme 5

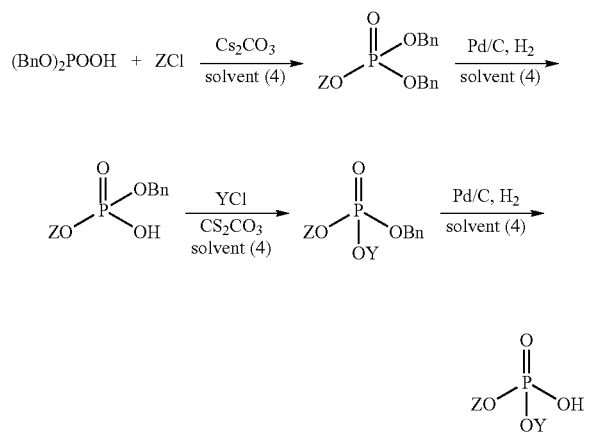

wherein Z and Y are as defined herein.

In certain embodiments of reaction Scheme 5, solvent (4) can be selected from, for example, methanol, ethanol, isopropanol, or tert-butanol, ethylacetate, acetone, and combinations thereof. In certain embodiments, solvent (4) can be selected from methanol, acetone, and a mixture thereof.

Compounds of Formula (II) in which n is 2 can be prepared according to reaction Scheme 6:

Scheme 6

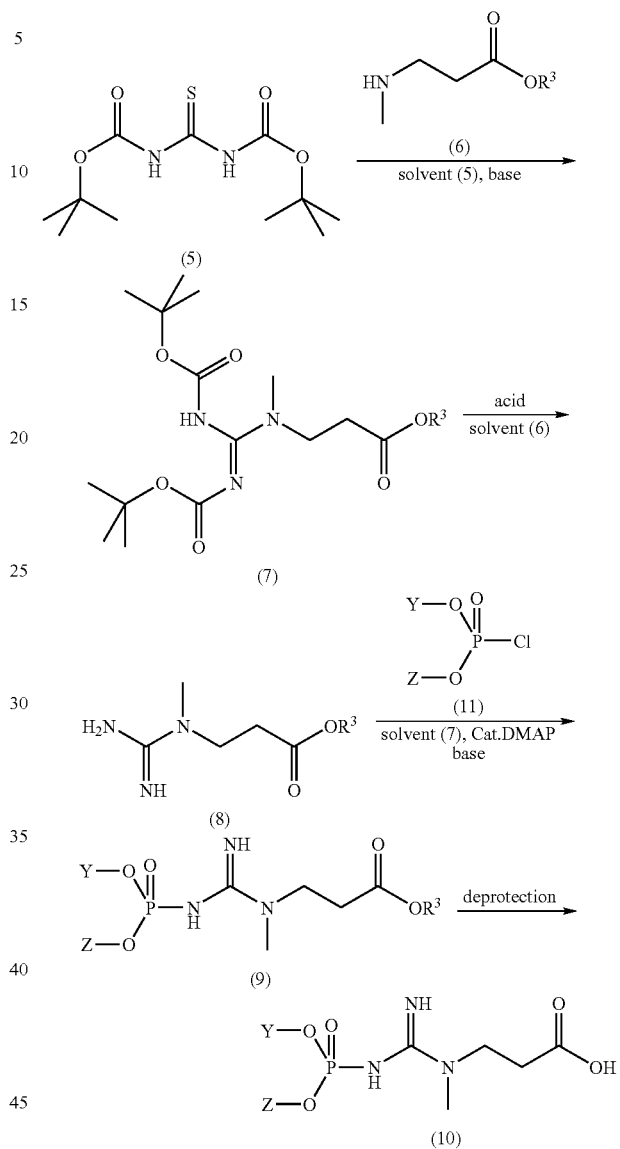

wherein Z, Y, and $R^3$ are as defined herein.

Compound (5) can be reacted with compound (6) in a solvent (5) such as N,N-dimethylformamide in the presence of a base such as triethylamine to provide compound (7). Compound (7) can then be reacted in a solvent (6) such as dichloromethane in the presence of an acid such as trifluoroacetic acid to provide compound (8). Compound (8) can be reacted with a mono- or di-substituted phosphorochloridic acid (11) in a solvent (7) such as dichloromethane in the presence of a base such as DEA and a catalytic amount of DMAP to provide creatine phosphate analog (9), which in certain embodiments, can be deprotected using a Pd/C catalyst in a solvent such as methanol, ethanol, isopropanol, tert-butanol, ethylacetate, acetone, or a combination thereof under a hydrogen atmosphere to provide creatine phosphate analog (10). Other creatine phosphate analogs of Formula (II) wherein n is 2 can be prepared by replacing compound (6) with compound (12):

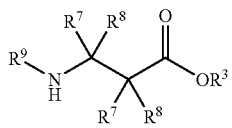

(12)

in reaction Scheme 6 wherein each $R^3$, $R^7$, $R^8$, and $R^9$ are as defined herein.

Pharmaceutical Compositions

Pharmaceutical compositions provided by the present disclosure can comprise a compound of Formula (I) and/or Formula (II) and a pharmaceutically acceptable vehicle. A pharmaceutical composition can comprise a therapeutically effective amount of compound of Formula (I) and/or Formula (II) and a pharmaceutically acceptable vehicle. In certain embodiments, a pharmaceutical composition can include more than one compound of Formula (I) and/or Formula (II). Pharmaceutically acceptable vehicles include diluents, adjuvants, excipients, and carriers.

Pharmaceutical compositions can be produced using standard procedures (see, e.g., "Remington's The Science and Practice of Pharmacy," 21st edition, Lippincott, Williams & Wilcox, 2005). Pharmaceutical compositions may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds disclosed herein into preparations, which can be used pharmaceutically. Proper formulation can depend, in part, on the route of administration Pharmaceutical compositions provided by the present disclosure can provide therapeutic plasma concentrations of a creatine phosphate analog upon administration to a patient. The promoiety of a creatine phosphate analog prodrug can be cleaved in vivo either chemically and/or enzymatically to release the corresponding creatine phosphate analog. One or more enzymes present in the intestinal lumen, intestinal tissue, blood, liver, brain, or any other suitable tissue of a mammal can enzymatically cleave the promoiety of the administered prodrugs. For example, the promoiety can be cleaved after absorption by the gastrointestinal tract (e.g., in intestinal tissue, blood, liver, or other suitable tissue of a mammal). In certain embodiments, a creatine phosphate analog remains conjugated to the promoiety during transit across the intestinal mucosal barrier to provide protection from presystemic metabolism. In certain embodiments, a creatine phosphate analog prodrug is essentially not metabolized to release the corresponding creatine phosphate analog within enterocytes, but is metabolized to the parent drug within the systemic circulation. Cleavage of the promoiety of a creatine phosphate analog prodrug after absorption by the gastrointestinal tract may allow the prodrug to be absorbed into the systemic circulation either by active transport, passive diffusion, or by a combination of both active and passive processes.

Creatine phosphate analog prodrugs can remain intact until after passage of the prodrug through a biological barrier, such as the blood-brain barrier. In certain embodiments, prodrugs provided by the present disclosure can be partially cleaved, e.g., one or more, but not all, of the promoieties can be cleaved before passage through a biological barrier or prior to being taken up by a cell, tissue, or organ.

Creatine phosphate analog prodrugs can remain intact in the systemic circulation and be absorbed by cells of an organ, either passively or by active transport mechanisms. In certain embodiments, a creatine phosphate analog prodrug will be lipophilic and can passively translocate through cellular membranes. Following cellular uptake, the prodrug can be cleaved chemically and/or enzymatically to release the corresponding creatine phosphate analog into the cellular cytoplasm, resulting in an increase in the intracellular concentration of the creatine phosphate analog. In certain embodiments, a prodrug can be permeable to intracellular membranes such as the mitochondrial membrane, and thereby facilitate delivery of a prodrug, and following cleavage of the promoiety or promoieties, a creatine phosphate analog, to an intracellular organelle such as mitochondria.

In certain embodiments, a pharmaceutical composition can include an adjuvant that facilitates absorption of a compound of Formula (I) and/or Formula (II) through the gastrointestinal epithelia. Such enhancers can, for example, open the tight-junctions in the gastrointestinal tract or modify the effect of cellular components, such as p-glycoprotein and the like. Suitable enhancers can include alkali metal salts of salicylic acid, such as sodium salicylate, caprylic or capric acid, such as sodium caprylate or sodium caprate, and the like. Enhancers can include, for example, bile salts, such as sodium deoxycholate. Various p-glycoprotein modulators are described in Fukazawa et al., U.S. Pat. No. 5,112,817 and Pfister et al., U.S. Pat. No. 5,643,909. Various absorption enhancing compounds and materials are described in Burnside et al., U.S. Pat. No. 5,824,638, and Meezam et al., U.S. Application Publication No. 2006/0046962. Other adjuvants that enhance permeability of cellular membranes include resorcinol, surfactants, polyethylene glycol, and bile acids.

In certain embodiments, a pharmaceutical composition can include an adjuvant that reduces enzymatic degradation of a compound of Formula (I) and/or Formula (II). Microencapsulation using protenoid microspheres, liposomes, or polysaccharides can also be effective in reducing enzymatic degradation of administered compounds.

A pharmaceutical composition can also include one or more pharmaceutically acceptable vehicles, including excipients, adjuvants, carriers, diluents, binders, lubricants, disintegrants, colorants, stabilizers, surfactants, fillers, buffers, thickeners, emulsifiers, wetting agents, and the like. Vehicles can be selected to alter the porosity and permeability of a pharmaceutical composition, alter hydration and disintegration properties, control hydration, enhance manufacturability, etc.

In certain embodiments, a pharmaceutical composition can be formulated for oral administration. Pharmaceutical compositions formulated for oral administration can provide for uptake of a compound of Formula (I) and/or Formula (II) throughout the gastrointestinal tract, or in a particular region or regions of the gastrointestinal tract. In certain embodiments, a pharmaceutical composition can be formulated to enhance uptake a compound of Formula (I) and/or Formula (II) from the upper gastrointestinal tract, and in certain embodiments, from the small intestine. Such compositions can be prepared in a manner known in the pharmaceutical art and can further comprise, in addition to a compound of Formula (I) and/or Formula (II), one or more pharmaceutically acceptable vehicles, permeability enhancers, and/or a second therapeutic agent.

In certain embodiments, a pharmaceutical composition can further comprise a substance to enhance, modulate and/or control release, bioavailability, therapeutic efficacy, therapeutic potency, stability, and the like. For example, to enhance therapeutic efficacy a compound of Formula (I) and/or Formula (II) can be co-administered with one or more active agents to increase the absorption or diffusion of the drug from the gastrointestinal tract, or to inhibit degradation of the drug in the systemic circulation. In certain embodiments, a compound of Formula (I) and/or Formula (II) can be co-administered with active agents having pharmacological effects that enhance the therapeutic efficacy of the compound of Formula (I) and/or Formula (II).

In certain embodiments, a pharmaceutical composition can further comprise substances to enhance, modulate and/or control release, bioavailability, therapeutic efficacy, therapeutic potency, stability, and the like. For example, to enhance therapeutic efficacy a compound of Formula (I) and/or Formula (II) can be co-administered with one or more active agents to increase the absorption or diffusion of a compound of Formula (I) and/or Formula (II) from the gastrointestinal tract, or to inhibit degradation of the drug in the systemic circulation. In certain embodiments, a compound of Formula (I) and/or Formula (II) can be co-administered with active agents having pharmacological effects that enhance the therapeutic efficacy of a compound of Formula (I) and/or Formula (II).

Pharmaceutical compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. Such vehicles can be of pharmaceutical grade. For oral liquid preparations such as, for example, suspensions, elixirs, and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcamitines, and the like may be added.

When a compound of Formula (I) or Formula (II) is acidic, it may be included in any of the above-described formulations as the free acid, a pharmaceutically acceptable salt, a solvate, or a hydrate. Pharmaceutically acceptable salts substantially retain the activity of the free acid, may be prepared by reaction with bases, and tend to be more soluble in aqueous and other protic solvents than the corresponding free acid form. In some embodiments, sodium salts of a compound of Formula (I) or Formula (II) are used in the above-described formulations.

Pharmaceutical compositions provided by the present disclosure can formulated for parenteral administration including administration by injection, for example, into a vein (intravenously), an artery (intraarterially), a muscle (intramuscularly), under the skin (subcutaneously or in a depot formulation), to the pericardium, to the coronary arteries, or used as a solution for delivery to a tissue or organ, for example, use in a cardiopulmonary bypass machine or to bathe transplant tissues or organs. Injectable compositions can be pharmaceutical compositions for any route of injectable administration, including, but not limited to, intravenous, intraarterial, intracoronary, pericardial, perivascular, intramuscular, subcutaneous, intradermal, intraperitoneal, and intraarticular. In certain embodiments, an injectable pharmaceutical composition can be a pharmaceutically appropriate composition for administration directly into the heart, pericardium or coronary arteries.

Pharmaceutical compositions provided by the present disclosure suitable for parenteral administration can comprise one or more compounds of Formula (I) or Formula (II) in combination with one or more pharmaceutically acceptable sterile isotonic aqueous, water-miscible, or non-aqueous vehicles. Pharmaceutical compositions for parenteral use may include substances that increase and maintain drug solubility such as complexing agents and surface acting agents, compounds that make the solution isotonic or near physiological pH such as sodium chloride, dextrose, and glycerin, substances that enhance the chemical stability of a solution such as antioxidants, inert gases, chelating agents, and buffers, substances that enhance the chemical and physical stability, substances that minimize self aggregation or interfacial induced aggregation, substances that minimize protein interaction with interfaces, preservatives including antimicrobial agents, suspending agents, emulsifying agents, and combinations of any of the foregoing. Pharmaceutical compositions for parenteral administration can be formulated as solutions, suspensions, emulsions, liposomes, microspheres, nanosystems, and powder to be reconstituted as solutions. Parenteral preparations are described in "Remington, The Science and Practice of Pharmacy," 21st edition, Lippincott, Williams & Wilkins, Chapter 41-42, pages 802-849, 2005.

In certain embodiments a pharmaceutical composition can be formulated for bathing transplantation tissue or organs before, during, or after transit to an intended recipient. Such compositions can be used before or during preparation of a tissue or organ for transplant. In certain embodiments, a pharmaceutical composition can be a cardioplegic solution administered during cardiac surgery. In certain embodiments, a pharmaceutical composition can be used, for example, in conjunction with a cardiopulmonary bypass machine to provide the pharmaceutical composition to the heart. Such pharmaceutical compositions can be used during the induction, maintenance, or reperfusion stages of cardiac surgery (see e.g., Chang et al., *Masui* 2003, 52(4), 356-62; Ibrahim et al., *Eur. J. Cardiothorac Surg* 1999, 15(1), 75-83; von Oppell et al., *J Thorac Cardiovasc Surg.* 1991, 102(3), 405-12; and Ji et al., *J. Extra Corpor Technol* 2002, 34(2), 107-10). In certain embodiments, a pharmaceutical composition can be delivered via a mechanical device such as a pump or perfuser (see e.g., Hou and March, *J Invasive Cardiol* 2003, 15(1), 13-7; Maisch et al., *Am. J. Cardiol* 2001, 88(11), 1323-6; and Macris and Igo, *Clin Cardiol* 1999, 22(1, Suppl 1), 136-9).

For prolonged delivery, a pharmaceutical composition can be provided as a depot preparation, for administration by implantation, e.g., subcutaneous, intradermal, or intramuscular injection. Thus, in certain embodiments, a pharmaceutical composition can be formulated with suitable polymeric or hydrophobic materials, e.g., as an emulsion in a pharmaceutically acceptable oil, ion exchange resins, or as a sparingly soluble derivative, e.g., as a sparingly soluble salt form of a compound of Formula (I) and Formula (II).

Pharmaceutical compositions provided by the present disclosure can be formulated so as to provide immediate, sustained, or delayed release of a compound of Formula (I) and/or Formula (II) after administration to the patient by employing procedures known in the art (see, e.g., Allen et al., "Ansel's Pharmaceutical Dosage Forms and Drug Delivery Systems," 8th ed., Lippincott, Williams & Wilkins, August 2004).

Dosage Forms

Pharmaceutical compositions provided by the present disclosure can be formulated in a unit dosage form. Unit dosage form refers to a physically discrete unit suitable as a unitary dose for patients undergoing treatment, with each unit containing a predetermined quantity of a compound of Formula (I) and/or Formula (II) calculated to produce an intended therapeutic effect. A unit dosage form can be for a single daily dose or one of multiple daily doses, e.g., 2 to 4 times per day. When multiple daily doses are used, the unit dosage can be the same or different for each dose. One or more dosage forms can comprise a dose, which may be administered to a patient at a single point in time or during a time interval.

Pharmaceutical compositions provided by the present disclosure can be used in dosage forms that provide immediate release and/or controlled release of a compound of Formula (I) and/or Formula (II). The appropriate type of dosage form can depend on the disease, disorder, or condition being treated, and on the method of administration. For example, for the treatment of acute ischemic conditions such as cardiac failure or stroke the use of an immediate release pharmaceutical composition or dosage form administered parenterally may be appropriate. For treatment of chronic neurodegenerative disorders, controlled release pharmaceutical composition or dosage form administered orally may be appropriate.

In certain embodiments, a dosage form can be adapted to be administered to a patient no more than twice per day, and in certain embodiments, only once per day. Dosing may be provided alone or in combination with other drugs and may continue as long as required for effective treatment of the disease, disorder, or condition.

Pharmaceutical compositions comprising a compound of Formula (I) and/or Formula (II) can be formulated for immediate release for parenteral administration, oral administration, or by any other appropriate route of administration.

Controlled drug delivery systems can be designed to deliver a drug in such a way that the drug level is maintained within the therapeutic windows and effective and safe blood levels are maintained for a period as long as the system continues to deliver the drug at a particular rate. Controlled drug delivery can produce substantially constant blood levels of a drug as compared to fluctuations observed with immediate release dosage forms. For some drugs, maintaining a constant bloodstream and tissue concentration throughout the course of therapy is the most desirable mode of treatment. Immediate release of these drugs can cause blood levels to peak above the level required to elicit the desired response, which wastes the drug and may cause or exacerbate toxic side effects. Controlled drug delivery can result in optimum therapy, and not only can reduce the frequency of dosing, and may also reduce the severity of side effects. Examples of controlled release dosage forms include dissolution controlled systems, diffusion controlled systems, ion exchange resins, osmotically controlled systems, erodible matrix systems, pH independent formulations, gastric retention systems, and the like.

In certain embodiments, an oral dosage form provided by the present disclosure can be a controlled release dosage form. Controlled delivery technologies can improve the absorption of a drug in a particular region or regions of the gastrointestinal tract. The appropriate oral dosage form for a particular pharmaceutical composition provided by the present disclosure can depend, at least in part, on the gastrointestinal absorption properties of the compound of Formula (I) or Formula (II), the stability of the compound of Formula (I) or Formula (II) in the gastrointestinal tract, the pharmacokinetics of the compound of Formula (I) or Formula (II), and the intended therapeutic profile. An appropriate controlled release oral dosage form can be selected for a particular the compound of Formula (I) or Formula (II). For example, gastric retention oral dosage forms can be appropriate for compounds absorbed primarily from the upper gastrointestinal tract, and sustained release oral dosage forms can be appropriate for compounds absorbed primarily form the lower gastrointestinal tract.

Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect. Gastric retention dosage forms, i.e., dosage forms that are designed to be retained in the stomach for a prolonged period of time, can increase the bioavailability of drugs that are most readily absorbed by the upper gastrointestinal tract. The residence time of a conventional dosage form in the stomach is 1 to 3 hours. After transiting the stomach, there is approximately a 3 to 5 hour window of bioavailability before the dosage form reaches the colon. However, if the dosage form is retained in the stomach, the drug can be released before it reaches the small intestine and will enter the intestine in solution in a state in which it can be more readily absorbed. Another use of gastric retention dosage forms is to improve the bioavailability of a drug that is unstable to the basic conditions of the intestine (see, e.g., Hwang et al., *Critical Reviews in Therapeutic Drug Carrier Systems*, 1998, 15, 243-284). To enhance drug absorption from the upper gastrointestinal tract, several gastric retention dosage forms have been developed. Examples include, hydrogels (see, e.g., Gutierrez-Rocca et al., U.S. Application Publication No. 2003/0008007), buoyant matrices (see, e.g., Lohray et al., Application Publication No. 2006/0013876), polymer sheets (see, e.g., Mohammad, Application Publication No. 2005/0249798), microcellular foams (see, e.g., Clarke et al., Application Publication No. 2005/0202090), and swellable dosage forms (see, e.g., Edgren et al., U.S. Application Publication No. 2005/0019409; Edgren et al., U.S. Pat. No. 6,797,283; Jacob et al., U.S. Application Publication No. 2006/0045865; Ayres, U.S. Application Publication No. 2004/0219186; Gusler et al., U.S. Pat. No. 6,723,340; Flashner-Barak et al., U.S. Pat. No. 6,476,006; Wong et al., U.S. Pat. Nos. 6,120,803 and 6,548,083; Shell et al., U.S. Pat. No. 6,635,280; and Conte et al., U.S. Pat. No. 5,780,057). Bioadhesive polymers can also provide a vehicle for controlled delivery of drugs to a number of mucosal surfaces in addition to the gastric mucosa (see, e.g., Mathiowitz et al., U.S. Pat. No. 6,235,313; Illum et al., U.S. Pat. No. 6,207,197; and Jacob et al., U.S. Application Publication Nos. 2006/0045865 and 2005/0064027). Ion exchange resins have been shown to prolong gastric retention, potentially by adhesion.

In a swelling and expanding system, dosage forms that swell and change density in relation to the surrounding gastric content can be retained in the stomach for longer than a conventional dosage form. A dosage form can absorb water and swell to form a gelatinous outside surface and float on the surface of gastric content surface while maintaining integrity before releasing a drug. Fatty materials can be added to impede wetting and enhance flotation when hydration and swelling alone are insufficient. Materials that release gases may also be incorporated to reduce the density of a gastric retention dosage form. Swelling also can significantly increase the size of a dosage form and thereby impede discharge of the non-disintegrated swollen solid dosage form through the pylorus into the small intestine. Swellable dosage forms can be formed by encapsulating a core containing drug and a swelling agent, or by combining a drug, swelling agent, and one or more erodible polymers.

Gastric retention dosage forms can also be in the form of a folded thin sheet containing a drug and water-insoluble diffusible polymer that opens in the stomach to its original size and shape, which is sufficiently large to prevent or inhibit passage of the expanded dosage from through the pyloric sphincter.

Floating and buoyancy gastric retention dosage forms can be designed to trap gases within sealed encapsulated cores that can float on the gastric contents, and thereby be retained in the stomach for a longer time, e.g., 9 to 12 hours. Due to the buoyancy effect, these systems can provide a protective layer preventing the reflux of gastric content into the esophageal region and can also be used for controlled release devices. A floating system can, for example, contain hollow cores containing drug coated with a protective membrane. The trapped air in the cores floats the dosage from on the gastric content until the soluble ingredients are released and the system collapses. In other floating systems, cores contain drug and chemical substances capable of generating gases when activated. For example, coated cores, containing carbonate and/or bicarbonate can generate carbon dioxide in the reaction with hydrochloric acid in the stomach or incorporated organic acid in the system. The gas generated by the reaction is retained to float the dosage form. The inflated dosage form later collapses and clears form the stomach when the generated gas permeates slowly through the protective coating.

Bioadhesive polymers can also provide a vehicle for controlled delivery of drugs to a number of mucosal surfaces in addition to the gastric mucosa (see, e.g., Mathiowitz et al., U.S. Pat. No. 6,235,313; and Illum et al., U.S. Pat. No. 6,207,197). A bioadhesive system can be designed by incorporation of a drug and other excipients within a bioadhesive polymer. On ingestion, the polymer hydrates and adheres to the mucus membrane of the gastrointestinal tract. Bioadhesive polymers can be selected that adhere to a desired region or regions of the gastrointestinal tract. Bioadhesive polymers can be selected to optimized delivery to targeted regions of the gastrointestinal tract including the stomach and small intestine. The mechanism of the adhesion is thought to be through the formation of electrostatic and hydrogen bonding at the polymer-mucus boundary. Jacob et al., U.S. Application Publication Nos. 2006/0045865 and 2005/0064027 disclose bioadhesive delivery systems which are useful for drug delivery to both the upper and lower gastrointestinal tract.

Ion exchange resins have been shown to prolong gastric retention, potentially by adhesion.

Gastric retention oral dosage forms can be appropriately used for delivery of drugs that are absorbed mainly from the upper gastrointestinal tract. For example, certain compounds of Formula (I) and Formula (II) may exhibit limited colonic absorption, and be absorbed primarily from the upper gastrointestinal tract. Thus, dosage forms that release the compound of Formula (I) and/or Formula (II) in the upper gastrointestinal tract and/or retard transit of the dosage form through the upper gastrointestinal tract will tend to enhance the oral bioavailability of the compound of Formula (I) and/or Formula (II). Other forms of creatine phosphate analogs disclosed herein can be appropriately used with gastric retention dosage forms.

Polymer matrices have also been used to achieve controlled release of the drug over a prolonged period of time. Such sustained or controlled release can be achieved by limiting the rate by which the surrounding gastric fluid can diffuse through the matrix and reach the drug, dissolve the drug and diffuse out again with the dissolved drug, or by using a matrix that slowly erodes, continuously exposing fresh drug to the surrounding fluid. Disclosures of polymer matrices that function by these methods are found, for example, in Skinner, U.S. Pat. Nos. 6,210,710 and 6,217,903; Rencher et al., U.S. Pat. No. 5,451,409; Kim, U.S. Pat. No. 5,945,125; Kim, PCT International Publication No. WO 96/26718; Ayer et al., U.S. Pat. No. 4,915,952; Akhtar et al., U.S. Pat. No. 5,328,942; Fassihi et al., U.S. Pat. No. 5,783,212; Wong et al., U.S. Pat. No. 6,120,803; and Pillay et al., U.S. Pat. No. 6,090,411.

Other drug delivery devices that remain in the stomach for extended periods of time include, for example, hydrogel reservoirs containing particles (Edgren et al., U.S. Pat. No. 4,871,548); swellable hydroxypropylmethylcellulose polymers (Edgren et al., U.S. Pat. No. 4,871,548); planar bioerodible polymers (Caldwell et al., U.S. Pat. No. 4,767,627); plurality of compressible retention arms (Curatolo et al., U.S. Pat. No. 5,443,843); hydrophilic water-swellable, cross-linked polymer particles (Shell, U.S. Pat. No. 5,007,790); and albumin-cross-linked polyvinylpyrrolidone hydrogels (Park et al., *J. Controlled Release* 1992, 19, 131-134).

In certain embodiments, pharmaceutical compositions provided by the present disclosure can be practiced with a number of different dosage forms, which can be adapted to provide sustained release of the compound of Formula (I) and/or Formula (II) upon oral administration. Sustained release oral dosage forms can be used to release drugs over a prolonged time period and are useful when it is desired that a drug or drug form be delivered to the lower gastrointestinal tract. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art (see, for example, "Remington's Pharmaceutical Sciences," Lippincott, Williams & Wilkins, 21st edition, 2005, Chapters 46 and 47; Langer, *Science* 1990, 249, 1527-1533; and Rosoff, "Controlled Release of Drugs," 1989, Chapter 2).

Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art (see, for example, "Remington's: The Science and Practice of Pharmacy," Lippincott, Williams & Wilkins, 21st edition, 2005, Chapters 46 and 47; Langer, *Science* 1990, 249, 1527-1533; and Rosoff, "Controlled Release of Drugs," 1989, Chapter 2).

In diffusion-controlled systems, a water-insoluble polymer controls the flow of fluid and the subsequent egress of dissolved drug from the dosage form. Both diffusional and dissolution processes are involved in release of drug from the dosage form. In reservoir devices, a core comprising a drug is coated with the polymer, and in matrix systems, the drug is dispersed throughout the matrix. Cellulose polymers such as ethylcellulose or cellulose acetate can be used in reservoir devices. Examples of materials useful in matrix systems include methacrylates, acrylates, polyethylene, acrylic acid copolymers, polyvinylchloride, high molecular weight polyvinylalcohols, cellulose derivates, and fatty compounds such as fatty acids, glycerides, and carnauba wax.

In dissolution-controlled systems, the rate of dissolution of the drug is controlled by slowly soluble polymers or by microencapsulation. Once the coating is dissolved, the drug becomes available for dissolution. By varying the thickness and/or the composition of the coating or coatings, the rate of drug release can be controlled. In some dissolution-controlled systems, a fraction of the total dose can comprise an immediate-release component. Dissolution-controlled systems include encapsulated/reservoir dissolution systems and matrix dissolution systems. Encapsulated dissolution systems can be prepared by coating particles or granules of drug with slowly soluble polymers of different thickness or by microencapsulation. Examples of coating materials useful in dissolution-controlled systems include gelatin, carnauba wax, shellac, cellulose acetate phthalate, and cellulose acetate butyrate. Matrix dissolution devices can be prepared, for example, by compressing a drug with a slowly soluble polymer carrier into a tablet form.

The rate of release of drug from osmotic pump systems is determined by the inflow of fluid across a semipermeable membrane into a reservoir, which contains an osmotic agent. The drug is either mixed with the agent or is located in a reservoir. The dosage form contains one or more small orifices from which dissolved drug is pumped at a rate determined by the rate of entrance of water due to osmotic pressure. As osmotic pressure within the dosage form increases, the drug is released through the orifice(s). The rate of release is constant and can be controlled within tight limits yielding relatively constant plasma and/or blood concentrations of the drug. Osmotic pump systems can provide a constant release of drug independent of the environment of the gastrointestinal tract. The rate of drug release can be modified by altering the osmotic agent and the sizes of the one or more orifices.

The release of drug from erosion-controlled systems is determined by the erosion rate of a carrier matrix. Drug is dispersed throughout the polymer and the rate of drug release depends on the erosion rate of the polymer. The drug-containing polymer can degrade from the bulk and/or from the surface of the dosage form.

Sustained release oral dosage forms can be in any appropriate form for oral administration, such as, for example, in the form of tablets, pills, or granules. Granules can be filled into capsules, compressed into tablets, or included in a liquid suspension. Sustained release oral dosage forms can additionally include an exterior coating to provide, for example, acid protection, ease of swallowing, flavor, identification, and the like.

In certain embodiments, sustained release oral dosage forms can comprise a therapeutically effective amount of a compound of Formula (I) and/or Formula (II) and a pharmaceutically acceptable vehicle. In certain embodiments, a sustained release oral dosage form can comprise less than a therapeutically effective amount of a compound of Formula (I) and/or Formula (II) and a pharmaceutically effective vehicle. Multiple sustained release oral dosage forms, each dosage form comprising less than a therapeutically effective amount of a compound of Formula (I) and/or Formula (II), can be administered at a single time or over a period of time to provide a therapeutically effective dose or regimen for treating a disease in a patient associated with a dysfunction in energy metabolism such as ischemia, oxidative stress, a neurodegenerative diseases, ischemic reperfusion injury, a cardiovascular disease, and muscle fatigue.

Sustained release oral dosage forms provided by the present disclosure can release a compound of Formula (I) and/or Formula (II) from the dosage form to facilitate the ability of the compound of Formula (I) and/or Formula (II) to be absorbed from an appropriate region of the gastrointestinal tract, for example, in the small intestine, or in the colon. In certain embodiments, a sustained release oral dosage from can release a compound of Formula (I) and/or Formula (II) from the dosage form over a period of at least about 4 hours, at least about 8 hours, at least about 12 hours, at least about 16 hours, at least about 20 hours, and in certain embodiments, at least about 24 hours. In certain embodiments, a sustained release oral dosage form can release a compound of Formula (I) and/or Formula (II) from the dosage form in a delivery pattern of from about 0 wt % to about 20 wt % in about 0 to about 4 hours, about 20 wt % to about 50 wt % in about 0 to about 8 hours, about 55 wt % to about 85 wt % in about 0 to about 14 hours, and about 80 wt % to about 100 wt % in about 0 to about 24 hours. In certain embodiments, a sustained release oral dosage form can release a compound of Formula (I) and/or Formula (II) from the dosage form in a delivery pattern of from about 0 wt % to about 20 wt % in about 0 to about 4 hours, about 20 wt % to about 50 wt % in about 0 to about 8 hours, about 55 wt % to about 85 wt % in about 0 to about 14 hours, and about 80 wt % to about 100 wt % in about 0 to about 20 hours. In certain embodiments, a sustained release oral dosage form can release a compound of Formula (I) and/or Formula (II) from the dosage form in a delivery pattern of from about 0 wt % to about 20 wt % in about 0 to about 2 hours, about 20 wt % to about 50 wt % in about 0 to about 4 hours, about 55 wt % to about 85 wt % in about 0 to about 7 hours, and about 80 wt % to about 100 wt % in about 0 to about 8 hours.

Sustained release oral dosage forms comprising a compound of Formula (I) and/or Formula (II) can provide a concentration of the corresponding creatine phosphate analog in the plasma, blood, or tissue of a patient over time, following oral administration to the patient. The concentration profile of a creatine phosphate analog can exhibit an AUC that is proportional to the dose of the corresponding compound of Formula (I) and/or Formula (II).

Regardless of the specific form of controlled release oral dosage form used, a compound of Formula (I) and/or Formula (II) can be released from an orally administered dosage form over a sufficient period of time to provide prolonged therapeutic concentrations of the compound of Formula (I) and/or Formula (II) in the plasma and/or blood of a patient. Following oral administration, a dosage form comprising a compound of Formula (I) and/or Formula (II) can provide a therapeutically effective concentration of the corresponding creatine phosphate analog in the plasma and/or blood of a patient for a continuous time period of at least about 4 hours, of at least about 8 hours, for at least about 12 hours, for at least about 16 hours, and in certain embodiments, for at least about 20 hours following oral administration of the dosage form to the patient. The continuous time periods during which a therapeutically effective concentration of a creatine phosphate analog is maintained can be the same or different. The continuous period of time during which a therapeutically effective plasma concentration of a creatine phosphate analog is maintained can begin shortly after oral administration or after a time interval.

In certain embodiments, an oral dosage for treating a disease, disorder, or condition in a patient can comprise a compound of Formula (I) and/or Formula (II) wherein the oral dosage form is adapted to provide, after a single administration of the oral dosage form to the patient, a therapeutically effective concentration of the corresponding creatine phosphate analog in the plasma of the patient for a first continuous time period selected from at least about 4 hours, at least about 8 hours, at least about 12 hours, and at least about 16 hours, and at least about 20 hours.

Methods of Use

The creatine kinase (creatine-creatine phosphate) system serves a number of functions in maintaining intracellular energy homeostasis (see e.g., Walsh et al., *J Physiol*, 2001, 537, 971-978). Phosphocreatine acts as a temporal energy buffer at intracellular sites of high energy translocation which operates when the rate of ATP utilization is greater than the rate of ATP production by mitochondrial respiration. Mitochondrial creatine kinase allows the high energy phosphate bond of newly synthesized ATP to be transferred to creatine, thus generating phosphocreatine, which is much more stable than ATP. Phosphocreatine can diffuse throughout a cell and its high energy phosphate bond can be used to regenerate ATP from ADP at heavy energy utilization sites where other creatine kinase enzymes are strategically positioned. These sites include membranes that engage in ion transport, axonal regions involved in transporting material along microtubules to and from presynaptic endings, and presynaptic endings where energy is required for neurotransmission. Neurons synthesize creatine, however the amount of creatine can be severely depleted during injury. As with skeletal and heart muscle, neuronal creatine stores can to some extent be increased by oral supplementation of creatine. The creatine kinase system also serves as an intracellular spatial energy transport mechanism. In this role as an energy carrier, energy generated by the ATP-ADP system within mitochondria is coupled to the creatine-creatine phosphate system in the cytosol, which in turn is coupled to extra-mitochondrial ATP-ADP systems at sites of high intracellular energy transduction. The creatine-creatine phosphate system is also believed to act as a low threshold ADP sensor that maintains ATP-ADP concentration ratios in subcellular locations wherein creatine kinase is functionally coupled to ATP-consuming and ATP-producing pathways. For example, it has been shown that creatine can react with ATP derived from mitochondrial respiration in a reaction catalyzed by mitochondrial creatine kinase and functionally coupled to adenine nucleotide translocase, thereby resulting in an increase in local ADP concentration and the stimulation of mitochondrial respiration. The creatine kinase system is therefore particularly important in maintaining energy homeostasis, including ATP homeostasis, in cells, tissues, and organs with high-energy consumption requirements such as neurons and muscles.

Compounds of Formula (I) and/or Formula (II) and pharmaceutical compositions provided by the present disclosure can be useful in treating of diseases, disorders, or conditions in a patient associated with a dysfunction in energy metabolism. In certain embodiments, the dysfunction in energy metabolism comprises a depletion in intracellular ATP concentration, a decreased intracellular creatine phosphate concentration, a decreased intracellular creatine phosphate to ATP concentration ratio, and/or a dysfunction in the creatine kinase system in a tissue or organ affected by the disease. In certain embodiments, a dysfunction in energy metabolism comprises a decreased intracellular ATP concentration in a tissue or organ affected by the disease. In certain embodiments, a dysfunction in energy metabolism comprises a decreased intracellular creatine phosphate concentration in a tissue or organ affected by the disease. In certain embodiments, the dysfunction in energy metabolism comprises a dysfunction in the creatine kinase system and/or other intracellular energy pathway in a tissue or organ affected by the disease. In certain embodiments, a disease associated with a dysfunction in energy metabolism is selected from ischemia, oxidative stress, a neurodegenerative disease, ischemic reperfusion injury, a cardiovascular disease, multiple sclerosis, a psychotic disease, and muscle fatigue. In certain embodiments, treating a disease comprises effecting energy homeostasis in a tissue or organ affected by the disease.

Compounds of Formula (I) and/or Formula (II) and pharmaceutical compositions thereof can be used to treat a disease in a patient associated with oxidative stress by administering to a patient in need of such treatment a therapeutically effective amount of a compound of Formula (I) and/or Formula (II) or a pharmaceutical composition thereof. In certain embodiments, the oxidative stress is associated with ischemia or a neurodegenerative disorder. Methods provided by the present disclosure include treating an oxidatively stressed tissue or organ by contacting the tissue or organ with a compound of Formula (I) and/or Formula (II) or a pharmaceutical composition thereof.

Compounds and pharmaceutical compositions provided by the present disclosure can be useful in treating diseases, disorders, or conditions in which a rapid increase in intracellular creatine phosphate levels has a therapeutic effect.

Ischemia

Compounds and pharmaceutical compositions provided by the present disclosure can be used to treat acute or chronic ischemic diseases, disorders, or conditions. Ischemia is an imbalance of oxygen supply and demand in a cell, tissue, or organ. Ischemia is characterized by hypoxia, including anoxia, insufficiency of metabolic substrates for normal cellular bioenergetics, and accumulation of metabolic waste. Ischemia in a tissue or organ may be caused by a vascular insufficiency such as arteriosclerosis, thrombosis, embolism, torsion, or compression, hypotension such as shock or hemorrhage, increased tissue mass (hypertrophy), increased workload (tachycardia, exercise), and/or by decreased tissue stress such as cardiac dilation. Ischemia can also result from trauma or surgical procedures. Depending on the severity and duration of the injury, ischemia can lead to a reversible loss of cellular function or to irreversible cell death. Different cell types have different thresholds to ischemic injury depending, at least in part, on the cellular energy requirements of the tissue(s) or organ(s) affected. Parenchymal cells such as neurons (3-4 minutes), cardiac muscles, hepatocytes, renal tubular cells, gastrointestinal epithelium (20-80 minutes) and fibroblasts, epidermis, and skeletal muscle (hours) are more susceptible to ischemic injury than are stromal cells. A number of studies suggest a correlation between the functional capacity of the creatine kinase system and ischemic tolerance of a given tissue, and indicate that strategies toward improving the functional capacity of the creatine kinase system may be effective for improving ischemic tolerance in tissue (see e.g., Wyss and Kaddurah-Daouk, *Physiological Reviews*, 2000, 80(3), 1107-1213, which is incorporated by reference herein in its entirety). For example, oral creatine supplementation inhibits mitochondrial cytochrome C release and downstream caspase-3 activation, resulting in ischemic neuroprotection. Associated with inhibition of cytochrome C release and caspase-3 activation and with neuroprotection, creatine administration inhibits ischemia-mediated ATP depletion.

Compounds and pharmaceutical compositions provided by the present disclosure can be used to treat acute or chronic ischemia. In certain embodiments, a compound or composition can be particularly useful in acute or emergency treatment of ischemia in tissue or organs characterized by high energy demand such as the brain, neurons, heart, lung, kidney, or the intestine.

The high energy requirements compared to the low energy reserves render the brain particularly vulnerable to hypoxic conditions. Although the brain constitutes only a small fraction of total body weight (about 2%), it accounts for a disproportionately large percentage of $O_2$ consumption (about 20%). Under physiological conditions, enhanced demand for $O_2$ is rapidly and adequately compensated for by an increase in cerebral blood flow. The longer the duration of hypoxia/ischemia, the larger and more diffuse the areas of the brain that are affected. The areas most vulnerable to ischemic damage are the brainstem, hippocampus, and cerebral cortex. Injury progresses and eventually becomes irreversible except if oxygenation is not restored. Acute cell death occurs mainly through necrosis but hypoxia also causes delayed apoptosis. In addition glutamate release from presynaptic neurons can further enhance $Ca^{2+}$ influx and result in catastrophic collapse in postsynaptic cells. If the ischemia is not too severe, cells can suppress some functions, i.e., protein synthesis and spontaneous electrical activity, in a process called penumbra, which can be reversed provided that $O_2$ supply is resumed. However, the process of restoring oxygen levels to ischemically stressed tissue, e.g., reperfusion, can also induce irreversible cell death, mainly through the generation of reactive oxygen species and inflammatory cell infiltration.

The neuron is limited by its availability of energy-generating substrates, being limited to using primarily glucose, ketone bodies, or lactate. The neuron does not produce or store glucose or ketone bodies and cannot survive for any significant period of time without a substrate, which is absorbed and used directly or indirectly from the bloodstream. Thus, a constant supply of an energy-generating substrate must be present in the blood at all times in an amount sufficient to supply the entire brain and the rest of the body with energy-generating substrates. Brain cells require a concentration of about 5 mM glucose (or its equivalent) in order to maintain its optimal rate of oxidative phosphorylation to produce ATP. Nutrients enter cells by passing through the cell membrane. Nutrient delivery frequently relies upon mechanisms outside the cell membranes such as oral intake, absorption, circulatory transport and interstitial flux. Once localized in the vicinity of the cell, membrane-specific processes play a role in nutrient transport sequentially across the blood-brain barrier and then into the interior of the cell and into various subcellular organelles. Nutrient transport is made possible by the breakdown of ATP by ATPases. $Na^+$ gradients created by $Na^+/K^+$ ATPases can be used by cells to transport nutrient molecules across cell membranes.

Lack of oxygen or glucose prevents or limits the ability of neurons to synthesize ATP. The intracellular creatine/phosphocreatine system can to some extent compensate for the lack of oxygen or glucose. Creatine kinase catalyses the synthesis of phosphocreatine from creatine in normal brain tissue. Under conditions of ATP depletion, phosphocreatine can donate its phosphate group to ADP to resynthesize ATP. However, neuronal phosphocreatine content is limited following complete anoxia or ischemia phosphocreatine is also rapidly depleted. ATP depletion is believed to block $Na^+/K^+$ ATPases causing neurons to depolarize and lose membrane potential.

Depleted oxygen levels have several other consequences on cellular bioenergetics and function that can ultimately lead to cell death. For example, dysfunctional bioenergetics also involves impaired calcium homeostasis. The regulation of calcium plays a central role in the proper functioning and survival of neurons. Calcium pumps, located on cell membranes, use ATP to transport calcium ions out of the neuron. Proper activity of the calcium pump is essential in the maintenance of neuronal, mitochondrial, and endoplasmic reticulum homeostasis. Alterations in calcium pump function modulate enzyme activity within a cell and also play a critical role in triggering the mitochondrial permeability transition, which may lead to cell death. For example, intracellular $Ca^{2+}$ metabolism is believed to contribute to cell death in Alzheimer's disease. For example, under conditions of oxidative stress, the production of oxygen free radicals exceeds endogenous free radical protective mechanisms. This impairs neuronal metabolism and function by direct free radical damage to important cellular biomolecules including membrane lipids, nucleic acids, and functional proteins; and by modulation of critical signal transduction pathways. Neural function is dependent upon transmission of electrical impulses between cells. This activity relies upon the precise actions of multiple membrane proteins each suspended in a phospholipid bilayer. The optimal activity of this dynamic membrane microenvironment depends upon the exact status and chemical composition of the lipid constituents. Lacking the appropriate phospholipid environment, cell channel proteins, enzymes, and receptors are not able to achieve sustained levels of optimal function. In addition, oxidative stress and/or abnormal methyl metabolism can reduce the fluidity of the membranous lipid bilayer with subsequent adverse effects upon embedded functional proteins. Dysfunctional bioenergetics may also adversely affect passage of high-energy electrons along the respiratory chain.

Apoptosis refers to the energy-requiring process of programmed cell death whereupon an individual nerve cell under appropriate circumstances initiates a process leading to cell death. Certain of the mechanisms discussed above may initiate apoptotic pathways including oxidative stress, calcium overload, cellular energy deficiency, trophic factor withdrawal, and abnormal amyloid precursor protein processing. In ischemia, neurons in the brain tissue region that are most severely affected by hypoxic injury die rapidly by necrosis, whereas neurons exposed to lesser degrees of hypoxia die by apoptosis. The shift from necrotic cell death to apoptotic cell death is associated with increasing levels of intra cellular ATP. It has been shown that creatine supplementation can result in a greater ability to buffer ATP levels and reduce cell death and thereby provide protection from anoxic and ischemic damage (Balestrino et al., *Amino Acids*, 2002, 23, 221-229; and Zhu et al., *J Neurosci* 2004, 24(26), 5909-5912, each of which is incorporated by reference herein in its entirety).

In certain embodiments, compounds and pharmaceutical compositions provided by the present disclosure can be used to treat a cardiovascular disease, including cerebral ischemia (stroke) and myocardial ischemia (heart infarction). Ischemic heart disease, as the underlying cause of many cases of acute myocardial infarction, congestive heart failure, arrhythmias, and sudden cardiac death, is a leading cause of morbidity and mortality in all industrialized nations. In the United States, ischemic heart disease causes nearly 20% of all deaths (~600,000 deaths each year) with many of these deaths occurring before the patient arrives at the hospital. An estimated 1.1 million Americans will have a new or recurrent acute myocardial infarction each year, and many survivors will experience lasting morbidity, with progression to heart failure and death. As the population grows older and co-morbidities such as obesity and diabetes become more prevalent, the public health burden caused by ischemic heart disease is likely to increase.

Optimal cellular bioenergetics rely on: (1) adequate delivery of oxygen and substrates to the mitochondria; (2) the oxidative capacity of mitochondria; (3) adequate amounts of high-energy phosphate and the creatine phosphate/ATP ratio; (4) efficient energy transfer from mitochondria to sites of energy utilization; (5) adequate local regulation of ATP/ADP ratios near ATPases; and (6) efficient feedback signaling from utilization sites to maintain energetic homeostasis in the cell. Defects in these cardiac energetic pathways have been found in cardiovascular diseases such as dilated and hypertrophic cardiomyopathies of various origins, cardiac conduction defects, and ischemic heart diseases (Saks et al., *J Physiol* 2006, 571.2, 253-273; Ventura-Clapier et al., *J Physiol* 2003, 555.1, 1-13; and Ingwall and Weiss, *Circ Res* 2004, 95, 135-145, each of which is incorporated by reference herein in its entirety). A decrease in the creatine phosphate/ATP ratio is consistently reported in failing human heart and experimental heart failure, even at moderate workloads. Creatine, creatine transporter, creatine phosphate, and ATP are significantly reduced and the decrease in the creatine phosphate/ATP ratio is a predictor of mortality in congenital heart failures. Also, a down-regulation of creatine transporter protein expression has been shown in experimental animal models of heart disease, as well as in failing human myocardium, indicating that the generally lowered creatine phosphate and creatine levels measured in failing hearts are related to down-regulated creatine transporter capacity.

Cardiovascular disease includes hypertension, heart failure such as congestive heat failure or heart failure following myocardial infarction, arrhythmia, diastolic dysfunction such as left ventricular diastolic dysfunction, diastolic heart failure, or impaired diastolic filling, systolic dysfunction, ischemia such as myocardial ischemia, cardiomyopathy such as hypertrophic cardiomyopathy and dilated cardiomyopathy, sudden cardiac death, myocardial fibrosis, vascular fibrosis, impaired arterial compliance, myocardial necrotic lesions, vascular damage in the heart, vascular inflammation in the heart, myocardial infarction including both acute post-myocardial infarction and chronic post-myocardial infarction conditions, coronary angioplasty, left ventricular hypertrophy, decreased ejection fraction, coronary thrombosis, cardiac lesions, vascular wall hypertrophy in the heart, endothelial thickening, myocarditis, and coronary artery disease such as fibrinoid necrosis or coronary arteries. Ventricular hypertrophy due to systemic hypertension in association with coronary ischemic heart disease is recognized as a major risk factor for sudden death, post infarction heart failure, and cardiac rupture. Patients with severe left ventricular hypertrophy are particularly susceptible to hypoxia or ischemia.

Neuroprotective effects of compounds of Formula (I) or Formula (II) can be determined using animal models of cerebral ischemia such as those described, for example, in Cimino et al., *Neurotoxicol* 2005, 26(5), 9929-33; Konstas et al., *Neurocrit Care* 2006, 4(2), 168-78; Wasterlain et al., *Neurology* 1993, 43(11), 2303-10; and Zhu et al., *J Neuroscience* 2004, 24(26), 5909-5912.

Ischemic Reperfusion Injury

Reperfusion injury is damage to tissue when blood supply returns to the tissue after a period of ischemia. The absence in a tissue or organ of oxygen and nutrients from blood creates a condition in which the restoration of circulation results in inflammation and oxidative damage from the oxygen, rather than restoration of normal function. The damage of ischemic reperfusion injury is due in part to the inflammatory response of damaged tissue. Reperfusion contributes to the ischemic cascade in the brain, which is involved in stroke and brain trauma. Repeated bouts of ischemia and reperfusion also are believed to be a factor leading to the formation and failure to heal of chronic wounds such as pressure sores and diabetic foot ulcers (Mustoe, *Am J Surgery* 2004, 187(5), S65-S70, which is incorporated by reference herein in its entirety). In certain embodiments, the methods and compositions of the disclosure can protect the muscle and organs such as, for example, the heart, liver, kidney, brain, lung, spleen and steroidogenic organs, e.g. thyroid, adrenal glands, and gonads, from damage as a result of ischemia reperfusion injury.

Ischemia followed by reperfusion is a major cause of skeletal and cardiac muscle damage in mammals. Ischemia is caused by a reduction in oxygen supplied to tissues or organs as a result of reduced blood flow and can lead to organ dysfunction. Reduced blood supply can result from occlusion or blood diversion due to vessel thrombosis, such as myocardial infarction, stenosis, accidental vessel injury, or surgical procedures. Subsequent reestablishment of an adequate supply of oxygenated blood to the tissue or organ can result in increased damage, a process known as ischemia reperfusion injury or occlusion reperfusion injury. Complications arising from ischemia reperfusion injury include stroke, fatal or non-fatal myocardial infarction, myocardial remodeling, aneurysms, peripheral vascular disease, tissue necrosis, kidney failure, and post-surgical loss of muscle tone.

Restoration of coronary blood flow following a transient period of ischemia (reperfusion), though necessary for myocyte survival and to restore aerobic metabolism, introduces a separate series of stresses that can exacerbate cell injury. Reactive oxygen species generated during reperfusion damage proteins and membrane structures within cardiomyocytes and can activate signal transduction pathways that lead to apoptosis. Adherence of leukocytes to postischemic endothelial cells can clog capillaries and release inflammatory mediators. Upon reperfusion, the influx of activated complement, catecholamines, and other signaling molecules contained in plasma or elaborated locally within the myocardial wall may also influence the course of events within cells of the myocardium. As with the direct consequences of ischemia, reperfusion injury is an important feature of acute coronary syndromes. Such injury occurs both spontaneously, as a result of fibrinolysis of coronary thromboses, and as a consequence of fibrinolytic drugs of acute angioplasty, treatments that are now commonly used to open occluded vessels.

In certain embodiments, compounds of Formula (I) and/or Formula (II) and compositions thereof provided by the present disclosure can be used to treat a condition associated with ischemic reperfusion injury or reduce ischemic reperfusion injury. Ischemic reperfusion injury can be associated with oxygen deprivation, neutrophil activation, and/or myeloperoxidase production. Ischemic reperfusion injury can be the result of a number of disease states or can be iatrogenically induced, for example, by blood clots, stenosis, or surgery.

In certain embodiments, compounds of Formula (I) and/or Formula (II) and compositions thereof can be used to treat stroke, a fatal or non-fatal myocardial infarction, peripheral vascular disease, tissue necrosis, and kidney failure, and post-surgical loss of muscle tone resulting from ischemic reperfusion injury. In certain embodiments, the methods and compositions provided by the present disclosure reduce or mitigate the extent of ischemic reperfusion injury.

In certain embodiments, compounds of Formula (I) and/or Formula (II) and compositions thereof can be used to treat, reduce or prevent ischemic reperfusion injury associated with occlusion or blood diversion due to vessel stenosis, thrombosis, accidental vessel injury, or surgical procedures.

In certain embodiments, compounds of Formula (I) and/or Formula (II) and compositions thereof can also be used to treat any other condition associated with ischemic reperfusion such as myocardial infarction, stroke, intermittent claudication, peripheral arterial disease, acute coronary syndrome, cardiovascular disease and muscle damage as a result of occlusion of a blood vessel.

In certain embodiments, compounds of Formula (I) and/or Formula (II) and compositions thereof can be used to treat reperfusion injury associated with myocardial infarction, stenosis, at least one blood clot, stroke, intermittent claudication, peripheral arterial disease, acute coronary syndrome, cardiovascular disease, or muscle damage as a result of occlusion of a blood vessel.

In certain embodiments, compounds of Formula (I) and/or Formula (II) and compositions thereof can be used in conjunction with cardiac surgery, for example, in or with cardioplegic solutions to prevent or minimize ischemia or reperfusion injury to the myocardium. In certain embodiments, the methods and compositions can be used with a cardiopulmonary bypass machine during cardiac surgery to prevent or reduce ischemic reperfusion injury to the myocardium.

In certain embodiments, the methods and compositions provided by the present disclosure can protect muscle and organs such as, for example, the heart, liver, kidney, brain, lung, spleen and steroidogenic organs, e.g. thyroid, adrenal glands, and gonads, from damage as a result of ischemia reperfusion injury.

Compounds and pharmaceutical compositions provided by the present disclosure can be used to treat ischemic reperfusion injury in a tissue or organ by contacting the tissue or organ with an effective amount of the compound or pharmaceutical composition. The tissue or organ may be in a patient or outside of a patient, i.e., extracorporeal. The tissue or organ can be a transplant tissue or organ, and the compound or pharmaceutical composition can be contacted with the transplant tissue or organ before removal, during transit, during transplantation, and/or after the tissue or organ is transplanted in the recipient.

In certain embodiments, compounds or pharmaceutical compositions provided by the present disclosure can be used to treat ischemic perfusion injury caused by surgery, such as cardiac surgery. A compound or pharmaceutical composition can be administered before, during, and/or after surgery. In certain embodiments, a compound or pharmaceutical composition provided by the present disclosure can be used to treat ischemic reperfusion injury to muscle, including cardiac muscle, skeletal muscle, or smooth muscle, and in certain embodiments, to treat ischemic reperfusion injury to an organ such as the heart, lung, kidney, spleen, liver, neuron, or brain. A compound of Formula (I) and/or Formula (II) or pharmaceutical composition thereof can be administered before, during, and/or after surgery.

In certain embodiments, compounds of Formula (I) and/or Formula (II) or pharmaceutical compositions provided by the present disclosure can be used to treat ischemic perfusion injury to a muscle, including cardiac muscle, skeletal muscle, and smooth muscle.

The efficacy of a compound of Formula (I) or Formula (II) for treating ischemic reperfusion injury may be assessed using animal models and in clinical trials. Examples of useful methods for assessing efficacy in treating ischemic reperfusion injury are disclosed, for example, in Prass et al., *J Cereb Blood Flow Metab* 2007, 27(3), 452-459; Arya et al., *Life Sci* 2006, 79(1), 38-44; Lee et al., *Eur. J. Pharmacol* 2005, 523 (1-3), 101-108; and Bisgaier et al., U.S. Application Publication No. 2004/0038891. Useful methods for evaluating transplant perfusion/reperfusion are described, for example, in Ross et al., *Am J. Physiol—Lung Cellular Mol. Physiol.* 2000, 279(3), L528-536.

Transplant Perfusion

In certain embodiments, compounds of Formula (I) and/or Formula (II) or pharmaceutical compositions thereof can be used to increase the viability of organ transplants by perfusing the organs with a compound of Formula (I) and/or Formula (II) or pharmaceutical compositions thereof. Increased creatine phosphate levels are expected to prevent or minimize ischemic damage to an organ. Perfusing with a creatine phosphate analog prodrug during organ removal, following removal of a donor organ, during implantation, and/or following organ transplantation, can enhance the viability of the organ, especially a metabolically active organ, such as the heart or pancreas, and thereby reduce rejection rates, and/or increase the time window for organ transplants.

In certain embodiments, compounds of Formula (I) and/or Formula (II) and compositions thereof can be used to treat, prevent or reduce ischemia reperfusion injury in extracorporeal tissue or organs. Extracorporeal tissue or organs are tissue or organs not in an individual (also termed ex vivo), such as in transplantation. For tissue and organ transplantation, donor tissue and organs removed are also susceptible to reperfusion injury during removal, while in transit, during implantation and following transplantation into a recipient. The methods and compositions can be used to increase the viability of a transplantable tissue or organ by, for example, supplementing solutions used to maintain or preserve transplantable tissues or organs. For example, the methods and compositions can be used to bathe the transplantable tissue or organ during transport or can be placed in contact with the transplantable tissue or organ prior to, during or after transplantation.

Neurodegenerative Diseases

Neurodegenerative diseases featuring cell death can be categorized as acute, e.g., stroke, traumatic brain injury, spinal cord injury, and chronic, e.g., amyotrophic lateral sclerosis, Huntington's disease, Parkinson's disease, and Alzheimer's disease. Although these diseases have different causes and affect different neuronal populations, they share similar impairment in intracellular energy metabolism. For example, the intracellular concentration of ATP is decreased, resulting in cystolic accumulation of $Ca^{2+}$ and stimulation of formation of readily oxygen species. $Ca^{2+}$ and reactive oxygen species, in turn, can trigger apoptotic cell death. For these disorders, impairment of brain creatine metabolism is also evident as reflected in decreased total creatine concentration, creatine phosphate concentration, creatine kinase activity, and/or creatine transporter content (see e.g., Wyss and Kaddurah-Daouk, *Physiol Rev* 2000, 80, 1107-1213; Tarnopolsky and Beal, *Ann Neurol* 2001, 49, 561-574; and Butterfield and Kanski, *Mech Ageing Dev* 2001, 122, 945-962, each of which is incorporated by reference herein in its entirety).

Acute and chronic neurodegenerative diseases are illnesses associated with high morbidity and mortality and few options are available for their treatment. A characteristic of many neurodegenerative diseases, which include stroke, brain trauma, spinal cord injury, amyotrophic lateral sclerosis, Huntington's disease, Alzheimer's disease, and Parkinson's disease, is neuronal-cell death. Cell death occurs by necrosis or apoptosis. Necrotic cell death in the central nervous system follows acute ischemia or traumatic injury to the brain or spinal cord. It occurs in areas that are most severely affected by abrupt biochemical collapse, which leads to the generation of free radicals and excitotoxins. Mitochondrial and nuclear swelling, dissolution of organelles, and condensation of chromatin around the nucleus are followed by the rupture of nuclear and cytoplasmic membranes and the degradation of DNA by random enzymatic cuts. Apoptotic cell death can be a feature of both acute and chronic neurological diseases. Apoptosis occurs in areas that are not severely affected by an injury. For example, after ischemia, there is necrotic cell death in the core of the lesion, where hypoxia is most severe, and apoptosis occurs in the penumbra, where collateral blood flow reduces the degree of hypoxia. Apoptotic cell death is also a component of the lesion that appears after brain or spinal cord injury. In chronic neurodegenerative diseases, apoptosis is the predominant form of cell death. In apoptosis, a biochemical cascade activates proteases that destroy molecules required for cell survival and others that mediate a program of cell death. Caspases directly and indirectly contribute to the morphologic changes of the cell during apoptosis (Friedlander, *N Engl J Med* 2003, 348(14), 1365-75). Oral creatine supplementation has been shown to inhibit mitochondrial cytochrome C release and downstream caspase-3 activation, and ATP depletion inhibition of the caspase-mediated cell death cascades in cerebral ischemia (Zhu et al., *J Neurosci* 2004, 24(26), 5909-5912) indicating that manipulation of the creatine kinase system may be effective in controlling apoptotic cell death in chronic neurodegenerative diseases.

Creatine administration shows neuroprotective effects, particularly in animal models of Parkinson's disease, Huntington's disease, and ALS (Wyss and Schulze, *Neuroscience* 2002, 112(2), 243-260, which is incorporated by reference herein in its entirety) and it is recognized that the level of oxidative stress may be a determinant of metabolic determination in a variety of neurodegenerative diseases. Current hypotheses regarding the mechanisms of creatine-mediated neuroprotection include enhanced energy storage, as well as stabilization of the mitochondrial permeability transition pore by octomeric conformation of creatine kinase. It is therefore believed that higher levels of intracellular creatine improve the overall bioenergetic status of a cell, rendering the cell more resistant to injury.

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate and thereby reduce the production of dopamine and the number of connections between nerve cells in the basal ganglia. As a result, the basal ganglia is unable to smooth muscle movement and coordinate changes in posture, leading to tremor, incoordination, and slowed, reduced movement (bradykinesia) (Blandini, et al., *Mol. Neurobiol.* 1996, 12, 73-94).

It is believed that oxidative stress may be a factor in the metabolic deterioration seen in Parkinson's disease tissue (Ebadi et al., *Prog Neurobiol* 1996, 48, 1-19; Jenner and Olanow, *Ann Neurol* 1998, 44 Suppl 1, S72-S84; and Sun and Chen, *J Biomed Sci* 1998, 5, 401-414, each of which is incorporated by reference herein in its entirety) and creatine supplementation has been shown to exhibit neuroprotective effects (Matthews et al., *Exp Neurol*, 1999, 157, 142-149, which is incorporated by reference herein in its entirety).

The efficacy of administering a compound of Formula (I) or Formula (II) for treating Parkinson's disease may be assessed using animal and human models of Parkinson's disease and clinical studies. Animal and human models of Parkinson's disease are known (see, e.g., O'Neil et al., *CNS Drug Rev.* 2005, 11(1), 77-96; Faulkner et al., *Ann. Pharmacother.* 2003, 37(2), 282-6; Olson et al., *Am. J. Med.* 1997, 102(1), 60-6; Van Blercom et al., *Clin Neuropharmacol.* 2004, 27(3), 124-8; Cho et al., *Biochem. Biophys. Res. Commun.* 2006, 341, 6-12; Emborg, *J. Neuro. Meth.* 2004, 139, 121-143; Tolwani et al., *Lab Anim Sci* 1999, 49(4), 363-71; Hirsch et al., *J Neural Transm Suppl* 2003, 65, 89-100; Orth and Tabrizi, *Mov Disord* 2003, 18(7), 729-37; Betarbet et al., *Bioessays* 2002, 24(4), 308-18; and McGeer and McGeer, *Neurobiol Aging* 2007, 28(5), 639-647).

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

It is believed that oxidative stress may be a factor in the metabolic deterioration seen in Alzheimer's disease tissue with creatine kinase being one of the targets of oxidative damage (Pratico et al., *FASEB J* 1998, 12, 1777-1783; Smith et al., *J Neurochem* 1998, 70, 2212-2215; and Yatin et al., *Neurochem Res* 1999, 24, 427-435, each of which is incorporated by reference herein in its entirety) and studies have shown a correlation between intracellular levels of creatine phosphate and the progress of dementia (Pettegrew et al., *Neurobiol Aging* 1994, 15, 117-132, which is incorporated by reference herein in its entirety).

The efficacy of administering a compound of Formula (I) or Formula (II) for treating Alzheimer's disease may be assessed using animal and human models of Alzheimer's disease and clinical studies. Useful animal models for assessing the efficacy of compounds for treating Alzheimer's disease are disclosed, for example, in Van Dam and De Dyn, *Nature Revs Drug Disc* 2006, 5, 956-970; Simpkins et al., *Ann N Y Acad Sci*, 2005, 1052, 233-242; Higgins and Jacobsen, *Behav Pharmacol* 2003, 14(5-6), 419-38; Janus and Westaway, *Physiol Behav* 2001, 73(5), 873-86; and Conn, ed., "Handbook of Models in Human Aging," 2006, Elsevier Science & Technology.

Huntington's Disease

Huntington's disease is an autosomal dominant neurodegenerative disorder in which specific cell death occurs in the neostriatum and cortex (Martin, *N Engl J Med* 1999, 340, 1970-80, which is incorporated by reference herein in its entirety). Onset usually occurs during the fourth or fifth decade of life, with a mean survival at age onset of 14 to 20 years. Huntington's disease is fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin. A number of studies suggest that there is a progressive impairment of energy metabolism, possibly resulting from mitochondrial damage caused by oxidative stress as a consequence of free radical generation. Preclinical studies in animal models of Huntington's disease have documented neuroprotective effects of creatine administration. For example, neuroprotection by creatine is associated with higher levels of creatine phosphate and creatine and reduced lactate levels in the brain, consistent with improved energy production (see, Ryu et al., *Pharmacology & Therapeutics* 2005, 108(2), 193-207, which is incorporated by reference herein in its entirety).

The efficacy of administering a compound of Formula (I) or Formula (II) for treating Huntington's disease may be assessed using animal and human models of Huntington's disease and clinical studies. Animal models of Huntington's disease are disclosed, for example, in Riess and Hoersten, U.S. Application Publication No. 2007/0044162; Rubinsztein, *Trends in Genetics,* 2002, 18(4), 202-209; Matthews et al., *J. Neuroscience* 1998, 18(1), 156-63; Tadros et al., *Pharmacol Biochem Behav* 2005, 82(3), 574-82, and in Kaddurah-Daouk et al., U.S. Pat. No. 6,706,764, and U.S. Application Publication Nos. 2002/0161049, 2004/0106680, and 2007/0044162. A placebo-controlled clinical trial evaluating the efficacy of creatine supplementation to treat Huntington's disease is disclosed in Verbessem et al., *Neurology* 2003, 61, 925-230.

Amyotrophic Lateral Sclerosis

Amyotrophic lateral sclerosis (ALS) is a progressive neurodegenerative disorder characterized by the progressive and specific loss of motor neurons in the brain, brain stem, and spinal cord (Rowland and Schneider, *N Engl J Med* 2001, 344, 1688-1700, which is incorporated by reference herein in its entirety). ALS begins with weakness, often in the hands and less frequently in the feet, that generally progresses up an arm or leg. Over time, weakness increases and spasticity develops characterized by muscle twitching and tightening, followed by muscle spasms and possibly tremors. The average age of onset is 55 years, and the average life expectancy after clinical onset is 4 years. The only recognized treatment for ALS is riluzole, which can extend survival by only about three months. Oral creatine has been shown to provide neuroprotective effects in a transgenic animal model of ALS (Klivenyi et al., *Nat Med* 1999, 5, 347-50, which is incorporated by reference herein in its entirety).

The efficacy of administering a compound of Formula (I) or Formula (II) for treating ALS may be assessed using animal and human models of ALS and clinical studies. Natural disease models of ALS include mouse models (motor neuron degeneration, progressive motor neuropathy, and wobbler) and the hereditary canine spinal muscular atrophy canine model (Pioro and Mitsumoto, *Clin Neurosci,* 1995-1996, 3(6), 375-85). Experimentally produced and genetically engineered animal models of ALS can also useful in assessing therapeutic efficacy (see e.g., Doble and Kennelu, *Amyotroph Lateral Scler Other Motor Neuron Disord.* 2000, 1(5), 301-12; Grieb, *Folia Neuropathol.* 2004, 42(4), 239-48; Price et al., *Rev Neurol (Paris),* 1997, 153(8-9), 484-95; and Klivenyi et al., *Nat Med* 1999, 5, 347-50). Specifically, the SOD1-G93A mouse model is a recognized model for ALS. Examples of clinical trial protocols useful in assessing treatment of ALS are described, for example, in Mitsumoto, *Amyotroph Lateral Scler Other Motor Neuron Disord.* 2001, 2 Suppl 1, S10-S14; Meininger, *Neurodegener Dis* 2005, 2, 208-14; and Ludolph and Sperfeld, *Neurodegener Dis.* 2005, 2(3-4), 215-9.

Multiple Sclerosis

Multiple sclerosis (MS) is a multifaceted inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, Lab Invest 2001, 81, 263-281; and Virley, *NeruoRx* 2005, 2(4), 638-649). Although the causal events that precipitate the disease are not fully understood, most evidence implicates an autoimmune etiology together with environmental factors, as well as specific genetic predispositions. Functional impairment, disability, and handicap are expressed as paralysis, sensory and octintive disturbances spasticity, tremor, a lack of coordination, and visual impairment, which impact on the quality of life of the individual. The clinical course of MS can vary from individual to individual, but invariably the disease can be categorized in three forms: relapsing-remitting, secondary progressive, and primary progressive. Several studies implicate dysfunction of creatine phosphate metabolism with the etiology and symptoms of the disease (Minderhoud et al., *Arch Neurol* 1992, 49(2), 161-5; He et al., *Radiology* 2005, 234(1), 211-7; Tartaglia et al., *Arch Neurology* 2004, 61(2), 201-207; Duong et al., *J Neurol* 2007, April 20; and Ju et al., *Magnetic Res Imaging* 2004, 22, 427-429), although creatine ingestion alone does not appear to be effective in improving exercise capacity in individuals with MS (Lambert et al., *Arch Phys Med Rehab* 2003, 84(8), 1206-1210).

Assessment of MS treatment efficacy in clinical trials can be accomplished using tools such as the Expanded Disability Status Scale (Kurtzke, *Neurology* 1983, 33, 1444-1452) and the MS Functional Composite (Fischer et al., *Mult Scler,* 1999, 5, 244-250) as well as magnetic resonance imaging lesion load, biomarkers, and self-reported quality of life (see e.g., Kapoor, *Cur Opinion Neurol* 2006, 19, 255-259). Animal models of MS shown to be useful to identify and validate potential therapeutics include experimental autoimmune/allergic encephalomyelitis (EAE) rodent models that simulate the clinical and pathological manifestations of MS (Werkerle and Kurschus, *Drug Discovery Today: Disease Models, Nervous System Disorders,* 2006, 3(4), 359-367; Gijbels et al., *Neurosci Res Commun* 2000, 26, 193-206; and Hofstetter et al., *J Immunol* 2002, 169, 117-125), and nonhuman primate EAE models ('t Hart et al., *Immunol Today* 2000, 21, 290-297).

Psychotic Disorders

In certain embodiments, compounds of Formula (I) and/or Formula (II) or pharmaceutical compositions thereof can be used to treat psychotic disorders such as, for example, schizophrenia, bipolar disorder, and anxiety.

Schizophrenia

Schizophrenia is a chronic, severe, and disabling brain disorder that affects about one percent of people worldwide, including 3.2 million Americans. Schizophrenia encompasses a group of neuropsychiatric disorders characterized by dysfunctions of the thinking process, such as delusions, hallucinations, and extensive withdrawal of the patient's interests from other people. Schizophrenia includes the subtypes of paranoid schizophrenia characterized by a preoccupation with delusions or auditory hallucinations, hebephrenic or disorganized schizophrenia characterized by disorganized speech, disorganized behavior, and flat or inappropriate emotions; catatonic schizophrenia dominated by physical symptoms such as immobility, excessive motor activity, or the assumption of bizarre postures; undifferentiated schizophrenia characterized by a combination of symptoms characteristic of the other subtypes; and residual schizophrenia in which a person is not currently suffering from positive symptoms but manifests negative and/or cognitive symptoms of schizophrenia (see DSM-IV-TR classifications 295.30 (Paranoid Type), 295.10 (Disorganized Type), 295.20 (Catatonic Type), 295.90 (Undifferentiated Type), and 295.60 (Residual Type); Diagnostic and Statistical Manual of Mental Disorders, 4th Edition, American Psychiatric Association, 297-319, 2005). Schizophrenia includes these and other closely associated psychotic disorders such as schizophreniform disorder, schizoaffective disorder, delusional disorder, brief psychotic disorder, shared psychotic disorder, psychotic disorder due to a general medical condition, substance-induced psychotic disorder, and unspecified psychotic disorders (DSM-IV-TR, $4^{th}$ Edition, pp. 297-344, American Psychiatric Association, 2005).

Schizophrenia symptoms can be classified as positive, negative, or cognitive. Positive symptoms of schizophrenia include delusion and hallucination, which can be measured using, for example, the Positive and Negative Syndrome Scale (PANSS) (Kay et al., *Schizophrenia Bulletin* 1987, 13, 261-276). Negative symptoms of schizophrenia include affect blunting, anergia, alogia and social withdrawal, which can be measured for example, using (the Scales for the Assessment of Negative Symptoms (SANS) (Andreasen, 1983, *Scales for the Assessment of Negative Symptoms* (SANS), Iowa City, Iowa). Cognitive symptoms of schizophrenia include impairment in obtaining, organizing, and using intellectual knowledge which can be measured using the Positive and Negative Syndrome Scale-cognitive subscale (PANSS-cognitive subscale) (Lindenmayer et al., *J Nerv Ment Dis* 1994, 182, 631-638) or by assessing the ability to perform cognitive tasks such as, for example, using the Wisconsin Card Sorting Test (see, e.g., Green et al., *Am J Psychiatry* 1992, 149, 162-67; and Koren et al., *Schizophr Bull* 2006, 32(2), 310-26).

A number of studies support a correlation of schizophrenia with a dysfunction in brain high energy phosphate metabolism (Fukuzako, *World J Biol Psychiatry* 2001, 2(2), 70-82; and Gangadhar et al., *Prog Neuro-Psychopharmacology & Biological Psychiatry* 2006, 30, 910-913. Patients suffering from schizophrenia exhibit lower phosphocreatine levels in the left and right frontal regions of the brain, which are highly correlated with hostility-suspiciousness and anxiety-depression assessment subscales (Deicken et al., *Biol Psychiatry* 1994, 36(8), 503-510; Volz et al., *Biol Psychiatry* 1998, 44, 399-404; and Volz et al., *Biol Psychiatry* 2000, 47, 954-961). Creatine supplementation has accordingly been proposed for treating schizophrenia (see e.g., Lyoo et al., *Psychiatry Res: Neuroimaging* 2003, 123, 87-100).

The efficacy of prodrugs of creatine phosphate analogs and pharmaceutical compositions thereof for treating schizophrenia may be determined by methods known to those skilled in the art. For example, negative, positive, and/or cognitive symptom(s) of schizophrenia may be measured before and after treatment of the patient. Reduction in such symptom(s) indicates that a patient's condition has improved. Improvement in the symptoms of schizophrenia may be assessed using, for example, the Scale for Assessment of Negative Symptoms (SANS), Positive and Negative Symptoms Scale (PANSS) (see, e.g., Andreasen, 1983, *Scales for the Assessment of Negative Symptoms* (SANS), Iowa City, Iowa; and Kay et al., *Schizophrenia Bulletin* 1987, 13, 261-276), and using Cognitive Deficits tests such as the Wisconsin Card Sorting Test (WCST) and other measures of cognitive function (see, e.g., Keshavan et al., *Schizophr Res* 2004, 70(2-3), 187-194; Rush, *Handbook of Psychiatric Measures*, American Psychiatric Publishing 2000; Sajatovic and Ramirez, *Rating Scales in Mental Health*, 2nd ed, Lexi-Comp, 2003, Keefe, et al., *Schizophr Res.* 2004, 68(2-3), 283-97; and Keefe et al., *Neuropsychopharmacology*, 19 Apr. 2006.

The efficacy of prodrugs of creatine phosphate analogs and pharmaceutical compositions thereof may be evaluated using animal models of schizophrenic disorders (see e.g., Geyer and Moghaddam, in "Neuropsychopharmacology," Davis et al., Ed., Chapter 50, 689-701, American College of Neuropsychopharmacology, 2002). For example, conditioned avoidance response behavior (CAR) and catalepsy tests in rats are shown to be useful in predicting antipsychotic activity and EPS effect liability, respectively (Wadenberg et al., *Neuropsychopharmacology*, 2001, 25, 633-641).

Bipolar Disorder

Bipolar disorder is a psychiatric condition characterized by periods of extreme mood. The moods can occur on a spectrum ranging from depression (e.g., persistent feelings of sadness, anxiety, guilt, anger, isolation, and/or hopelessness, disturbances in sleep and appetite, fatigue and loss of interest in usually enjoyed activities, problems concentrating, loneliness, self-loathing, apathy or indifference, depersonalization, loss of interest in sexual activity, shyness or social anxiety, irritability, chronic pain, lack of motivation, and morbid/suicidal ideation) to mania (e.g., elation, euphoria, irritation, and/or suspiciousness). Bipolar disorder is defined and categorized in the *Diagnostic and Statistical Manual of Mental Disorders*, $4^{th}$ Ed., Text Revision (DSM-IV-TR), American Psychiatric Assoc., 200, pages 382-401. Bipolar disorder includes bipolar I disorder, bipolar II disorder, cyclothymia, and bipolar disorder not otherwise specified.

Patients with bipolar depression are shown to have impaired brain high energy phosphate metabolism characterized by reduced levels of phosphocreatine and creatine kinase (Kato et al., *J Affect Disord* 1994, 31(2), 125-33; and Segal et al., *Eur Neuropsychopharmacology* 2007, 17, 194-198) possibly involving mitochondrial energy metabolism (Stork and Renshaw, *Molecular Psychiatry* 2005, 10, 900-919).

Treatment of bipolar disorder can be assessed in clinical trials using rating scales such as the Montgomery-Asberg Depression Rating Scale, the Hamilton Depression Scale, the Raskin Depression Scale, Feighner criteria, and/or Clinical Global Impression Scale Score (Gijsman et al., *Am J Psychiatry* 2004, 161, 1537-1547).

Anxiety

Anxiety is defined and categorized in the *Diagnostic and Statistical Manual of Mental Disorders*, $4^{th}$ Ed., Text Revision (DSM-IV-TR), American Psychiatric Assoc., 200, pages 429-484. Anxiety disorders include panic attack, agoraphobia, panic disorder without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder, and anxiety disorder not otherwise specified. Recent work has documented a correlation of decreased levels of creatine/phosphocreatine in centrum semiovale (a representative region of the cerebral white matter) with the severity of anxiety (Coplan et al., *Neuroimaging*, 2006, 147, 27-39).

Useful animal models for assessing treatment of anxiety include fear-potentiated startle (Brown et al., *J Experimental*

*Psychol*, 1951, 41, 317-327), elevated plus-maze (Pellow et al., *J. Neurosci. Methods* 1985, 14, 149-167; and Hogg, *Pharmacol Biochem Behavior* 1996, 54(1), 21-20), and fear-potentiated behavior in the elevated plus-maze (Korte and De Boer, *Eur J Pharmacol* 2003, 463, 163-175). Genetic animal models of anxiety are known (Toh, *Eur J Pharmacol* 2003, 463, 177-184) as are other animal models sensitive to anti-anxiety agents (Martin, *Acta Psychiatr Scand Suppl* 1998, 393, 74-80).

In clinical trials, efficacy can be evaluated using psychological procedures for inducing experimental anxiety applied to healthy volunteers and patients with anxiety disorders (see e.g., Graeff, et al., *Brazilian J Medical Biological Res* 2003, 36, 421-32) or by selecting patients based on the Structured Clinical interview for DSM-IV Axis I Disorders as described by First et al., Structured Clinical Interview for DSM-IV Axis I Disorders, Patient Edition (SCIDIP), Version 2. Biometrics Research, New York State Psychiatric Institute, New York, 1995. Any of a number of scales can be used to evaluate anxiety and the efficacy of treatment including, for example, the Penn State Worry Questionnaire (Behar et al., *J Behav Ther Exp Psychiatr* 2003, 34, 25-43), the Hamilton Anxiety and Depression Scales, the Spielberger State-Trait Anxiety Inventory, and the Liebowitz Social Anxiety Scale (Hamilton, *J Clin Psychiatry* 1980, 41, 21-24; Spielberger and Vagg, *J Personality Assess* 1984, 48, 95-97; and Liebowitz, *J Clin Psychiatry* 1993, 51, 31-35 (Suppl.)).

Genetic Diseases Affecting the Creatine Kinase System

The intracellular creatine pool is maintained by uptake of creatine from the diet and by endogenous creatine synthesis. Many tissues, especially the liver and pancreas, contain the $Na^+$—$Cl^-$-dependent creatine transport (SLC6A8), which is responsible for active creatine transport through the plasma membrane. Creatine biosynthesis involves the action of two enzymes: L-arginine:glycine amidinotransferase (AGAT) and guanidinoacetate transferase (GAMT). AGAT catalyses the transfer of the amidino group of arginine to glycine to generate ornithine and guanidinoacetate. Guanidino acetate is methylated at the amidino group by GAMT to give creatine (see e.g., Wyss and Kaddurah-Daouk, Phys Rev 2000, 80, 1107-213).

In humans, two genetic errors in creatine biosynthesis and one in creatine transporter are known and involve deficiencies of AGAT, GAMT, and creatine transporter (Schulze, *Cell Biochem*, 2003, 244(1-2), 143-50; Sykut-Cegielska et al., *Acta Biochimica Polonica* 2004, 51(4), 875-882). Patients with disorders of creatine synthesis have systemic depletion of creatine and creatine phosphate. Patients affected with AGAT deficiency can show mental and motor retardation, severe delay in speech development, and febrile seizures (Item et al., *Am J Hum Genet*. 2001, 69, 1127-1133). Patients affected with GAMT deficiency can show developmental delay with absence of active speech, autism with self-injury, extra pyramidal symptoms, and epilepsy (Stromberger et al., *J Inherit Metab Dis* 2003, 26, 299-308). Patients with creatine transporter deficiency exhibit intracellular depletion of creatine and creatine phosphate. The gene encoding the creatine transporter is located on the X-chromosome, and affected male patients show mild to severe mental retardation with affected females having a milder presentation (Salomons et al., *J. Inherit Metab Dis* 2003, 26, 309-18; Rosenberg et al., *Am J Hum Genet* 2004, 75, 97-105; deGrauw et al., *Neuropediatrics* 2002, 33(5), 232-238; Clark et al., *Hum Genet*, 2006, April).

Creatine supplementation in dosages from about 350 mg to 2 g/kg body weight per day have been shown effective in resolving the clinical symptoms of AGAT or GAMT deficiencies (see e.g., Schulze, *Cell Biochem*, 2003, 244(1-2), 143-50). However, unlike in patients with GAMT and AGAT deficiency, in patients with creatine transporter deficiency oral creatine supplementation does not result in an increase in brain creatine levels (see Stockler-Ipsiroglu et al., in *Physician's Guide to the Treatment and Follow up of Metabolic Diseases*, eds Blau et al., Springer Verlag, 2004).

Muscle Fatigue

During high-intensity exercise, ATP hydrolysis is initially buffered by creatine phosphate via the creatine kinase reaction (Kongas and van Beek, $2^{nd}$ *Int. Conf. Systems Biol* 2001, Los Angeles Calif., Omnipress, Madison, Wis., 198-207; and Walsh et al., *J Physiol* 2001, 537.3, 971-78, each of which is incorporated by reference herein in its entirety). During exercise, whereas creatine phosphate is available instantaneously for ATP regeneration, glycolysis is induced with a delay of a few seconds, and stimulation of mitochondrial oxidative phosphorylation is delayed even further. Because the creatine phosphate stores in muscle are limited, during high-intensity exercise, creatine phosphate is depleted within about 10 seconds. It has been proposed that muscle performance can be enhanced by increasing the muscle stores of creatine phosphate and thereby delay creatine phosphate depletion. Although creatine and/or creatine phosphate supplementation may improve muscle performance in intermittent, supramaximal exercise, there is no indication that supplementation enhances endurance performance. On the other hand, intravenous injection of creatine phosphate appears to improve exercise tolerance during prolonged submaximal exercise (Clark, *J Athletic Train*, 1997, 32, 45-51, which is incorporated by reference herein in its entirety).

Muscle Strength

Dietary creatine supplementation in normal healthy individuals has beneficial side effects on muscle function, and as such its use by amateur and professional athletics has increased. There is evidence to suggest that creatine supplementation can enhance overall muscle performance by increasing the muscle store of creatine phosphate, which is the most important energy source for immediate regeneration of ATP in the first few seconds of intense exercise, by accelerating restoration of the creatine phosphate pool during recovery periods, and by depressing the degradation of adenosine nucleotides and possibly also accumulation of lactate during exercise (see e.g., Wyss and Kaddurah-Daouk, *Physiol Rev* 2000, 80(3), 1107-1213). However, in normal healthy individuals, the continuous and prolonged use of creatine fails to maintain elevated creatine and creatine phosphate in muscle (see e.g., Juhn et al., *Clin J Sport Med* 1998, 8, 286-297; Terjung et al., *Med Sci Sports Exerc* 2000, 32, 706-717; and Vandenberghe et al., *J Appl Physiol* 1997, 83, 2055-2063, each of which is incorporated by reference herein in its entirety), possibly as a result of the down regulation of the creatine transporter activity and the transporter protein content (Snow and Murphy, *Mol Cell Biochem* 2001, 224(1-2), 169-181, which is incorporated by reference herein in its entirety). Thus, prodrugs of creatine phosphate analogs provided by the present disclosure may be used to maintain, restore, and/or enhance muscle strength in a mammal, and in particular a human.

The efficacy of administering a compound of Formula (I) or Formula (II) for maintaining, restoring, and/or enhancing muscle strength may be assessed using animal and human models and clinical studies. Animal models that can be used for evaluation of muscle strength are disclosed, for example, in Wirth et al., *J Applied Physiol* 2003, 95, 402-412 and Timson, *J. Appl Physiol* 1990, 69(6), 1935-1945. Muscle strength can be assessed in humans using methods disclosed, for example, in Oster, U.S. Application Publication No. 2007/0032750, Engsberg et al., U.S. Application Publication No. 2007/0012105, and/or using other methods known to those skilled in the art.

Organ and Cell Viability

In certain embodiments, the isolation of viable brain, muscle, pancreatic or other cell types for research or cellular transplant can be enhanced by perfusing cells and/or contacting cells with an isolation or growth media containing a creatine phosphate analog prodrug. In certain embodiments, the viability of a tissue, organ, or cell can be improved by contacting the tissue, organ or, cell with an effective amount of a compound of Formula (I) and/or Formula (II) or pharmaceutical composition thereof.

Diseases Related to Glucose Level Regulation

Administration of creatine phosphate reduces plasma glucose levels, and therefore can be useful in treating diseases related to glucose level regulation such as hyperglycemia, insulin dependent or independent diabetes, and related diseases secondary to diabetes (Kaddurah-Daouk et al., U.S. Application Publication No 2005/0256134).

The efficacy of administering a compound of Formula (I) or Formula (II) for treating diseases related to glucose level regulation may be assessed using animal and human models and clinical studies. Compounds can be administered to animals such as rats, rabbits or monkeys, and plasma glucose concentrations determined at various times (see e.g., Kaddurah-Daouk and Teicher, U.S. Application Publication No. 2003/0232793). The efficacy of compounds for treating insulin dependent or independent diabetes and related diseases secondary to diabetes can be evaluated using animal models of diabetes such as disclosed, for example, in Shafrir, "Animal Models of Diabetes," Ed., 2007, CRC Press; Mordes et al., "Animal Models of Diabetes," 2001, Harwood Academic Press; Mathe, *Diabete Metab* 1995, 21(2), 106-111; and Rees and Alcolado, *Diabetic Med.* 2005, 22, 359-370.

Dose

Compounds of Formula (I) and/or Formula (II) or pharmaceutically acceptable salts, or pharmaceutically acceptable solvates of any of the foregoing can be administered to treat diseases or disorders associated with a dysfunction in energy metabolism.

The amount of a compound of Formula (I) and/or Formula (II) that will be effective in the treatment of a particular disease, disorder, or condition disclosed herein will depend on the nature of the disease, disorder, or condition, and can be determined by standard clinical techniques known in the art. In addition, in vitro or in vivo assays may optionally be employed to help identify optimal dosage ranges. The amount of a compound administered can depend on, among other factors, the patient being treated, the weight of the patient, the health of the patient, the disease being treated, the severity of the affliction, the route of administration, the potency of the compound, and the judgment of the prescribing physician.

For systemic administration, a therapeutically effective dose can be estimated initially from in vitro assays. For example, a dose can be formulated in animal models to achieve a beneficial circulating composition concentration range. Initial doses can also be estimated from in vivo data, e.g., animal models, using techniques that are known in the art. Such information can be used to more accurately determine useful doses in humans. One having ordinary skill in the art can optimize administration to humans based on animal data.

Creatine occurs naturally in the human body and is partly synthesized by the kidney, pancreas, and liver (approximately 1-2 grams per day), and partly ingested with food (approximately 1-5 grams per day). Cells actively take up creatine via the creatine transporter. Within a cell, creatine kinase phosphorylates creatine to form a pool of creatine phosphate that can act as a temporal and spatial energy buffer.

Creatine, creatine phosphate, and analogs thereof can be administered in a high dose without adverse side effects. For example, creatine monohydrate has been administered to athletes and body builders in amounts ranging from 2-3 gm/day, and creatine phosphate has been administered to patients with cardiac diseases by intravenous injection up to 8 gm/day, without adverse side effects. Animals fed a diet containing up to 1% cyclocreatine also do not exhibit adverse effects (see, e.g., Griffiths and Walker, *J. Biol. Chem* 1976, 251(7), 2049-2054; Annesley et al., *J Biol Chem* 1978, 253(22), 8120-25; Lillie et al., *Cancer Res* 1993, 53, 3172-78; and Griffiths, *J Biol Chem* 1976, 251(7), 2049-54).

In certain embodiments, a therapeutically effective dose of a compound of Formula (I) and/or Formula (II) can comprise from about 1 mg-equivalents to about 20,000 mg-equivalents of a creatine phosphate analog per day, from about 100 mg-equivalents to about 12,000 mg-equivalents of creatine phosphate analog per day, from about 1,000 mg-equivalents to about 10,000 mg-equivalents of creatine phosphate analog per day, and in certain embodiments, from about 4,000 mg-equivalents to about 8,000 mg-equivalents of creatine phosphate analog per day.

A dose can be administered in a single dosage form or in multiple dosage forms. When multiple dosage forms are used the amount of compound contained within each dosage form can be the same or different. The amount of a compound of Formula (I) and/or Formula (II) contained in a dose can depend on the route of administration and whether the disease, disorder, or condition in a patient is effectively treated by acute, chronic, or a combination of acute and chronic administration.

In certain embodiments an administered dose is less than a toxic dose. Toxicity of the compositions described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a pharmaceutical composition can exhibit a high therapeutic index. The data obtained from these cell culture assays and animal studies can be used in formulating a dosage range that is not toxic for use in humans. A dose of a pharmaceutical composition provided by the present disclosure can be within a range of circulating concentrations in for example the blood, plasma, or central nervous system, that include the effective dose and that exhibits little or no toxicity. A dose may vary within this range depending upon the dosage form employed and the route of administration utilized.

During treatment, a dose and dosing schedule can provide sufficient or steady state levels of an effective amount of a creatine phosphate analog to treat a disease. In certain embodiments, an escalating dose can be administered.

Administration

A compound of Formula (I) and/or Formula (II), a pharmaceutically acceptable salt thereof, or a pharmaceutically acceptable solvate of any of the foregoing, or a pharmaceutical composition of any of the foregoing can be administered by any appropriate route. In certain embodiments, a compound of Formula (I) and/or Formula (II) can be administered intermittently or continuously. Examples of suitable routes of administration include, but are not limited to, intradermal, intramuscular, intraperitoneal, intravenous, subcutaneous, intranasal, epidural, oral, sublingual, intranasal, intracerebral, intravaginal, transdermal, rectally, inhalation, or topically. Administration can be systemic or local. Administration can be bolus injection, continuous infusion, or by absorption through epithelial or mucocutaneous linings, e.g., oral mucosa, rectal, and intestinal mucosa, etc.

In certain embodiments, it may be desirable to introduce a compound of Formula (I) and/or Formula (II), a pharmaceutically acceptable salt, or a pharmaceutical acceptable solvate of any of the foregoing, or a pharmaceutical composition of any of the foregoing directly into the central nervous system by any suitable route, including intraventricular, intrathecal, and epidural injection. Intraventricular injection can be facilitated by the use of an intraventricular catheter, for example, attached to a reservoir, such as an Ommaya reservoir.

In certain embodiments, a compound of Formula (I) and/or Formula (II), a pharmaceutically acceptable salt thereof, or a pharmaceutically acceptable solvate of any of the foregoing, or a pharmaceutical composition of any of the foregoing can be administered parenterally, such as by injection, including, for example, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection or infusion.

A compound of Formula (I) and/or Formula (II), a pharmaceutically acceptable salt thereof, or a pharmaceutically acceptable solvate of any of the foregoing, or a pharmaceutical composition of any of the foregoing can be administered systemically and/or locally to a specific organ.

In certain embodiments, a compound of Formula (I) and/or Formula (II) or pharmaceutical composition thereof can be administered as a single, one time dose or chronically. By chronic it is meant that the methods and compositions of the invention are practiced more than once to a given individual. For example, chronic administration can be multiple doses of a pharmaceutical composition administered to an animal, including an individual, on a daily basis, twice daily basis, or more or less frequently, as will be apparent to those of skill in the art. In another embodiment, the methods and compositions are practiced acutely. By acute it is meant that the methods and compositions of the invention are practiced in a time period close to or contemporaneous with the ischemic or occlusive event. For example, acute administration can be a single dose or multiple doses of a pharmaceutical composition administered at the onset of an ischemic or occlusive event such as acute myocardial infarction, upon the early manifestation of an ischemic or occlusive event such as, for example, a stroke, or before, during or after a surgical procedure. A time period close to or contemporaneous with an ischemic or occlusive event will vary according to the ischemic event but can be, for example, within about 30 minutes of experiencing the symptoms of a myocardial infarction, stroke, or intermittent claudication. In certain embodiments, acute administration is administration within about an hour of the ischemic event. In certain embodiments, acute administration is administration within about 2 hours, about 6 hours, about 10 hours, about 12 hours, about 15 hours or about 24 hours after an ischemic event.

In certain embodiments, a compound of Formula (I) and/or Formula (II) or pharmaceutical composition thereof can be administered chronically. In certain embodiments, chronic administration can include several intravenous injections administered periodically during a single day. In certain embodiments, chronic administration can include one intravenous injection administered as a bolus or as a continuous infusion daily, about every other day, about every 3 to 15 days, about every 5 to 10 days, and in certain embodiments, about every 10 days.

Combination Therapy

In certain embodiments, a compound of Formula (I) and/or Formula (II), a pharmaceutically acceptable salt thereof, or pharmaceutically acceptable solvate of any of the foregoing, can be used in combination therapy with at least one other therapeutic agent. A compound of Formula (I) and/or Formula (II) and other therapeutic agent(s) can act additively or, and in certain embodiments, synergistically. In some embodiments, a compound of Formula (I) and/or Formula (II) can be administered concurrently with the administration of another therapeutic agent, such as for example, a compound for treating a disease associated with a dysfunction in energy metabolism; treating muscle fatigue; enhancing muscle strength and endurance; increasing the viability of organ transplants; and improving the viability of isolated cells. In some embodiments, a compound of Formula (I) and/or Formula (II), a pharmaceutically acceptable salt, or a pharmaceutically acceptable solvate of any of the foregoing can be administered prior to or subsequent to administration of another therapeutic agent, such as for example, a compound for treating a disease associated with a dysfunction in energy metabolism such as ischemia, ventricular hypertrophy, a neurodegenerative disease such as ALS, Huntington's disease, Parkinson's disease, or Alzheimer's disease, surgery related ischemic tissue damage, and reperfusion tissue damage; treating multiple sclerosis (MS), treating a psychotic disorder such as schizophrenia, bipolar disorder, or anxiety; treating muscle fatigue; enhancing muscle strength and endurance; increasing the viability of organ transplants; and improving the viability of isolated cells.

Pharmaceutical compositions provided by the present disclosure can include, in addition to one or more compounds provided by the present disclosure, one or more therapeutic agents effective for treating the same or different disease, disorder, or condition.

Methods provided by the present disclosure include administration of one or more compounds or pharmaceutical compositions provided by the present disclosure and one or more other therapeutic agents provided that the combined administration does not inhibit the therapeutic efficacy of the one or more compounds provided by the present disclosure and/or does not produce adverse combination effects.

In certain embodiments, compositions provided by the present disclosure can be administered concurrently with the administration of another therapeutic agent, which can be part of the same pharmaceutical composition or dosage form as, or in a different composition or dosage form from, that containing the compounds provided by the present disclosure. In certain embodiments, compounds provided by the present disclosure can be administered prior or subsequent to administration of another therapeutic agent. In certain embodiments of combination therapy, the combination therapy comprises alternating between administering a composition provided by the present disclosure and a composition comprising another therapeutic agent, e.g., to minimize adverse side effects associated with a particular drug. When a compound provided by the present disclosure is administered concurrently with another therapeutic agent that potentially can produce adverse side effects including, but not limited to, toxicity, the therapeutic agent can advantageously be administered at a dose that falls below the threshold at which the adverse side effect is elicited.

In certain embodiments, compounds or pharmaceutical compositions provided by the present disclosure include, or can be administered to a patient together with, another compound for treating Parkinson's disease such as amantadine, benztropine, bromocriptine, levodopa, pergolide, pramipexole, ropinirole, selegiline, trihexyphenidyl, or a combination of any of the foregoing.

In certain embodiments, compounds or pharmaceutical compositions provided by the present disclosure include, or can be administered to a patient together with, another compound for treating Alzheimer's disease such as donepezil, galantamine, memantine, rivastigmine, tacrine, or a combination of any of the foregoing.

In certain embodiments, compounds or pharmaceutical compositions provided by the present disclosure include, or can be administered to a patient together with, another compound for treating ALS such as riluzole.

In certain embodiments, compounds or pharmaceutical compositions provided by the present disclosure include, or can be administered to a patient together with, another compound for treating ischemic stroke such as aspirin, nimodipine, clopidogrel, pravastatin, unfractionated heparin, eptifibatide, a β-blocker, an angiotensin-converting enzyme (ACE) inhibitor, enoxaparin, or a combination of any of the foregoing.

In certain embodiments, compounds or pharmaceutical compositions provided by the present disclosure include, or can be administered to a patient together with, another compound for treating ischemic cardiomyopathy or ischemic heart disease such as ACE inhibitors such as ramipril, captopril, and lisinopril; β-blockers such as acebutolol, atenolol, betaxolol, bisoprolol, carteolol, nadolol, penbutolol, propranolol, timolol, metoprolol, carvedilol, and aldosterone; diuretics; digitoxin, or a combination of any of the foregoing.

In certain embodiments, compounds or pharmaceutical compositions provided by the present disclosure include, or can be administered to a patient together with, another compound for treating a cardiovascular disease such as, blood-thinners, cholesterol lowering agents, anti-platelet agents, vasodilators, beta-blockers, angiotensin blockers, digitalis and is derivatives, or combinations of any of the foregoing.

In certain embodiments, compounds or pharmaceutical compositions provided by the present disclosure include, or can be administered to a patient together with, another compound for treating MS. Examples of drugs useful for treating MS include corticosteroids such as methylprednisolone; IFN-β such as IFN-β1a and IFN-β1b; glatiramer acetate (Copaxone®); monoclonal antibodies that bind to the very late antigen-4 (VLA-4) integrin (Tysabri®) such as natalizumab; immunomodulatory agents such as FTY 720 sphinogosie-1 phosphate modulator and COX-2 inhibitors such as BW755c, piroxicam, and phenidone; and neuroprotective treatments including inhibitors of glutamate excitotoxicity and iNOS, free-radical scavengers, and cationic channel blockers; memantine; AMPA antagonists such as topiramate; and glycine-site NMDA antagonists (Virley, NeruoRx 2005, 2(4), 638-649, and references therein; and Kozachuk, U.S. Application Publication No. 2004/0102525).

In certain embodiments, compounds or pharmaceutical compositions provided by the present disclosure include, or can be administered to a patient together with, another compound for treating schizophrenia. Examples of antipsychotic agents useful in treating schizophrenia include, but are not limited to, acetophenazine, alseroxylon, amitriptyline, aripiprazole, astemizole, benzquinamide, carphenazine, chlormezanone, chlorpromazine, chlorprothixene, clozapine, desipramine, droperidol, aloperidol, fluphenazine, flupenthixol, glycine, oxapine, mesoridazine, molindone, olanzapine, ondensetron, perphenazine, pimozide, prochlorperazine, procyclidine, promazine, propiomazine, quetiapine, remoxipride, reserpine, risperidone, sertindole, sulpiride, terfenadine, thiethylperzaine, thioridazine, thiothixene, trifluoperazine, trifluopromazine, trimeprazine, and ziprasidone. Other antipsychotic agents useful for treating symptoms of schizophrenia include amisulpride, balaperidone, blonanserin, butaperazine, carphenazine, eplavanserin, iloperidone, lamictal, onsanetant, paliperidone, perospirone, piperacetazine, raclopride, remoxipride, sarizotan, sonepiprazole, sulpiride, ziprasidone, and zotepine; serotonin and dopamine (5HT/D2) agonists such as asenapine and bifeprunox; neurokinin 3 antagonists such as talnetant and osanetant; AMPAkines such as CX-516, galantamine, memantine, modafinil, ocaperidone, and tolcapone; and α-amino acids such as D-serine, D-alanine, D-cycloserine, and N-methylglycine.

In certain embodiments, compounds or pharmaceutical compositions provided by the present disclosure include, or can be administered to a patient together with, another compound for treating bipolar disorder such as aripiprazole, carbamazepine, clonazepam, clonidine, lamotrigine, quetiapine, verapamil, and ziprasidone.

In certain embodiments, compounds or pharmaceutical compositions provided by the present disclosure include, or can be administered to a patient together with, another compound for treating anxiety such as alprazolam, atenolol, busipirone, chlordiazepoxide, clonidine, clorazepate, diazepam, doxepin, escitalopram, halazepam, hydroxyzine, lorazepam, prochlorperazine, nadolol, oxazepam, paroxetine, prochlorperazine, trifluoperazine, and venlafaxine.

EXAMPLES

The following examples describe in detail assays for the characterization of compounds of Formula (I) and/or Formula (II), and uses of compounds of Formula (I) and/or Formula (II). It will be apparent to those skilled in the art that many modifications, both to materials and methods, may be practiced without departing from the scope of the disclosure.

Example 1

Methods for Determination of Enzymatic Cleavage of Prodrugs In Vitro

For creatine phosphate prodrugs, it is generally desirable that the prodrug remains intact (i.e., uncleaved) while in the systemic circulation and be cleaved (i.e., to release the parent drug) in the target tissue. A useful level of stability can at least in part be determined by the mechanism and pharmacokinetics of the prodrug. A useful level of liability can at least in part also be determined by the pharmacokinetics of the prodrug and parent drug in the systemic circulation and/or in the gastrointestinal tract, if orally administered. In general, prodrugs that are more stable in pancreatin or colonic wash assay and are more labile in a rat plasma, human plasma, rat liver S9, and/or human liver S9 preparations can be useful as an orally administered prodrug. In general, prodrugs that are more stable in rat plasma, human plasma, rat liver S9, and/or human liver S9 preparations and which are more labile in cell homogenate preparations, such Caco-2 S9 preparations, can be useful as systemically administered prodrugs and/or can be more effective in delivering a prodrug to a target tissue. In general, prodrugs that are more stable in different pH physiological buffers can be more useful as prodrugs. In general, prodrugs that are more labile in cell homogenate preparations, such Caco-2 S9 preparations, can be intracellularly cleaved to release the parent drug to a target tissue. The results of tests, such as those described in this example, for determining the enzymatic or chemical cleavage of prodrugs in vitro can be used to select prodrugs for in vivo testing.

The stabilities of prodrugs can be evaluated in one or more in vitro systems using a variety of preparations following methods known in the art. Tissues and preparations are obtained from commercial sources (e.g., Pel-Freez Biologicals, Rogers, Ark., or GenTest Corporation, Woburn, Mass.). Experimental conditions useful for the in vitro studies are described in Table 1. Prodrug is added to each preparation in triplicate.

For preparations that contain alkaline phosphatases, prodrug is tested in the presence and absence of a phosphatase inhibitor cocktail (Sigma). Samples are incubated at 37° C. for times ranging from 30 minutes to 24 hours. At each time point, samples are quenched with 50% ethanol. Baseline concentrations of prodrug are determined by adding the compound directly to the 50% ethanol/preparation mixture (t=0). Samples are centrifuged at 14,000 rpm for 15 minutes, and concentrations of intact prodrug and released parent drug are determined using LC/MS/MS. This stability of prodrugs towards specific enzymes (e.g., peptidases, etc.) is also assessed in vitro by incubation with the purified enzyme.

Pancreatin stability studies are conducted by incubating prodrug (5 μM) with 1% (w/v) pancreatin (Sigma, P-1625, from porcine pancreas) in 0.025 M Tris buffer containing 0.5 M NaCl (pH 7.5) at 37° C. The reaction is stopped by addition of 3 volumes of 50% ethanol. After centrifugation at 14,000 rpm for 15 min, the supernatant is removed and analyzed by LC/MS/MS.

To determine stability in Caco-2 homogenate S9, Caco-2 cells are grown for 21 days prior to harvesting. Culture medium is removed and cell monolayers are rinsed and scraped off into ice-cold 10 mM sodium phosphate/0.15 M potassium chloride, pH 7.4. Cells are lysed by sonication at 4° C. using a probe sonicator. Lysed cells are then transferred into 1.5 mL centrifuge vials and centrifuged at 9,000 g for 20 min at 4° C. The resulting supernatant (Caco-2 cell homogenate S9 fraction) is aliquoted into 0.5 mL vials and stored at −80° C. until used.

For stability studies, prodrug (5 μM) is incubated in Caco-2 homogenate S9 fraction (0.5 mg/mL in O.1M Tris buffer, pH 7.4) at 37° C. Triplicate samples are quenched at each time point with 50% ethanol. The initial (t=0) concentration of prodrug is determined by adding 5 μM prodrug directly to a 50% ethanol/Caco-2 homogenate mixture. Samples are subjected to LC/MS/MS analysis to determine concentrations of prodrug and parent drug.

To determine prodrug stability in rat plasma, compound (5 μM) is incubated in undiluted rat plasma. Triplicate samples are quenched at each time point with 50% ethanol. The initial (t=0) concentration of prodrug is determined by adding 5 μM prodrug directly to a 50% ethanol/rat plasma mixture. Samples are subjected to LC/MS/MS analysis to determine concentrations of prodrug and parent drug.

For rat S9 stability studies, prodrug (5 μM) is incubated in rat liver S9 homogenate (0.5 mg/mL in 0.1M potassium phosphate buffer, pH 7.4, 1 mM NADPH) at 37° C. Triplicate samples are quenched at each time point with 50% ethanol. The initial (t=0) concentration of prodrug is determined by adding 5 μM prodrug directly to a 50% ethanol/S9 homogenate mixture. Samples are subjected to LC/MS/MS analysis to determine concentrations of prodrug and parent drug.

Three buffers are used to determine the chemical stability of prodrug: (1) 0.1M potassium phosphate, 0.5 M NaCl, pH 2.0, (2) 0.1 M Tris-HCl, 0.5 M NaCl, pH 7.4, and (3) 0.1 M Tris-HCl, 0.5 M NaCl, pH 8.0. Prodrug (5 μM) is added to each buffer in triplicate. Samples are quenched at each time point with 50% ethanol. The initial (t=0) concentration of prodrug is determined by adding 5 μM prodrug directly to a 50% ethanol/pH Buffer mixture. Samples are subjected to LC/MS/MS analysis to determine concentrations of prodrug and parent drug.

TABLE 1

Standard Conditions for Prodrug In Vitro Metabolism Studies

| Preparation | Substrate Concentration | Cofactors |
| --- | --- | --- |
| Rat Plasma | 2.0 μM | None |
| Human Plasma | 2.0 μM | None |
| Rat Liver S9 (0.5 mg/mL) | 2.0 μM | NADPH* |
| Human Liver S9 (0.5 mg/mL) | 2.0 μM | NADPH* |
| Human Intestine S9 (0.5 mg/mL) | 2.0 μM | NADPH* |
| Caco-2 Homogenate | 5.0 μM | None |
| Pancreatin | 5.0 μM | None |

*NADPH generating system, e.g., 1.3 mM NADP$^+$, 3.3 mM glucose-6-phosphate, 0.4 U/mL glucose-6-phosphate dehydrogenase, 3.3 mM magnesium chloride and 0.95 mg/mL potassium phosphate, pH 7.4.

Example 2

In Vitro Determination of Caco-2 Cellular Permeability of Prodrugs

The passive permeability of creatine phosphate analog prodrugs is assessed in vitro using standard methods well known in the art (see, e.g., Stewart, et al., *Pharm. Res.*, 1995, 12, 693). For example, passive permeability can be evaluated by examining the flux of a prodrug across a cultured polarized cell monolayer (e.g., Caco-2 cells).

Caco-2 cells obtained from continuous culture (passage less than 28) are seeded at high density onto Transwell polycarbonate filters. Cells are maintained with DMEM/10% fetal calf serum+0.1 mM nonessential amino acids+2 mM L-Gln, 5% $CO_2$/95% $O_2$, 37° C. until the day of the experiment. Permeability studies are conducted at pH 6.5 apically (in 50 mM MES buffer containing 1 mM $CaCl_2$, 1 mM $MgCl_2$, 150 mM NaCl, 3 mM KCl, 1 mM $NaH_2PO_4$, 5 mM glucose) and pH 7.4 basolaterally (in Hank's balanced salt solution containing 10 mM HEPES) in the presence of efflux pump inhibitors (250 μM MK-571, 250 μM verapamil, 1 mM Ofloxacin). Inserts are placed in 12 or 24 well plates containing buffer and incubated for 30 min at 37° C. Prodrug (100 μM, 250 μM, 300 μM, or 500 μM) is added to the apical or basolateral compartment (donor) and concentrations of prodrug and/or released parent drug (creatine phosphate) in the opposite compartment (receiver) are determined at intervals over 1 hour using LC/MS/MS. Values of apparent permeability ($P_{app}$) are calculated using the equation:

$$P_{app} = V_r(dC/dt)/(AC_o)$$

where $V_r$ is the volume of the receiver compartment in mL; dC/dt is the total flux of prodrug and parent drug (μM/s), determined from the slope of the plot of concentration in the receiver compartment versus time; $C_o$ is the initial concentration of prodrug in μM; and A is the surface area of the membrane in cm². In certain embodiments, prodrugs with significant transcellular permeability exhibit a value of $P_{app}$ of $\geq 1 \times 10^{-6}$ cm/s, in certain embodiments, a value of $P_{app}$ of $\geq 1 \times 10^{-5}$ cm/s, and in certain embodiments a value of $P_{app}$ of $\geq 5 \times 10^{-5}$ cm/s.

Example 3

Uptake by Caco-2 and HEK-2 Cells

Caco-2 or HEK Peaks are seeded onto poly-lysine coated 24-well plastic cell culture plates at 250,000 and 500,000 cells/well, respectively. Cells are incubated overnight at 37° C. Prodrug is added to each well in 1 mL fresh media. Each concentration of prodrug is tested in triplicate. Media only is added to the control wells. At each time point, cells are washed four times in Hank's Balanced Salt Solution. Cells are lysed and compound is extracted by adding 200 μL 50% ethanol to each well for 20 minutes at room temperature. Aliquots of the ethanol solution are moved to a 96-well V-bottom plate and centrifuged at 5,700 rpm for 20 minutes at 4° C. Supernatant is analyzed by LC/MS/MS to determine the concentration of prodrug, parent compound, and/or other compound.

Example 4

Expression of SMVT in Mammalian Cells

SMVT was subcloned into a plasmid that allows for inducible expression by tetracycline (TREX plasmid, Invitrogen Inc., Carlsbad Calif.). The SMVT expression plasmid was transfected into a human embryonic kidney (HEK) cell line and stable clones were isolated by G418 selection and flow activated cell sorting (FACS). Biotin uptake in a SMVT-HEK cell clone was used for validation. SMVT-HEK/TREX cells were plated in 96-well plates at 100,000 cells/well at 37° C. for 24 hours and tetracycline (1 μg/mL) was added to each well for an additional 24 hours to induce SMVT transporter expression. Radiolabeled ³H-biotin (~100,000 cpm/well) was added to each well. Plates were incubated at room temperature for 10 min. Excess ³H-biotin was removed and cells were washed three times with a 96-well plate washer with cold assay buffer. Scintillation fluid was added to each well, and the plates were sealed and counted in a 96-well plate-based scintillation counter.

Similar methods can be used to prepare HEK cells expressing other transporters, or other cell lines expressing SMVT or other transporters.

The GenBank accession number for human SMVT is NM_021095, which is incorporated by reference herein. Reference to the SMVT transporter includes the amino acid sequence described in or encoded by the GenBank reference number NM_021095, and, allelic, cognate and induced variants and fragments thereof retaining essentially the same transporter activity. Usually such variants show at least 90% sequence identity to the exemplary GenBank nucleic acid or amino acid sequence. Substrates for SMVT are compounds containing a free carboxylic acid and a short alkyl chain, e.g., $C_{1-6}$ alkyl, ending in a cyclic or branched group. Example os SMVT substrates include biotin, pantothenic acid, and 4-phenylbutyric acid.

Example 5

Competition Assays Using SMVT

To determine if a test compound binds the SMVT transporter, a competition binding assay was developed. This assay measures how different concentrations of a test compound block the uptake of a radiolabeled substrate such as biotin or pantothenic acid. The half-maximal inhibitory concentration ($IC_{50}$) for inhibition of transport of a substrate by a test compound is an indication of the affinity of the test compound for the SMVT transporter. If the test compound binds SMVT competitively with the radiolabeled substrate, less of the radiolabeled substrate is transported into the HEK cells. For test compounds that do not interact with SMVT in a manner competitive with substrates the curve remains an essentially flat line, i.e., there is no dose response seen. The amount of radiolabeled substrate taken up by the cells is measured by lysing the cells and measuring the radioactive counts per minute. Competition binding studies are performed as follows. SMVT-HEK/TREX cells are plated in 96-well plates at 100,000 cells/well at 37° C. for 24 hours and tetracycline (1 μg/mL) is added to each well for an additional 24 hours to induce SMVT transporter expression. Radiolabeled ³H-biotin (~100,000 cpm/well) is added to each well in the presence and absence of various concentrations of unlabeled biotin or pantothenic acid in duplicate or triplicate. Plates are incubated at room temperature for 10 min. Excess ³H-biotin is removed and cells are washed three times using a 96-well plate washer with cold assay buffer. Scintillation fluid is added to each well, and the plates are sealed and counted in a 96-well plate-based scintillation counter. Data is graphed and analyzed using non-linear regression analysis with Prism Software (GraphPad, Inc., San Diego, Calif.).

Example 6

Treatment of HEK—SMVT Cells With Test Compounds

Uptake of unlabeled compounds is measured in HEK cells stably expressing SMVT. Cells are plated at a density of 250,000 cells/well in polylysine coated 24-well tissue culture plates. Twenty-four hours later cells are treated with tetracycline (1 μg/ml) to induce SMVT expression, or left untreated. The following day (approximately 48 hours after seeding), the assay is performed. Test compounds (0.1 mM final concentration) are added to a buffered saline solution (HBSS), and 0.5 mL of each test solution is added to each well. Cells are allowed to take up the test compounds for 1 or 3 hours. Test solution is aspirated and cells washed 4 times with ice-cold HBSS. Cells are then lysed with a 50% ethanol solution (0.2 mL/well) at room temperature for 15 minutes. The lysate is centrifuged at 5477×g for 15 minutes at 4° C. to remove cell debris. The concentration of test compounds in the cell is determined by analytical LC/MS/MS. Transporter specific uptake is determined by comparison with control cells lacking transporter expression.

Example 7

Effect of Treatment on the Creatine Kinase System

HEK cells expressing SMVT are treated with buffer, a creatine phosphate analog prodrug (100 µM), creatine (100 µM), creatine phosphate analog (100 µM), or creatine phosphate (100 µM) for a specified time period according to the protocol of Example 6. Following treatment, the intracellular concentrations of the creatine phosphate analog prodrug, creatine phosphate, ATP, and creatine are measured by analytical LC/MS/MS.

Example 8

Restoration of Cellular Energy Homeostasis Following Sodium Azide Treatment An adaptation of the methods described by Weinstock and Shoham, *Neural Transm.* 2004, 111(3), 347-66, is used to evaluate the protective effects on intracellular energy homeostasis of compounds of Formula (I) and Formula (II).

The HEK TREX SMVT cell line is seeded at 250 k per well in a 24-well polylysine coated tissue culture plate. The next day, cells are treated with doxycycline (1 µg/mL) to express the SMVT transporter, which is required for efficient uptake of the creatine phosphate analog prodrug, e.g., a compound of Formula (I) or Formula (II), tested. The cells are incubated and assayed on the following day. Cells are washed twice with HBSS buffer lacking glucose. Cells are then incubated for 20 min at 37° C. in a 5% $CO_2$ incubator in the same buffer with or without sodium azide. A typical range of sodium azide used in these experiments is from 1 mM to 9 mM. After this time, 300 µM of a prodrug of a creatine phosphate analog is added to the cells, or the cells are left untreated. In some experiments, creatine is used as a comparison. The cells are incubated for an additional 20 min and then washed with buffer. Samples are extracted for 15 min with 50% ethanol and processed for LC/MS/MS to detect the creatine phosphate, creatine phosphate analog, and ATP levels. Increased creatine phosphate and ATP levels in sodium azide treated cells following exposure to a prodrug of a creatine phosphate analog indicates that the prodrug of a creatine phosphate analog is capable of restoring cellular energy homeostasis.

Example 9

Protection Against 3-Nitropropionic Acid Induced Toxicity

An adaptation of the methods described by Brouillet et al., *J. Neurochem* 2005, 95(6), 1521-40, is used to evaluate the protective effects on intracellular energy homeostasis of compounds of Formula (I) and Formula (II).

The rat cardiomyoblast cell line H9c2 is obtained from ATCC (#CRL-1446). A 20 mM stock solution of 3-nitropropionic acid (3-NP) is prepared immediately before use in normal media (DMEM/High glucose (4.5 g/L)/10% FBS/6 mM L-glutamine/PSF) and the pH is adjusted to 7.4 by dropwise addition of 1N sodium hydroxide. A 40 mM stock solution of a prodrug of a creatine phosphate analog, e.g. a compound of Formula (I) or Formula (II), is prepared in DMSO, and creatine is dissolved directly in serum-free media at 10 mM.

To measure the extent of cellular protection provided by the creatine phosphate analog prodrug and creatine phosphate analog against 3-NP toxicity, H9c2 cells are plated in 96-well clear-bottom black tissue culture plates at 10 K cells per well in normal media and incubated overnight at 37° C. The following day the media is removed and replaced with serum-free media containing serial dilutions of a prodrug of a creatine phosphate analog or creatine phosphate. The plates are incubated at 37° C. for 2 hours. Media is then removed by aspiration and replaced with normal media containing various concentrations of 3-NP and the plates incubated at 37° C. for an additional 20 hours. To determine the number of viable cells in each well, an equal volume of CellTiter-Glo reagent (Promega) is added and mixed for 10 minutes on a plate shaker at room temperature. Luminescence is measured by reading the plates in a luminometer. The luminescence produced in this assay is proportional to the amount of ATP present, and directly relates to the number of metabolically active cells.

Increased viability of cells exposed to 3-NP and a prodrug of a creatine phosphate analog compared to that of cells exposed to 3-NP and creatine indicates that the prodrug of a creatine phosphate analog has the capacity to maintain cellular energy homeostasis.

Example 10

Pharmacokinetics of Creatine Phosphate Analog Following Colonic Administration of Prodrugs of Creatine Phosphate Analogs in Rats Sustained release oral dosage forms, which release drug slowly over periods of about 6 to about 24 hours, generally release a significant proportion of the dose within the colon. Thus, drugs suitable for use in such dosage forms should be colonically absorbed. This experiment is performed to assess the uptake and resultant levels of a creatine phosphate analog in a biological fluid such as the plasma/blood or cerebrospinal fluid (CSF), following intracolonic administration of a corresponding prodrug of a creatine phosphate analog, such as a compound of Formula (I) or Formula (II) and thereby determine the suitability of a compound of the prodrug of the creatine phosphate analog for use in an oral sustained release dosage form. Bioavailability of a creatine phosphate analog following co-administration of a corresponding prodrug of the creatine phosphate analog can be calculated relative to oral administration and/or to colonic administration of the creatine phosphate analog.

Step A: Administration Protocol

Rats are obtained commercially and are pre-cannulated in both the ascending colon and the jugular vein. Animals are conscious at the time of the experiment. All animals are fasted overnight and until 4 hours post-dosing of a prodrug of a creatine phosphate analog. The prodrug of a creatine phosphate analog is administered as a solution (in water or other appropriate solvent and vehicles) directly into the colon via the cannula at a dose equivalent to about 1 mg to about 200 mg of the prodrug of a creatine phosphate analog per kg body weight. Blood samples (0.3 mL) are obtained from the jugular cannula at intervals over 8 hours and are immediately quenched with sodium metabisulfite or other appropriate antioxidant to prevent oxidation of the creatine phosphate analog and corresponding prodrug. Blood samples can be further quenched with methanol/perchloric acid to prevent hydrolysis of the creatine phosphate analog and corresponding prodrug. Blood samples are analyzed as described below. Samples can also be taken from the CSF or other appropriate biological fluid.

Step B: Sample Preparation for Colonically Absorbed Drug

Methanol/perchloric acid (300 μL) is added to blank 1.5 mL Eppendorf tubes. Rat blood (300 μL) is collected into EDTA tubes containing 75 μL of sodium metabisulfite at different times and vortexed to mix. A fixed volume of blood (100 μL) is immediately added into the Eppendorf tube and vortexed to mix. Ten microliters of a standard stock solution of the creatine phosphate analog (0.04, 0.2, 1, 5, 25, and 100 μg/mL) and 10 μL of the 10% sodium metabisulfite solution are added to 80 μL of blank rat blood to make up a final calibration standard (0.004, 0.02, 0.1, 0.5, 2.5, and 10 μg/mL). Methanol/perchloric acid (300 μL of 50/50) is then added into each tube followed by the addition of 20 μL of p-chlorophenylalanine. The samples are vortexed and centrifuged at 14,000 rpm for 10 min. The supernatant is analyzed by LC/MS/MS.

Step C: LC/MS/MS Analysis

An API 4000 LC/MS/MS spectrometer equipped with Agilent 1100 binary pumps, a CTC HTS-PAL autosampler, and a Zorbax XDB C8 4.6×150 mm column is used during the analysis. Appropriate mobile phases can be used such as, for example, (A) 0.1% formic acid, and (B) acetonitrile with 0.1% formic acid. Appropriate gradient conditions can be used such as, for example: 5% B for 0.5 min, then to 98% B in 3 min, maintained at 98% B for 2.5 min, and then returned to 2% B for 2 min. A TurbolonSpray source is used on the API 4000. The analysis is done in an appropriate ion mode and the MRM transition for each analyte is optimized using standard solution. 5 μL of each sample is injected. Non-compartmental analysis is performed using WinNonlin software (v.3.1 Professional Version, Pharsight Corporation, Mountain View, Calif.) on individual animal profiles. Summary statistics on major parameter estimates is performed for $C_{max}$ (peak observed concentration following dosing), $T_{max}$ (time to maximum concentration is the time at which the peak concentration is observed), $AUC_{(0-t)}$ (area under the serum concentration-time curve from time zero to last collection time, estimated using the log-linear trapezoidal method), $AUC_{(0-\infty)}$ (area under the blood concentration time curve from time zero to infinity, estimated using the log-linear trapezoidal method to the last collection time with extrapolation to infinity), and $t_{1/2,z}$ (terminal half-life).

The pharmacokinetic parameters of the creatine phosphate analog following colonic administration of the corresponding prodrug of a creatine phosphate analog are determined and compared to those obtained following an equivalent colonic dose of the creatine phosphate analog. Maximum concentrations of the creatine phosphate analog in the blood ($C_{max}$ values) and the area under blood concentration versus time curve (AUC) values after intracolonic dosing of a prodrug of a creatine phosphate analog that are higher than those achieved for colonic administration of the corresponding creatine phosphate analog indicate that the prodrug provides enhanced colonic bioavailability.

Example 11

Pharmacokinetics of a Prodrug of a Creatine Phosphate Analog Following Intravenous or Oral Administration to Rats A creatine phosphate analog or a corresponding prodrug of the creatine phosphate analog is administered as an intravenous bolus injection or by oral gavage to groups of four to six adult male Sprague-Dawley rats (about 250 g). Animals are conscious at the time of the experiment. When orally administered, the creatine phosphate analog or a corresponding prodrug of the creatine phosphate analog is administered as an aqueous solution (or as a solution of another appropriate solvent optionally including appropriate vehicles) at an appropriate creatine phosphate analog dose equivalent per kg body weight. Blood samples (0.3 mL) are obtained via a jugular vein cannula at intervals over 8 hours following oral dosing. Blood is quenched immediately using, for example, acetonitrile with 1% formic acid and then is frozen at −80° C. until analyzed. Samples may also be taken form the CSF or other appropriate biological fluid.

Three hundred (300) μL of 0.1% formic acid in acetonitrile is added to blank 1.5 mL tubes. Rat blood (300 μL) is collected at different times into tubes containing EDTA and vortexed to mix. A fixed volume of blood (100 μL) is immediately added into the tube and vortexed to mix. Ten microliters of a creatine phosphate analog standard stock solution (0.04, 0.2, 1, 5, 25, and 100 μg/mL) is added to 90 μL of blank rat blood quenched with 300 μL of 0.1% formic acid in acetonitrile. Then, 20 μL of p-chlorophenylalanine is added to each tube to make a final calibration standard (0.004, 0.02, 0.1, 0.5, 2.5, and 10 μg/mL). Samples are vortexed and centrifuged at 14,000 rpm for 10 min. The supernatant is analyzed by LC/MS/MS.

An API 4000 LC/MS/MS spectrometer equipped with Agilent 1100 binary pumps, a CTC HTS-PAL autosampler, and a Phenomenex Synergihydro-RP 4.6×30 mm column were used in the analysis. Appropriate mobile phases and gradient conditions are used for the analysis. The analysis is done in the appropriate ion mode and the MRM transition for each analyte is optimized using standard solutions. Five (5) μL of each sample is injected. Non-compartmental analysis is performed using WinNonlin (v.3.1 Professional Version, Pharsight Corporation, Mountain View, Calif.) on individual animal profiles. Summary statistics on major parameter estimates is performed for $C_1$_a, (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$, (area under the serum concentration time curve from time zero to infinity, estimated using the log-linear trapezoidal method to the last collection time with extrapolation to infinity), and $t_{1/2}$ (terminal half-life).

The oral bioavailability (F(%)) of the creatine phosphate analog is determined by comparing the area under the creatine phosphate analog concentration vs time curve (AUC) following oral administration of a corresponding prodrug of the creatine phosphate analog with the AUC of the creatine phosphate analog concentration vs time curve following intravenous administration of the creatine phosphate analog on a dose normalized basis.

Samples can also be obtained from the CSF and the pharmacokinetics of the creatine phosphate analog and a corresponding prodrug of the creatine phosphate analog determined. Higher levels of creatine phosphate analog and/or the corresponding prodrug of the creatine phosphate analog can indicate that the prodrug has a greater ability to be translocated across the blood-brain barrier compared to the corresponding creatine phosphate analog.

Similar studies on the pharmacokinetics of a creatine phosphate analog and a corresponding prodrug of the creatine phosphate analog can be performed in other animals including, dogs, monkeys, and human.

Example 12

Use of Animal Models to Assess the Efficacy of Prodrugs of Creatine Phosphate Analogs for Treating Amyotrophic Lateral Sclerosis A murine model of SOD1 mutation-associated ALS has been developed in which mice express the human superoxide dismutase (SOD) mutation glycine.fwdarw.alanine at residue 93 (SOD1). These SOD1 mice exhibit a dominant gain of the adverse property of SOD, and develop motor neuron degeneration and dysfunction similar to that of human ALS (Gurney et al., *Science* 1994, 264(5166), 1772-1775; Gurney et al., *Ann. Neurol.* 1996, 39, 147-157; Gurney, *J. Neurol. Sci.* 1997, 152, S67-73; Ripps et al., *Proc Natl Acad Sci U.S.A.* 1995, 92(3), 689-693; and Bruijn et al., *Proc Natl Acad Sci U.S.A.* 1997, 94(14), 7606-7611). The SOD1 transgenic mice show signs of posterior limb weakness at about 3 months of age and die at 4 months. Features common to human ALS include astrocytosis, microgliosis, oxidative stress, increased levels of cyclooxygenase/prostaglandin, and as the disease progresses, profound motor neuron loss.

Studies are performed on transgenic mice overexpressing human Cu/Zn-SOD G93A mutations (B6SJL-TgN (SOD1-G93A) 1 Gur) and non-transgenic B6/SJL mice and their wild litter mates. Mice are housed on a 12-hr day/light cycle and (beginning at 45 d of age) allowed ad libitum access to either test compound-supplemented chow, or as a control, regular formula cold press chow processed into identical pellets. Genotyping can be conducted at 21 days of age as described in Gurney et al., *Science* 1994, 264(5166), 1772-1775. The SOD1 mice are separated into groups and treated with a test compound or serve as controls.

The mice are observed daily and weighed weekly. To assess health status mice are weighed weekly and examined for changes in lacrimation/salivation, palpebral closure, ear twitch and pupillary responses, whisker orienting, postural and righting reflexes and overall body condition score. A general pathological examination is conducted at the time of sacrifice.

Motor coordination performance of the animals can be assessed by one or more methods known to those skilled in the art. For example, motor coordination can be assessed using a neurological scoring method. In neurological scoring, the neurological score of each limb is monitored and recorded according to a defined 4-point scale: 0=normal reflex on the hind limbs (animal splays its hind limbs when lifted by its tail); 1=abnormal reflex of hind limbs (lack of splaying of hind limbs when animal is lifted by the tail); 2=abnormal reflex of limbs and evidence of paralysis; 3=lack of reflex and complete paralysis; and 4=inability to right when placed on the side in 30 seconds or found dead. The primary end point is survival with secondary end points of neurological score and body weight. Neurological score observations and body weight are made and recorded five days per week. Data analysis is performed using appropriate statistical methods.

The rotarod test evaluates the ability of an animal to stay on a rotating dowel allowing evaluation of motor coordination and proprioceptive sensitivity. The apparatus is a 3 cm diameter automated rod turning at, for example, 12 rounds per min. The rotarod test measures how long the mouse can maintain itself on the axle without falling. The test can be stopped after an arbitrary limit of, for example, 120 sec. If the animal falls before 120 sec, the performance is recorded and two additional trials are performed. The mean time of 3 trials is calculated. A motor deficit is indicated by a decrease of walking time.

In the grid test, mice are placed on a grid (length: 37 cm, width: 10.5 cm, mesh size: 1×1 $cm^2$) situated above a plane support. The number of times the mice put their paws through the grid is counted and serves as a measure for motor coordination.

The hanging test evaluates the ability of the animal to hang on a wire. The apparatus is a wire stretched horizontally 40 cm above a table. The animal is attached to the wire by its forepaws. The time needed by the animal to catch the string with its hind paws is recorded (60 sec max) during three consecutive trials.

Electrophysiological measurements (EMG) can also be used to assess motor activity condition. Electromyographic recordings are performed using an electromyography apparatus. During EMG monitoring the mice are anesthetized. The measured parameters are the amplitude and the latency of the compound muscle action potential (CMAP). CMAP is measured in gastrocnemius muscle after stimulation of the sciatic nerve. A reference electrode is inserted near the Achilles tendon and an active needle placed at the base of the tail. A ground needle is inserted on the lower back of the mice. The sciatic nerve is stimulated with a single 0.2 msec pulse at supramaximal intensity (12.9 mA). The amplitude (mV) and the latency of the response (ms) are measured. The amplitude is indicative of the number of active motor units, while distal latency reflects motor nerve conduction velocity.

The efficacy of test compounds can also be evaluated using biomarker analysis. To assess the regulation of protein biomarkers in SOD1 mice during the onset of motor impairment, samples of lumbar spinal cord (protein extracts) are applied to ProteinChip Arrays with varying surface chemical/biochemical properties and analyzed, for example, by surface enhanced laser desorption ionization time of flight mass spectrometry. Then, using integrated protein mass profile analysis methods, data is used to compare protein expression profiles of the various treatment groups. Analysis can be performed using appropriate statistical methods.

Example 13

Clinical Trials to Assess the Efficacy of Prodrugs of Creatine Phosphate Analogs for Treating Parkinson's Disease The following clinical study may be used to assess the efficacy of a prodrug of a creatine phosphate analog in treating Parkinson's disease. Patients with idiopathic PD fulfilling the Queen Square Brain Bank criteria (Gibb et al., *J Neurol Neurosurg Psychiatry* 1988, 51, 745-752) with motor fluctuations and a defined short duration GABA analog response (1.5-4 hours) are eligible for inclusion. Clinically relevant peak dose dyskinesias following each morning dose of their current medication are a further pre-requisite. Patients are also required to have been stable on a fixed dose of treatment for a period of at least one month prior to starting the study. Patients are excluded if their current drug regime includes slow-release formulations of L-Dopa, COMT inhibitors, selegiline, anticholinergic drugs, or other drugs that could potentially interfere with gastric absorption (e.g. antacids). Other exclusion criteria include patients with psychotic symptoms or those on antipsychotic treatment patients with clinically relevant cognitive impairment, defined as MMS (Mini Mental State) score of less than 24 (Folstein et al., *J Psychiatr Res* 1975, 12, 189-198), risk of pregnancy, Hoehn & Yahr stage 5 in off-status, severe, unstable diabetes mellitus, and medical conditions such as unstable cardiovascular disease or moderate to severe renal or hepatic impairment. Full blood count, liver, and renal function blood tests are taken at baseline and after completion of the study.

A randomized, double-blind, and cross-over study design is used. The pharmacokinetics of a prodrug of creatine phosphate analog and the corresponding creatine phosphate analog can be assessed by determining the blood concentrations at appropriate time intervals.

For clinical assessment, motor function is assessed using UPDRS (United Parkinson's Disease Rating Scale) motor score and BrainTest (Giovanni et al., *J Neurol Neurosurg Psychiatry* 1999, 67, 624-629), which is a tapping test performed with the patient's more affected hand on the keyboard of a laptop computer. These tests are carried out at baseline and then immediately following each blood sample until patients reach their full on-stage, and thereafter at intervals until patients reach their baseline off-status. Once patients reach their full on-state, video recordings are performed three times at 20 min intervals. The following mental and motor tasks, which have been shown to increase dyskinesia (Duriff et al., *Mov Disord* 1999, 14, 242-245) are monitored during each video session: (1) sitting still for 1 minute; (2) performing mental calculations; (3) putting on and buttoning a coat; (4) picking up and drinking from a cup of water; and (5) walking. Videotapes are scored using, for example, versions of the Goetz Rating Scale and the Abnormal Involuntary Movements Scale to document a possible increase in test compound induced dyskinesia.

Actual occurrence and severity of dyskinesia is measured with a Dyskinesia Monitor (Manson et al., *J Neurol Neurosurg Psychiatry* 2000, 68, 196-201). The device is taped to a patient's shoulder on their more affected side. The monitor records during the entire time of a challenging session and provides a measure of the frequency and severity of occurring dyskinesias.

Results can be analyzed using appropriate statistical methods.

Example 14

Efficacy of Prodrugs of Creatine Phosphate Analogs in MPTP Induced Neurotoxicity Animal Model of Parkinson's Disease MPTP, or 1-methyl-4-phenyl-1,2,3,6-tetrahydropyridine is a neurotoxin that produces a Parkinsonian syndrome in both man and experimental animals. Studies of the mechanism of MPTP neurotoxicity show that it involves the generation of a major metabolite, $MPP^+$, formed by the activity of monoamine oxidase on MPTP. Inhibitors of monoamine oxidase block the neurotoxicity of MPTP in both mice and primates. The specificity of the neurotoxic effects of $MPP^+$ for dopaminergic neurons appears to be due to the uptake of $MPP^+$ by the synaptic dopamine transporter. Blockers of this transporter prevent $MPP^+$ neurotoxicity. $MPP^+$ has been shown to be a relatively specific inhibitor of mitochondrial complex I activity, binding to complex I at the retenone binding site and impairing oxidative phosphorylation. In vivo studies have shown that MPTP can deplete striatal ATP concentrations in mice. It has been demonstrated that $MPP^+$ administered intrastriatally in rats produces significant depletion of ATP as well as increased lactate concentration confined to the striatum at the site of the injections. Compounds that enhance ATP production can protect against MPTP toxicity in mice.

A prodrug of a creatine phosphate analog is administered to animals such as mice or rats for three weeks before treatment with MPTP. MPTP is administered at an appropriate dose, dosing interval, and mode of administration for 1 week before sacrifice. Control groups receive either normal saline or MPTP hydrochloride alone. Following sacrifice the two striate are rapidly dissected and placed in chilled 0.1 M perchloric acid. Tissue is subsequently sonicated and aliquots analyzed for protein content using a fluorometer assay. Dopamine, 3,4-dihydroxyphenylacetic acid (DOPAC), and homovanillic acid (HVA) are also quantified. Concentrations of dopamine and metabolites are expressed as nmol/mg protein.

Prodrugs of creatine phosphate analogs that protect against DOPAC depletion induced by MPTP, HVA, and/or dopamine depletion are neuroprotective and therefore can be useful for the treatment of Parkinson's disease.

Example 15

Evaluation of Potential Anti-Parkinsonian Activity Using a Haloperidol-Induced Hypolocomotion Animal Model It has been demonstrated that adenosine antagonists, such as theophylline, can reverse the behavioral depressant effects of dopamine antagonists, such as haloperidol, in rodents and is considered a valid method for screening drugs with potential antiparkinsonian effects (Mandhane, et al., *Eur. J. Pharmacol.* 1997, 328, 135-141). The ability of prodrugs of creatine phosphate analogs to block haloperidol-induced deficits in locomotor activity in mice can be used to assess both in vivo and potential anti-Parkinsonian efficacy.

Mice used in the experiments are housed in a controlled environment and allowed to acclimatize before experimental use. 1.5 h before testing, mice are administered 0.2 mg/kg haloperidol, a dose that reduces baseline locomotor activity by at least 50%. A test compound is administered 5-60 min prior to testing. The animals are then placed individually into clean, clear polycarbonate cages with a flat perforated lid. Horizontal locomotor activity is determined by placing the cages within a frame containing a 3×6 array of photocells interfaced to a computer used to tabulate beam interrupts. Mice are left undisturbed to explore for 1 h, and the number of beam interruptions made during this period serves as an indicator of locomotor activity, which is compared with data for control animals for statistically significant differences.

Example 16

6-Hydroxydopamine Animal Model of Parkinson's Disease

The neurochemical deficits seen in Parkinson's disease can be reproduced by local injection of the dopaminergic neurotoxin, 6-hydroxydopamine (6-OHDA) into brain regions containing either the cell bodies or axonal fibers of the nigrostriatal neurons. By unilaterally lesioning the nigrostriatal pathway on only one-side of the brain, a behavioral asymmetry in movement inhibition is observed. Although unilaterally-lesioned animals are still mobile and capable of self maintenance, the remaining dopamine-sensitive neurons on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has been shown to be a sensitive model to predict drug efficacy in the treatment of Parkinson's disease.

Male Sprague-Dawley rats are housed in a controlled environment and allowed to acclimatize before experimental use. Fifteen minutes prior to surgery, animals are given an intraperitoneal injection of the noradrenergic uptake inhibitor desipramine (25 mg/kg) to prevent damage to nondopamine neurons. Animals are then placed in an anaesthetic chamber and anaesthetized using a mixture of oxygen and isoflurane. Once unconscious, the animals are transferred to a stereotaxic frame, where anesthesia is maintained through a mask. The top of the animal's head is shaved and sterilized using an iodine solution. Once dry, a 2 cm long incision is made along the midline of the scalp and the skin retracted and clipped back to expose the skull. A small hole is then drilled through the skull above the injection site. In order to lesion the nigrostriatal pathway, the injection cannula is slowly lowered to position above the right medial forebrain bundle at −3.2 mm anterior posterior, −1.5 mm medial lateral from the bregma, and to a depth of 7.2 mm below the duramater. Two minutes after lowering the cannula, 6-OHDA is infused at a rate of 0.5 µL/min over 4 min, yielding a final dose of 8 µg. The cannula is left in place for an additional 5 min to facilitate diffusion before being slowly withdrawn. The skin is then sutured shut, the animal removed from the stereotaxic frame, and returned to its housing. The rats are allowed to recover from surgery for two weeks before behavioral testing.

Rotational behavior is measured using a rotameter system having stainless steel bowls (45 cm dia×15 cm high) enclosed in a transparent Plexiglas cover running around the edge of the bowl and extending to a height of 29 cm. To assess rotation, rats are placed in a cloth jacket attached to a spring tether connected to an optical rotameter positioned above the bowl, which assesses movement to the left or right either as partial (45°) or full (360°) rotations.

To reduce stress during administration of a test compound, rats are initially habituated to the apparatus for 15 min on four consecutive days. On the test day, rats are given a test compound, e.g., a prodrug of a creatine phosphate analog. Immediately prior to testing, animals are given a subcutaneous injection of a subthreshold dose of apomorphine, and then placed in the harness and the number of rotations recorded for one hour. The total number of full contralatral rotations during the hour test period serves as an index of antiparkinsonian drug efficacy.

Example 17

Animal Studies to Assess the Efficacy of Prodrugs of Creatine Phosphate Analogs Ischemic Injury Adult male rats are given a prodrug of a creatine phosphate analog and, after about 24 h, are anesthetized and prepared for coronary artery occlusion. An additional dose of a prodrug of a creatine phosphate analog is administered at the start of the procedure and the left main coronary artery occluded for 30 min and then released. The same dose of a prodrug of a creatine phosphate analog is then administered at appropriate intervals and duration following surgery. The animals are then studied for cardiac function. Animals receiving a sham injection (saline) demonstrate a large increase in the left end diastolic pressure, indicative of a dilated, stiff heart secondary to myocardial infarction. Prodrugs of creatine phosphate analogs that eliminate or reduce the deficit in cardiac function compared to sham operated control are useful in preventing ischemic injury.

Example 18

Animal Studies to Assess the Ability of Prodrugs of Creatine Phosphate Analogs to Maintain Organ Viability Wistar male rats weighing 300 to 330 g are administered a prodrug of a creatine phosphate analog or vehicle 24 h prior to removal of the heart for ex vivo studies. Animals are sacrificed with pentobarbital (0.3 mL) and intravenously heparinized (0.2 mL). The hearts are initially allowed to equilibrate for 15 min. The left ventricular balloon is then inflated to a volume that gives an end-diastolic pressure of about 8 mm Hg. A left ventricular pressure-volume curve is constructed by incremental inflation of the balloon volume by 0.02 mL aliquots. Zero volume is defined as the point at which the left ventricular end-diastolic pressure is zero. On completion of the pressure-volume curve, the left ventricular balloon is deflated to set end-diastolic pressure back to 8 mmHg and the control period is continued for 15 min after check of coronary flow. The heart is then arrested with 50 mL Celsior+molecule to rest at 4° C. under a pressure of 60 cm $H_2O$. The heart is then removed and stored for 5 h at 4° C. in a plastic container filled with the same solution and surrounded with crushed ice.

After storage, the heart is transferred to a Langendorff apparatus. The balloon catheter is re-inserted into the left ventricle and re-inflated to the same volume as during the preischemic period. The heart is reperfused for at least 2 h at 37° C. The re-perfusion pressure is set at 50 cm $H_2O$ for 15 min of re-flow and then back to 100 cm $H_2O$ for the 2 next h. Pacing (320 beats per min) is re-instituted. Isovolumetric measurements of contractile indexes and diastolic pressure are taken in triplicate at 25, 45, 60, and 120 min of reperfusion. At this time point pressure volume curves are obtained and coronary effluent during the 45 min reperfusion collected to measure creatine kinase leakage. Improved left ventricular pressure following treatment with a prodrug of a creatine phosphate analog, as well as improved volume-pressure curve, decrease of left diastolic ventricular pressure and decrease of creatine kinase leakage indicates the ability of the prodrug of a creatine phosphate analog to maintain organ viability.

Example 19

Neuroprotective Effects of Prodrugs of Creatine Phosphate Analogs in a Transgenic Mouse Model of Huntinaton's Disease Transgenic HD mice of the N171-82Q strain and non-transgenic littermates are treated with a prodrug of a creatine phosphate analog or a vehicle from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice administered prodrugs of creatine phosphate analogs that are neuroprotective in the N171-82Q transgenic HD mouse model remain on the rotarod for a longer period of time and travel further than mice administered vehicle.

Example 20

Efficacy of Prodrugs of Creatine Phosphate Analogs in a Malonate Model of Huntington's Disease A series of reversible and irreversible inhibitors of enzymes involved in energy generating pathways has been used to generate animal models for neurodegenerative diseases such as Parkinson's and Huntington's diseases. Inhibitors of succinate dehydrogenase, an enzyme that impacts cellular energy homeostasis, has been used to generate a model for Huntington's disease (Brouillet et al., *J. Neurochem.* 1993, 60, 356-359; Beal et al., *J. Neurosci.* 1993, 13, 4181-4192; Henshaw et al., *Brain Research* 1994, 647, 161-166 (1994); and Beal et al., *J. Neurochem.* 1993, 61, 1147-1150). The enzyme succinate dehydrogenase plays a central role in both the tricarboxylic acid cycle as well as the electron transport chain in the mitochondria. Malonate is a reversible inhibitor malonate of succinate dehydrogenase. Intrastriatal injections of malonate in rats have been shown to produce dose dependent striatal excitotoxic lesions that are attenuated by both competitive and noncompetitive NMDA antagonists (Henshaw et al., *Brain Research* 1994, 647, 161-166). The glutamate release inhibitor, lamotrigine, also attenuates the lesions. Co-injection with succinate blocks the lesions, consistent with an effect on succinate dehydrogenase. The lesions are accompanied by a significant reduction in ATP levels as well as significant increase in lactate levels in vivo as shown by chemical shift resonance imaging (Beal et al., *J. Neurochem.* 1993, 61, 1147-1150). The lesions produced the same pattern of cellular sparing, which is seen in Huntington's disease, supporting malonate challenge as a useful model for the neuropathologic and neurochemical features of Huntington's disease.

To evaluate the effect of prodrugs of creatine phosphate analogs in this malonate model for Huntington's disease, a prodrug of a creatine phosphate analog is administered at an appropriate dose, dosing interval, and route, to male Sprague-Dawley rats. A prodrug is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 μL of malonate containing 3 μmol are made into the left striatum at the level of the Bregma 2.4 mm lateral to the midline and 4.5 mm ventral to the dura. Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-tiphenyltetrazolium chloride. Slices are stained in the dark at room temperature for 30 min and then removed and placed in 4% paraformaldehyde pH 7.3. Lesions, noted by pale staining, are evaluated on the posterior surface of each section. The measurements are validated by comparison with measurements obtained on adjacent Nissl stain sections.

Compounds exhibiting a neuroprotective effect and therefore useful in treating Huntington's disease show a reduction in malonate-induced lesions.

Finally, it should be noted that there are alternative ways of implementing the disclosures contained herein. Accordingly, the present embodiments are to be considered as illustrative and not restrictive, and the claims are not to be limited to the details given herein, but may be modified within the scope and equivalents thereof.

What is claimed is:

1. A compound of Formula (II):

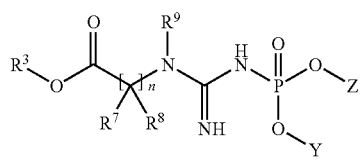

(II)

a pharmaceutically acceptable salt thereof, or a pharmaceutically acceptable solvate of any of the foregoing, wherein:

n is selected from 1 and 2;

Y and Z are independently selected from Formula (1), Formula (2), and Formula (3):

(1)

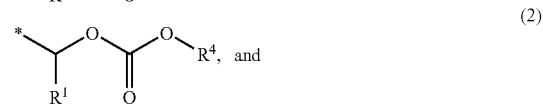

(2)

(3)

wherein:

each X is independently selected from O and S;
each $R^1$ and $R^2$ is independently selected from hydrogen, $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl;
each $R^4$ is independently selected from $C_{1-8}$ alkyl, substituted $C_{1-8}$ alkyl, $C_{1-8}$ heteroalkyl, substituted $C_{1-8}$ heteroalkyl, $C_{3-12}$ cycloalkyl, substituted $C_{3-12}$ cycloalkyl, $C_{4-20}$ cycloalkylalkyl, substituted $C_{4-20}$ cycloalkylalkyl, $C_{4-20}$ heterocycloalkylalkyl, substituted $C_{4-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl; and
each $R^6$ is independently selected from hydrogen, $C_{1-8}$ alkyl, substituted $C_{1-8}$ alkyl, $C_{5-12}$ cycloalkyl, substituted $C_{5-12}$ cycloalkyl, $C_{5-12}$ aryl, and $C_{5-12}$ substituted aryl;
$R^3$ is selected from hydrogen, $C_{1-8}$ alkyl, substituted $C_{1-8}$ alkyl, $C_{1-8}$ heteroalkyl, substituted $C_{1-8}$ heteroalkyl, $C_{5-12}$ cycloalkyl, substituted $C_{5-12}$ cycloalkyl, $C_{6-20}$ cycloalkylalkyl, substituted $C_{6-20}$ cycloaklkyl, $C_{6-20}$ heterocycloalkylalkyl, substituted $C_{6-20}$ heterocycloalkylalkyl, $C_{5-12}$ aryl, substituted $C_{5-12}$ aryl, $C_{5-12}$ heteroaryl, substituted $C_{5-12}$ heteroaryl, $C_{6-20}$ arylalkyl, substituted $C_{6-20}$ arylalkyl, $C_{6-20}$ heteroarylalkyl, and substituted $C_{6-20}$ heteroarylalkyl;
each $R^7$ and $R^8$ is independently selected from hydrogen, $C_{1-8}$ and substituted $C_{1-8}$ alkyl; and
$R^9$ is selected from hydrogen, $C_{1-8}$ alkyl, substituted $C_{1-8}$ alkyl, $C_{1-8}$ heteroalkyl, and substituted $C_{1-8}$ heteroalkyl.

2. The compound of claim 1, wherein n is 1.

3. The compound of claim 1, wherein n is 2.

4. The compound of claim 1, wherein each X is O.

5. The compound of claim 1, wherein each X is S.

6. The compound of claim 1, wherein each $R^1$ and $R^2$ is independently selected from hydrogen, $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl.

7. The compound of claim 1, wherein each $R^1$ is independently selected from hydrogen, methyl, ethyl, n-propyl, isopropyl, butyl, isobutyl, sec-butyl, tert-butyl, phenyl, and cyclohexyl.

8. The compound of claim 1, wherein each $R^2$ is independently selected from hydrogen, methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl.

9. The compound of claim 1, wherein each $R^2$ is independently selected from hydrogen, methyl, ethyl, n-propyl, isopropyl, n-butyl, isobutyl, sec-butyl, terr-butyl, n-pentyl, isopentyl, sec-pentyl, neopentyl, 1, 1-diethoxyethyl, phenyl, cyclohexyl, and 3-pyridyl.

10. The compound of claim 1, wherein each $R^4$ is independently selected from $C_{1-6}$ alkyl, substituted $C_{1-6}$ alkyl, $C_{3-7}$ cycloalkyl, substituted $C_{3-7}$ cycloalkyl, $C_{5-7}$ aryl, and substituted $C_{5-7}$ aryl.

11. The compound of claim 1, wherein each $R^4$ is independently selected from methyl, ethyl, n-propyl, isopropyl, butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl.

12. The compound of claim 1, wherein each $R^4$ is independently selected from methyl, ethyl, n-propyl, isopropyl, n-butyl, isobutyl, sec-butyl, rert-butyl, n-pentyl, isopentyl, sec-pentyl, neopentyl, 1,1 -diethoxyethyl, phenyl, cyclohexyl, and 3-pyridyl.

13. The compound of claim 1, wherein $R^3$ is selected from hydrogen, benzyl, and $C_{1-4}$ alkyl.

14. The compound of claim 1, wherein $R^3$ is hydrogen.

15. The compound of claim 1, wherein each $R^6$ is independently selected from methyl, ethyl, n-propyl, isopropyl, terr-butyl, phenyl, and cyclohexyl.

16. The compound of claim 1, wherein each $R^6$ is methyl.

17. The compound of claim 1, wherein each $R^7$ and $R^8$ is hydrogen.

18. The compound of claim 1, wherein $R^9$ is selected from hydrogen and $C_{1-4}$ alkyl.

19. The compound of claim 1, wherein $R^9$ is hydrogen.

20. The compound of claim 1, wherein each substituent group is independently selected from halogen, $-NO_2$, $-OH$, $-COOH$, $-NH_2$, $-CN$, $CF_3$, $-OCF_3$, $C_{1-8}$ alkyl, substituted $C_{1-8}$ alkyl, $C_{1-8}$ alkoxy, and substituted $C_{1-8}$ alkoxy.

21. A pharmaceutical composition comprising a therapeutically effective amount of at least one compound of claim 1, and a pharmaceutically acceptable vehicle.

22. The pharmaceutical composition of claim 21, formulated in one or more sustained release oral dosage forms.

23. The pharmaceutical composition of claim 21, a daily dose of a corresponding creatine phosphate analog of Formula (IV) is provided

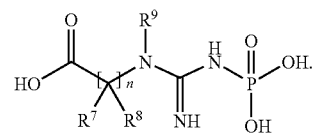

(IV)

24. The pharmaceutical composition of claim 23, wherein the dose comprises from about 1 mg-equivalents to about 20,000 mg-equivalents of the creatine phosphate analog of Formula (IV).

25. The pharmaceutical composition of claim 23, wherein the dose comprises from about 100 mg-equivalents to about 12,000 mg-equivalents of the creatine phosphate analog of Formula (IV).

26. The pharmaceutical composition of claim 23, wherein the dose comprises from about 1000 mg-equivalents to about 10,000 mg-equivalents of the creatine phosphate analog of Formula (IV).

* * * * *